(12) United States Patent
Hiebert et al.

(10) Patent No.: US 8,563,505 B2
(45) Date of Patent: *Oct. 22, 2013

(54) HEPATITIS C VIRUS INHIBITORS

(75) Inventors: Sheldon Hiebert, Middletown, CT (US); Michael S. Bowsher, Wallingford, CT (US); Ramkumar Rajamani, Middletown, CT (US); Rongti Li, Wallingford, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 490 days.

This patent is subject to a terminal disclaimer.

(21) Appl. No.: 12/566,441

(22) Filed: Sep. 24, 2009

(65) Prior Publication Data
US 2010/0080771 A1 Apr. 1, 2010

Related U.S. Application Data

(60) Provisional application No. 61/100,901, filed on Sep. 29, 2008.

(51) Int. Cl.
*A61K 38/00* (2006.01)
*A01N 37/18* (2006.01)

(52) U.S. Cl.
USPC .......................................................... 514/3.7

(58) Field of Classification Search
None
See application file for complete search history.

(56) References Cited

U.S. PATENT DOCUMENTS

| | | | |
|---|---|---|---|
| 5,223,432 A | 6/1993 | Wirz et al. | |
| 7,449,479 B2 | 11/2008 | Wang et al. | |
| 7,582,605 B2 | 9/2009 | Moore et al. | |
| 7,592,336 B2 * | 9/2009 | Sin et al. | 514/235.5 |
| 7,601,709 B2 | 10/2009 | Miao et al. | |
| 7,605,126 B2 | 10/2009 | Niu et al. | |
| 7,635,683 B2 | 12/2009 | Gai et al. | |
| 7,888,464 B2 * | 2/2011 | Wang et al. | 530/331 |
| 7,964,560 B2 * | 6/2011 | Wang et al. | 514/4.1 |
| 2005/0209135 A1 | 9/2005 | Busacca et al. | |
| 2006/0199773 A1 | 9/2006 | Sausker et al. | |
| 2006/0257980 A1 | 11/2006 | Li | |
| 2007/0078081 A1 | 4/2007 | Casarez et al. | |
| 2008/0181868 A1 | 7/2008 | Sun et al. | |
| 2008/0279821 A1 | 11/2008 | Niu et al. | |
| 2009/0274656 A1 | 11/2009 | Wang et al. | |
| 2010/0080770 A1 * | 4/2010 | Hiebert et al. | 424/85.2 |

FOREIGN PATENT DOCUMENTS

| | | |
|---|---|---|
| WO | WO 98/17679 | 4/1998 |
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/08244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |

(Continued)

OTHER PUBLICATIONS

U.S. Appl. No. 12/559,179, filed Sep. 14, 2009, Hiebert et al.

(Continued)

*Primary Examiner* — Thomas Heard
(74) *Attorney, Agent, or Firm* — Pamela A. Mingo; Mary K. VanAtten

(57) ABSTRACT

Hepatitis C virus inhibitors having the general formula

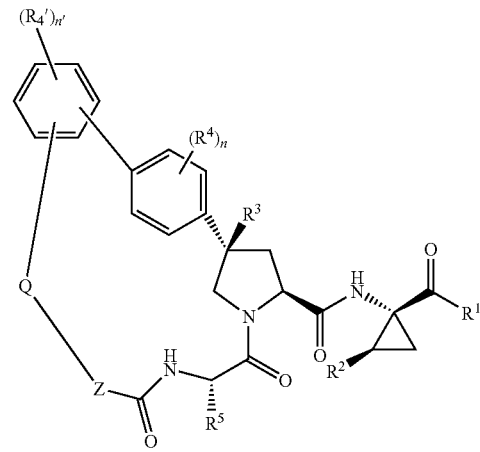

are disclosed. Compositions comprising the compounds and methods for using the compounds to inhibit HCV are also disclosed.

10 Claims, No Drawings

(56) References Cited

FOREIGN PATENT DOCUMENTS

| | | |
|---|---|---|
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |
| WO | WO 2006/119061 | 11/2006 |
| WO | WO 2006/122188 | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |
| WO | WO 2008/051475 | 5/2008 |
| WO | WO 2008/051477 | 5/2008 |
| WO | WO 2008/051514 | 5/2008 |
| WO | WO 2008/057208 | 5/2008 |
| WO | WO 2008/057209 | 5/2008 |
| WO | WO 2008/057871 | 5/2008 |
| WO | WO 2008/057873 | 5/2008 |
| WO | WO 2008/057875 | 5/2008 |
| WO | WO 2008/057995 | 5/2008 |
| WO | WO 2008/059046 | 5/2008 |
| WO | WO 2008/060927 | 5/2008 |
| WO | WO 2008/064057 | 5/2008 |
| WO | WO 2008/064061 | 5/2008 |
| WO | WO 2008/064066 | 5/2008 |
| WO | WO 2008/070358 | 6/2008 |
| WO | WO 2008/092954 | 8/2008 |
| WO | WO 2008/092955 | 8/2008 |
| WO | WO 2008/095058 | 8/2008 |
| WO | WO 2008/095999 | 8/2008 |
| WO | WO 2008/096001 | 8/2008 |
| WO | WO 2008/096002 | 8/2008 |
| WO | WO 2008/098368 | 8/2008 |
| WO | WO 2008/101665 | 8/2008 |
| WO | WO 2008/106130 | 9/2008 |
| WO | WO 2008/128921 | 10/2008 |
| WO | WO 2008/134395 | 11/2008 |
| WO | WO 2008/134397 | 11/2008 |
| WO | WO 2008/134398 | 11/2008 |
| WO | WO 2008/137779 | 11/2008 |
| WO | WO 2008/141227 | 11/2008 |
| WO | WO 2009/005690 | 1/2009 |
| WO | WO 2009/010804 | 1/2009 |
| WO | WO 2009/014730 | 1/2009 |
| WO | WO 2009/082701 | 7/2009 |
| WO | WO 2009/085659 | 7/2009 |
| WO | WO 2009/129109 | 10/2009 |
| WO | WO 2009/140475 | 11/2009 |
| WO | WO 2009/140500 | 11/2009 |
| WO | WO 2009/142842 | 11/2009 |
| WO | WO 2009/146347 | 12/2009 |
| WO | WO 2009/148923 | 12/2009 |

OTHER PUBLICATIONS

U.S. Appl. No. 12/566,286, filed Sep. 24, 2009, Wang et al.
U.S. Appl. No. 12/628,248, filed Dec. 1, 2009, Hiebert et al.
U.S. Appl. No. 12/635,144, filed Dec. 10, 2009, Wang et al.
Lauer, G.M. et al., "Hepatitis C Virus Infection", The New England Journal of Medicine, vol. 345, No. 1, pp. 41-52 (2001).
Llinàs-Brunet, M. et al., "A Systematic Approach to the Optimization of Substrate-Based Inhibitors of the Hepatitis C Virus NS3 Protease: Discovery of Potent and Specific Tripeptide Inhibitors", Journal of Medicinal Chemistry, vol. 47, No. 26, pp. 6584-6594 (2004).
Poupart, M.-A. et al., "Solid-Phase Synthesis of Peptidomimetic Inhibitors for the Hepatitis C Virus NS3 Protease", The Journal of Organic Chemistry, vol. 66, No. 14, pp. 4743-4751 (2001).
Ribeiro, C.M.R. et al., "Ultrasound in enzymatic resolution of ethyl 3-hydroxy-3-phenylpropanoate", Tetrahedron Letters, vol. 42, pp. 6477-6479 (2001).
Tsantrizos, Y.S. et al., "Olefin ring-closing metathesis as a powerful tool in drug discovery and development—potent macrocyclic inhibitors of the hepatitis C virus NS3 protease", Journal of Organometallic Chemistry, vol. 691, pp. 5163-5174 (2006).
Wirz, B. et al., "Enzymatic preparation of homochiral 2-isobutyl succinic acid derivatives", Tetrahedron: Asymmetry, vol. 8, No. 2, pp. 187-189 (1997).
Yang, S., "Chemoenzymatic Synthesis of (R)-(—)-Citramalic Acid", Synthesis, pp. 365-366 (1992).

* cited by examiner

HEPATITIS C VIRUS INHIBITORS

CROSS-REFERENCE TO RELATED APPLICATIONS

This application claims the benefit of U.S. Provisional Application Ser. No. 61/100,901 filed Sep. 29, 2008.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with additional compounds having anti-HCV activity:

In its first aspect the present disclosure provides a compound of formula (I)

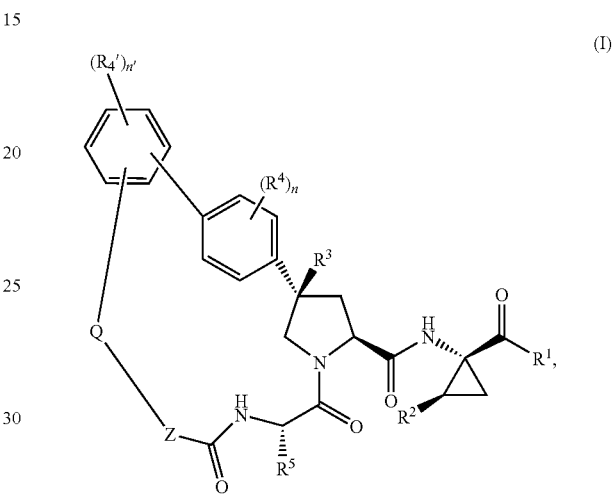

or a pharmaceutically acceptable salt thereof, wherein
n and n' are each independently 0, 1, 2 or 3;
$R^1$ is selected from hydroxy and —$NHSO_2R^6$;
$R^2$ is selected from hydrogen, alkenyl, alkyl, and cycloalkyl, wherein the alkenyl, the alkyl, and the cycloalkyl are each optionally substituted with one, two, three, or four halo groups;
$R^3$ is selected from hydrogen, alkoxy, alkylsulfanyl, alkylsulfonyl, alkylsulfoxyl, and hydroxy;
each $R^4$ and $R^{4'}$ are independently selected from alkoxy, alkyl, cyano, halo, haloalkoxy, haloalkyl, hydroxy, and —$NR^aR^b$;
$R^5$ is selected from hydrogen, alkenyl, alkyl, aryl, arylalkyl, cycloalkyl, (cycloalkyl)alkyl, heterocyclyl, and heterocyclylalkyl; wherein the alkyl and cycloalkyl are each optionally substituted with one group selected from alkoxy, haloalkoxy, halo, haloalkyl, cyano, and dialkylamino;
$R^6$ is selected from alkyl, aryl, arylalkyl, cycloalkyl, (cycloalkyl)alkyl, heterocyclyl, and —$NR^aR^b$; wherein the alkyl and cycloalkyl are each optionally substituted with one group selected from alkyl, alkoxy, halo, haloalkyl, cyano, cyanoalkyl, and haloalkoxy;
$R^a$ and $R^b$ are independently selected from hydrogen, alkoxy, alkyl, aryl, arylalkyl, cycloalkyl, (cycloalkyl)alkyl, haloalkyl, heterocyclyl, and heterocyclylalkyl;
Q is a $C_{4-8}$ saturated or unsaturated chain, wherein the chain is optionally substituted with one, two, three, or four groups independently selected from alkyl, halo, and haloalkyl, wherein the alkyl and haloalkyl groups can optionally form a 1-7 membered ring with the carbon atom to which they are attached; and
Z is selected from O, $CH_2$, and $NR^z$, wherein $R^z$ is selected from hydrogen and alkyl.

In a first embodiment of the first aspect the present disclosure provides a compound of formula (I), or a pharmaceutically acceptable salt thereof, wherein $R^1$ is —NHSO$_2$R$^6$. In a second embodiment of the first aspect n and n' are each 0 or 1. In a third embodiment of the first aspect Q is a C$_{4-7}$ saturated unsubstituted chain and Z is O. In a fourth embodiment of the first aspect $R^3$ is alkoxy. In a fifth embodiment of the first aspect $R^2$ is selected from alkenyl, alkyl substituted with two halo groups, and unsubstituted cycloalkyl. In a sixth embodiment of the first aspect $R^5$ is alkyl.

In a seventh embodiment of the first aspect the present disclosure provides a compound of formula (I), or a pharmaceutically acceptable salt thereof, wherein $R^1$ is —NHSO$_2$R$^6$;
$R^2$ is selected from alkenyl, alkyl substituted with two halo groups, and unsubstituted cycloalkyl; and
$R^5$ is alkyl.

In an eighth embodiment of the first aspect the present disclosure provides a compound of formula (I), or a pharmaceutically acceptable salt thereof, wherein n and n' are each 0 or 1;
$R^1$ is —NHSO$_2$R$^6$; wherein $R^6$ is cycloalkyl;
$R^2$ is selected from alkenyl, alkyl substituted with two halo groups, and unsubstituted cycloalkyl;
$R^3$ is alkoxy;
$R^5$ is alkyl;
Q is a C$_{4-7}$ saturated unsubstituted chain; and
Z is O.

In a second aspect the present disclosure provides a composition comprising the compound of Formula (I), or a pharmaceutically acceptable salt thereof, and a pharmaceutically acceptable carrier. In a first embodiment of the second aspect the composition further comprises at least one additional compound having anti-HCV activity. In a second embodiment of the second aspect at least one of the additional compounds is an interferon or a ribavirin. In a third embodiment of the second aspect the interferon is selected from interferon alpha 2B, pegylated interferon alpha, consensus interferon, interferon alpha 2A, and lymphoblastoid interferon tau.

In a fourth embodiment of the second aspect the present disclosure provides a composition comprising the compound of Formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the second aspect the present disclosure provides a composition comprising the compound of Formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a third aspect the present disclosure provides a composition comprising a compound of Formula (I), or a pharmaceutically acceptable salt thereof, one, two, three, four, or five additional compounds having anti-HCV activity, and a pharmaceutically acceptable carrier. In a first embodiment of the third aspect the composition comprises three or four additional compounds having anti-HCV activity. In a second embodiment of the third aspect the composition comprises one or two additional compounds having anti-HCV activity.

In a fourth aspect the present disclosure provides a method of treating an HCV infection in a patient, comprising administering to the patient a therapeutically effective amount of Formula (I), or a pharmaceutically acceptable salt thereof. In a first embodiment of the fourth aspect the method further comprises administering at least one additional compound having anti-HCV activity prior to, after, or simultaneously with the compound of Formula (I), or a pharmaceutically acceptable salt thereof. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, and lymphoblastoid interferon tau.

In a fourth embodiment of the fourth aspect the present disclosure provides a method of treating an HCV infection in a patient, comprising administering to the patient a therapeutically effective amount of Formula (I), or a pharmaceutically acceptable salt thereof, and at least one additional compound having anti-HCV activity prior to, after, or simultaneously with the compound of Formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the fourth aspect the present disclosure provides a method of treating an HCV infection in a patient, comprising administering to the patient a therapeutically effective amount of Formula (I), or a pharmaceutically acceptable salt thereof, and at least one additional compound having anti-HCV activity prior to, after, or simultaneously with the compound of Formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fifth aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of the fifth aspect the method comprises administering three or four additional compounds having anti-HCV activity. In a second embodiment of the fifth aspect the method comprises administering one or two additional compounds having anti-HCV activity.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^4$ groups may be the same or different.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkyl," as used herein, refers to a group derived from a straight or branched chain saturated hydrocarbon containing from one to six carbon atoms.

The term "alkylsulfanyl," as used herein, refers to an alkyl group attached to the parent molecular moiety through a sulfur atom.
branched chain saturated hydrocarbon containing from one to six carbon atoms.

The term "alkylsulfaonyl," as used herein, refers to an alkyl group attached to the parent molecular moiety through a sulfonyl group.
branched chain saturated hydrocarbon containing from one to six carbon atoms.

The term "alkylsulfoxyl," as used herein, refers to an alkyl group attached to the parent molecular moiety through a sulfoxyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present invention can be attached to the parent molecular moiety through any substitutable carbon atom in the group. Representative examples of aryl groups include, but are not limited to, indanyl, indenyl, naphthyl, phenyl, and tetrahydronaphthyl.

The term "arylalkyl," as used herein, refers to an alkyl group substituted with one, two, or three aryl groups.

The term "cyano," as used herein, refers to —CN.

The term "cyanoalkyl," as used herein, refers to an alkyl group substituted with one, two, or three cyano groups.

The term "cycloalkyl," as used herein, refers to a saturated monocyclic or bicyclic hydrocarbon ring system having three to seven carbon atoms and zero heteroatoms. Representative examples of cycloalkyl groups include, but are not limited to, cyclopropyl, cyclobutyl, and cyclopentyl.

The term "(cycloalkyl)alkyl," as used herein, refers to an alkyl group substituted with one, two, or three cycloalkyl groups.

The term "dialkylamino," as used herein, refers to —NRpRq, wherein Rp and Rq are alkyl groups. The alkyl groups may be the same or different.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group; and tricyclic groups in which a bicyclic system is fused to a phenyl group, a monocyclic cycloalkenyl group, a monocyclic cycloalkyl group, or another monocyclic heterocyclyl group. The heterocyclyl groups of the present invention can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "heterocyclylalkyl," as used herein, refers to an alkyl group substituted with one, two, or three heterocyclyl groups.

The term "hydroxy," as used herein, refers to —OH.

The term "—$NR^aR^b$," as used herein, refers to two groups, $R^a$ and $R^b$, which are attached to the parent molecular moiety through a nitrogen atom. $R^a$ and $R^b$ are independently selected from hydrogen, alkoxy, alkyl, aryl, arylalkyl, cycloalkyl, (cycloalkyl)alkyl, haloalkyl, heterocyclyl, and heterocyclylalkyl.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "sulfonyl," as used herein, refers to —SO$_2$—.

The term "sulfonyl," as used herein, refers to —S(O)—.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

Asymmetric centers exist in the compounds of the present disclosure. For example, the compounds may include P1 cyclopropyl element of formula

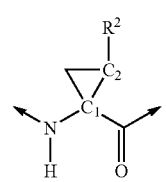

P1 wherein $C_1$ and $C_2$ each represent an asymmetric carbon atom at positions 1 and 2 of the cyclopropyl ring.

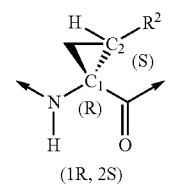

(1R, 2S)
$R^2$ is syn to carbonyl

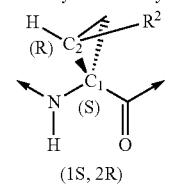

(1S, 2R)
$R^2$ is syn to carbonyl

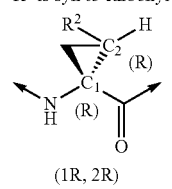

(1R, 2R)
$R^2$ is syn to amide

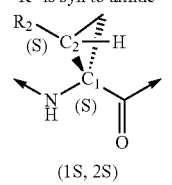

(1S, 2S)
$R^2$ is syn to amide

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin inhibitors | Novartis |
| Debio-025 | | | Debiopharm |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/ Elan Pharmaceuticals Inc., New York, NY |

TABLE 1-continued

| Brand Name | Physiological Class | Type of Inhibitor or Target | Source Company |
|---|---|---|---|
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO2005/047288 26 May 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novartis |
| 2'C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH 503034 | Antiviral | Serine protease inhibitor | Schering Plough |
| Zadazim | Immune modulator | Immune modulator | SciClone Pharmaceuticals Inc., San Mateo, CA |
| Ceplene | Immunomodulator | Immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon - α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |

TABLE 1-continued

| Brand Name | Physiological Class | Type of Inhibitor or Target | Source Company |
|---|---|---|---|
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering Plough |
| TMS-435 | Antiviral | Serine protease inhibitor | Tibotec BVBA, Mechelen, Belgium |
| BI-201335 | Antiviral | Serine protease inhibitor | Boehringer Ingelheim Pharma KG, Ingelheim, Germany |
| MK-7009 | Antiviral | Serine protease inhibitor | Merck |
| PF-00868554 | Antiviral | Replicase inhibitor | Pfizer |
| ANA598 | Antiviral | Non-Nucleoside NS5B polymerase inhibitor | Anadys Pharmaceuticals, Inc., San Diego, CA, USA |
| IDX375 | Antiviral | Non-Nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| VCH-759 | Antiviral | NS5B polymerase inhibitor | ViroChem Pharma |
| VCH-916 | Antiviral | NS5B polymerase inhibitor | ViroChem Pharma |

TABLE 1-continued

| Brand Name | Physiological Class | Type of Inhibitor or Target | Source Company |
|---|---|---|---|
| GS-9190 | Antiviral | NS5B polymerase inhibitor | Gilead |
| Peg-interferon lamda | Antiviral | Interferon | ZymoGenetics/ Bristol-Myers Squibb |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel ($SiO_2$) according to Still's flash chromatography technique (*J. Org. Chem.* 1978, 43, 2923).

The abbreviations used in the present application, including particularly in the illustrative schemes and examples which follow, are well-known to those skilled in the art. Some of the abbreviations used are as follows: Ph for phenyl; $PPh_3$ for triphenylphosphine; DME for 1,2-dimethoxyethane; EtOAc for ethyl acetate; $Et_3N$ for triethylamine; TMS for trimethylsilyl; DCM for dichloromethane; Me for methyl; DMF for N,N-dimethylformamide; TBAF for tetrabutylammonium fluoride; THF for tetrahydrofuran; Hex for hexanes; TFA for trifluoroacetic acid; HATU for O-(7-azabenzotriazol-1-yl)-N,N,N',N'-tetramethyluronium phosphate; DCE for 1,2-dichloroethane; MeOH for methanol; MeOD for $CD_4OD$; pTSA or pTsoH for para-toluenesulfonic acid; and DIEA for diisopropylethylamine.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Preparation of Intermediate 1:

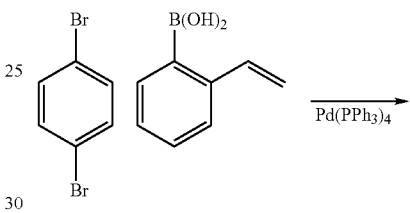

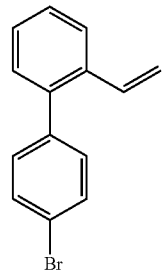

Intermediate 1

A solution of 1,4-dibromobenzene (4.56 g, 19.33 mmol), potassium carbonate (6.16 g, 44.6 mmol) and 2-vinylphenylboronic acid (2.2 g, 14.87 mmol) in DME (75 mL) and water (15 mL) (in a pressure vessel) was bubbled with nitrogen for 15 min. Tetrakis(triphenylphosphine) palladium(0) (0.859 g, 0.743 mmol) was added to the vessel and bubbled with nitrogen for 15 min. The reaction was then heated to 90° C. overnight. The reaction was cooled to r.t. and partially concentrated. The residue was diluted in EtOAc and washed with water then brine, dried over $MgSO_4$, filtered and evaporated to give the crude material. The crude material was purified on the Biotage (100% hexanes) to give 4'-bromo-2-vinylbiphenyl (Intermediate 1, 2.43 g, 63% yield) as a clear oil. $^1$H NMR (500 MHz, chloroform-d) δ ppm 5.22 (dd, J=10.99, 1.22 Hz, 1H) 5.71 (dd, J=17.40, 1.22 Hz, 1H) 6.67 (dd, J=17.40, 10.99 Hz, 1H) 7.20-7.25 (m, 3H) 7.31-7.40 (m, 2H) 7.52-7.58 (m, 2H) 7.62-7.67 (m, 1H).

Preparation of Intermediate 2:

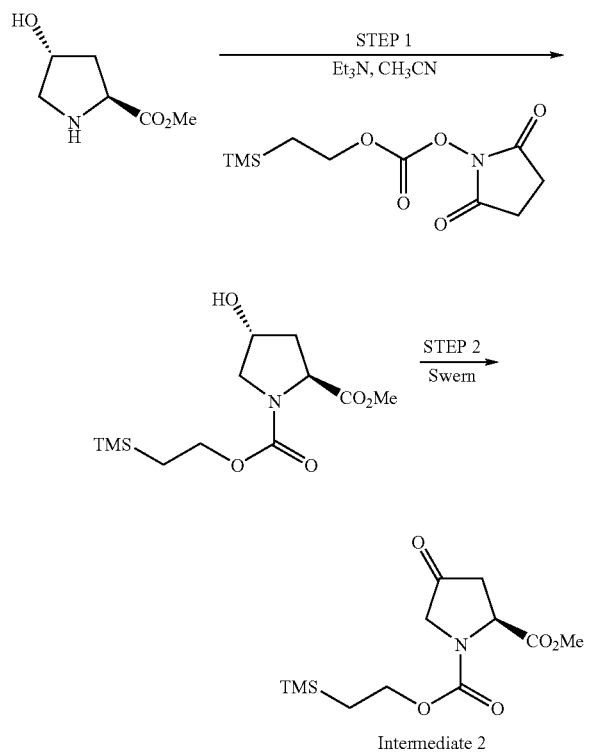 [SMILES: COC(=O)[C@@H]1C[C@@H](O)CN1 ; C[Si](C)(C)CCOC(=O)ON1C(=O)CCC1=O ; COC(=O)[C@@H]1C[C@@H](O)CN1C(=O)OCC[Si](C)(C)C ; COC(=O)[C@@H]1CC(=O)CN1C(=O)OCC[Si](C)(C)C]

Intermediate 2

Preparation of Intermediate 3:

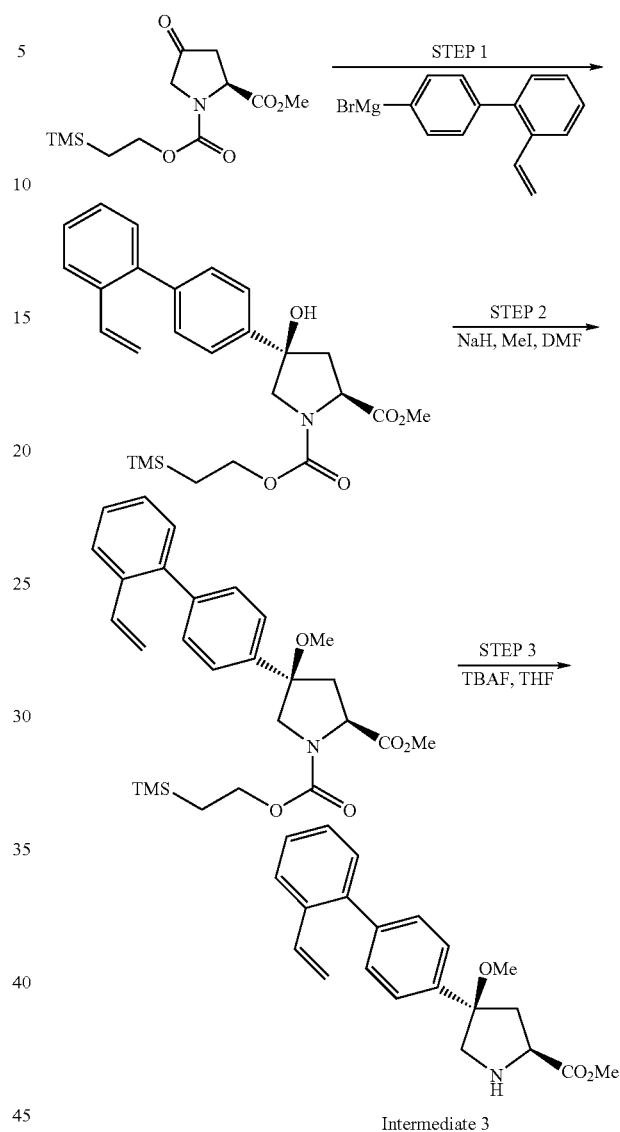

Intermediate 3

Step 1:

2,5-dioxopyrrolidin-1-yl 2-(trimethylsilylethyl carbonate (11.73 g, 45.2 mmol) was added to a solution of (2S,4R)-methyl 4-hydroxypyrrolidine-2-carboxylate, HCl salt (9.86 g, 54.3 mmol) and triethylamine (18.9 mL, 136 mmol) in acetonitrile (240 mL) and stirred at r.t. overnight. The reaction was quenched with water and ether. The organic layer was washed with 1.0M HCl (2×) and then brine. It was then dried over MgSO₄, filtered and evaporated to give the product. $^1$H NMR (500 MHz, CHLOROFORM-d) δ ppm 0.05 (s, 9H) 0.95 (t, J=8.70 Hz, 1H) 0.98-1.13 (m, 1H) 1.83 (d, J=16.79 Hz, 1H) 2.11 (ddd, J=13.20, 7.86, 4.88 Hz, 1H) 2.20-2.39 (m, 1H) 3.58-3.71 (m, 1H) 3.75 (d, J=11.60 Hz, 3H) 4.08-4.27 (m, 2H) 4.41-4.60 (m, 2H).

Step 2:

Oxalyl chloride (8.9 ml, 93 mmol) was added dropwise to a solution of dimethylsulfoxide (13.2 ml, 186 mmol) in DCM (180 ml) at −78° C. The formed solution was stirred at this temperature for 30 min. A solution of (2S,4R)-2-methyl 1-(2-(trimethylsilyl)ethyl) 4-hydroxypyrrolidine-1,2-dicarboxylate (12.25 g, 42.3 mmol) in DCM (30 mL) was added at −78° C. The formed slurry was stirred at −78° C. for 1 hr before addition of triethylamine (29.5 ml, 212 mmol) dropwise. This solution was stirred at room temperature 30 min. and then washed with 1M HCl and brine, dried over MgSO₄, filtered, and evaporated. The residual light brown oil was purified by flash chromatography on the Biotage (0-33% EtOAc in hexanes) to give (S)-2-methyl 1-(2-(trimethylsilyl)ethyl) 4-oxopyrrolidine-1,2-dicarboxylate (Intermediate 2, 9.5 g, 78% yield) as an orange oil. $^1$H NMR (500 MHz, chloroform-d) δ ppm −0.04-0.12 (m, 9H) 0.91-1.09 (m, 2H) 2.61 (dd, J=18.77, 2.59 Hz, 1H) 2.87-3.04 (m, 1H) 3.77 (s, 3H) 3.92 (br. s., 2H) 4.19-4.26 (m, 2H) 4.86 (d, J=10.07 Hz, 1H).

Step 1:

Magnesium (0.110 g, 4.58 mmol) turnings were stirred in a round bottom flask under nitrogen for 30 min. to cause scratching of the surface of the magnesium. 10 mL of THF was added to the magnesium turnings and stirred for an additional 30 min. 4'-bromo-2-vinylbiphenyl (Intermediate 1, 1.13 g, 4.36 mmol) in THF (30 mL), was added dropwise at reflux with vigorous stirring. The Grignard solution (40 mL) was added to a solution of (S)-2-methyl 1-(2-(trimethylsilyl)ethyl) 4-oxopyrrolidine-1,2-dicarboxylate (Intermediate 2, 1.0 g, 3.53 mmol) in toluene (30 mL) at 0° C. and stirred for 1 hr and then quenched with a saturated NH₄Cl solution. The aqueous layer was extracted with DCM. The combined organics were washed with brine and dried over MgSO₄, filtered and evaporated to give crude material. The crude material was purified by flash chromatography on the Biotage (20-33% EtOAc:Hex) to give (2S,4R)-2-methyl 1-(2-((trimethylsilyl)ethyl) 4-hydroxy-4-(2'-vinylbiphenyl-4-yl)pyrrolidine-1,2-dicarboxylate (0.5 g, 30% yield) as a yellow oil. LCMS: rt=1.92 min. [M+Na]⁺=490; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. ¹H NMR (500 MHz, CHLOROFORM-d) δ ppm 0.06 (s, 9H) 0.88-1.14 (m, 2H) 2.38-2.50 (m, 1H) 2.74 (dd, J=13.58, 10.22 Hz, 1H) 3.89 (d, J=11.60 Hz, 2H) 3.76-3.84 (m, 1H) 3.86 (s, 3H) 4.00 (dd, 1H) 4.23 (s, 1H) 4.24-4.28 (m, 1H) 4.55-4.66 (m, 1H) 5.20 (dd, J=10.9, 1.22 Hz, 1H) 5.71 (dd, J=17.55, 1.07 Hz, 1H) 6.70 (dd, J=17.40, 10.99 Hz, 1H) 7.28 (dd, 1H) 7.34 (dd, J=7.17, 1.68 Hz, 1H) 7.37 (d, J=8.55 Hz, 2H) 7.54 (d, J=8.24 Hz, 2H) 7.65 (d, J=7.32 Hz, 1H).

Step 2:

Sodium hydride (60% in oil) (0.08 g, 1.925 mmol) was added to a solution of (2S,4R)-2-methyl 1-(2-(trimethylsilyl)ethyl) 4-hydroxy-4-(2'-vinylbiphenyl-4-yl)pyrrolidine-1,2-dicarboxylate (0.5 g, 1.069 mmol) and methyl iodide (0.12 mL, 1.925 mmol) at 0° C. in DMF. This was stirred at 0° C. for 3 hrs. The reaction was then quenched with a saturated NH₄Cl solution and ether. The ether layer was washed with brine, dried over MgSO₄, filtered and evaporated to give crude material. The crude material was purified by flash chromatography on the Biotage (20-40% EtOAc in hexanes) to give (2S,4R)-2-methyl 1-(2-(trimethylsilyl)ethyl) 4-methoxy-4-(2'-vinylbiphenyl-4-yl)pyrrolidine-1,2-dicarboxylate (160 mg, 31% yield) as a clear oil. LCMS: rt=2.11 min. [M+Na]⁺=504; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. ¹H NMR (500 MHz, CHLOROFORM-d) δ ppm −0.04-0.13 (m, 9H) 0.95-1.02 (m, 1H) 1.03-1.08 (m, 1H) 2.55 (dd, J=13.12, 8.85 Hz, 1H) 2.76-2.89 (m, 1H) 3.00 (s, 3H) 3.68-3.77 (m, 1H) 3.78 (s, 3H) 3.96-4.09 (m, 1H) 4.20-4.31 (m, 2H) 4.64 (dd, J=8.70, 1.98 Hz, 1H) 5.22 (d, J=11.90 Hz, 1H) 5.72 (d, J=17.40 Hz, 1H) 6.69 (ddd, J=17.40, 10.99, 2.44 Hz, 1H) 7.29 (d, J=7.32 Hz, 1H) 7.32-7.45 (m, 6H) 7.66 (d, J=7.32 Hz, 1H).

Step 3:

Tetrabutylammonium fluoride (0.830 mL, 0.830 mmol) was added to a solution of (2S,4R)-2-methyl 1-(2-(trimethylsilyl)ethyl) 4-methoxy-4-(2'-vinylbiphenyl-4-yl)pyrrolidine-1,2-dicarboxylate (100 mg, 0.208 mmol) in THF (2 mL) at r.t. and stirred at this temperature overnight. The reaction was diluted with EtOAc and washed with water and then brine. The organic layer was collected, dried over MgSO₄, filtered and evaporated to give (2S,4R)-methyl 4-methoxy-4-(2'-vinylbiphenyl-4-yl)pyrrolidine-2-carboxylate (Intermediate 3, 630 mg, 100% yield) which was used directly in next steps with no purification. LCMS: rt=1.14 min. [M+Na]⁺=360; Phenomenex-Luna C-18 (5μ) (3.0×50 min); Solvent A=10% acetonitrile—90% water—0.1% TFA, Solvent B—90% acetonitrile—10% water—0.1% TFA; gradient 0% to 100% solvent B over 2 min. and then hold for 1 min.; 4 mL/min, inj. vol.=5 uL; wavelength=220. ¹H NMR (500 MHz, CHLOROFORM-d) δ ppm 2.51 (dd, J=13.58, 9.61 Hz, 1H) 2.71 (dt, J=13.73, 2.44 Hz, 1H) 2.99 (s, 3H) 3.09 (d, J=12.21 Hz, 1H) 3.30-3.43 (m, 1H) 3.56 (dd, J=12.21, 2.14 Hz, 1H) 3.81 (s, 3H) 3.97 (dd, J=9.77, 2.75 Hz, 1H) 5.21 (dd, J=10.99, 1.22 Hz, 1H) 5.72 (dd, J=17.70, 1.22 Hz, 1H) 6.71 (dd, J=17.70, 10.99 Hz, 1H) 7.27-7.31 (m, 1H) 7.33-7.42 (m, 6H) 7.60-7.72 (m, 1H).

Preparation Intermediate 4:

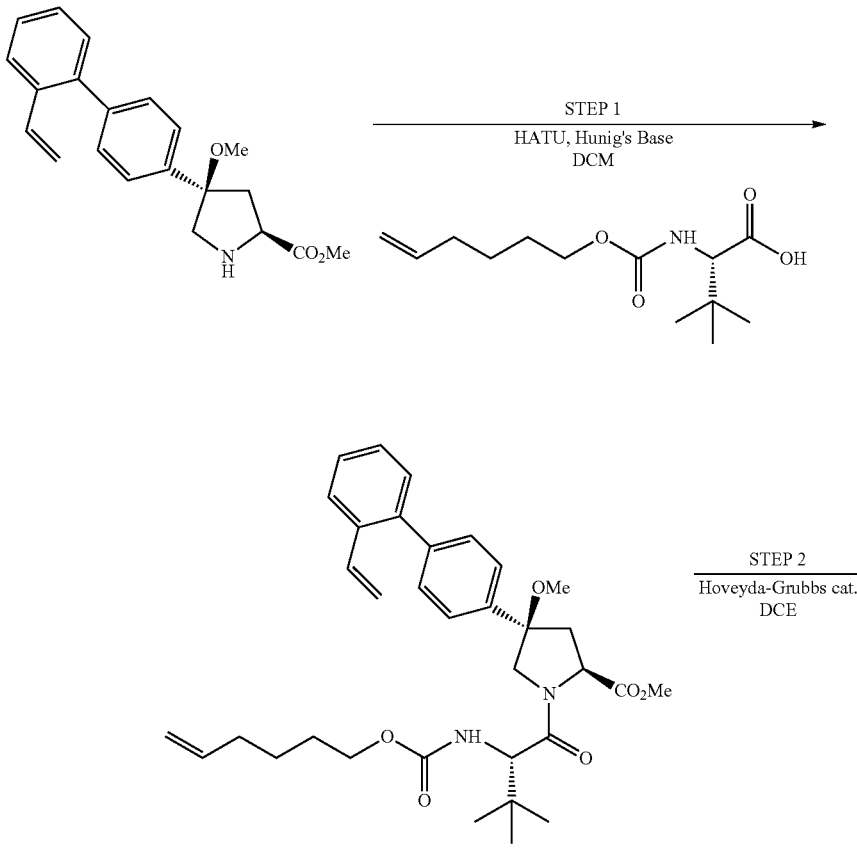

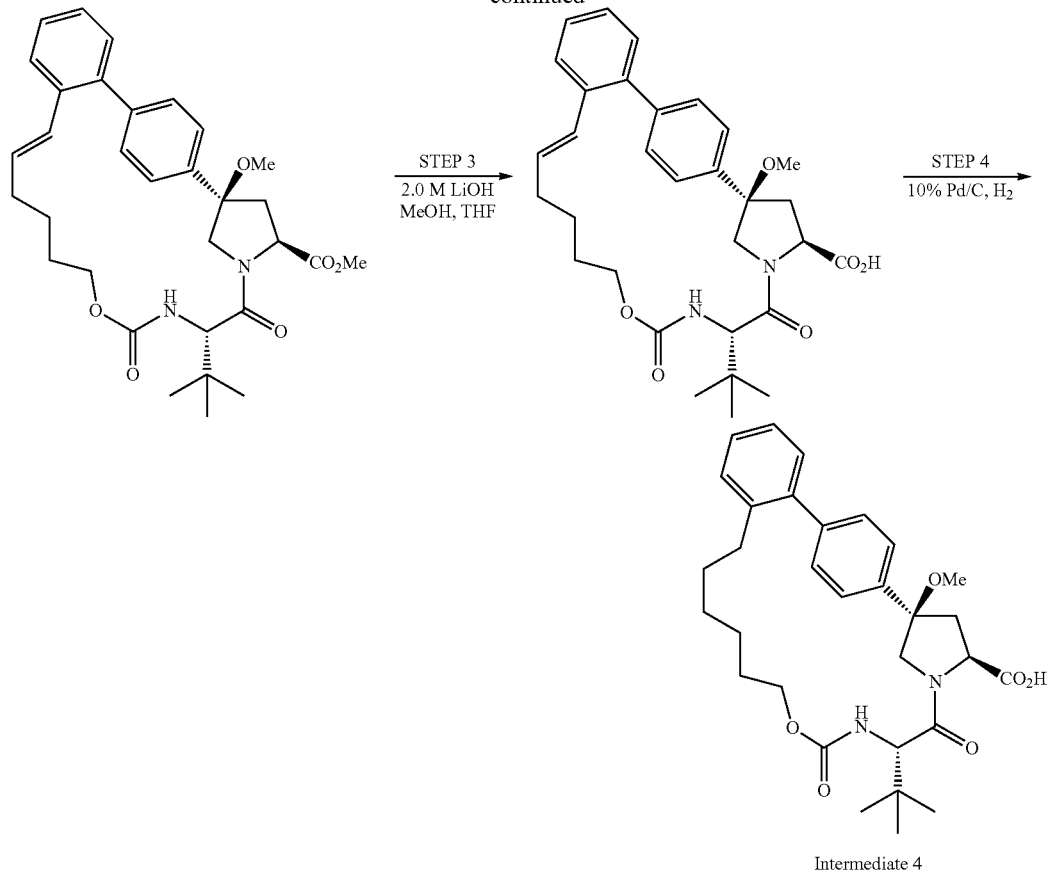

Intermediate 4

Step 1:

HATU (139 mg, 0.365 mmol) was added to a solution of (S)-2-((hex-5-enyloxy)carbonylamino)-3,3-dimethylbutanoic acid (128 mg, 0.498 mmol), DIEA (0.174 mL, 0.996 mmol) and (2S,4R)-methyl 4-methoxy-4-(2'-vinylbiphenyl-4-yl)pyrrolidine-2-carboxylate (112 mg, 0.332 mmol) in DCM (5 mL). The reaction was stirred at r.t. overnight. The reaction was evaporated and purified on the Biotage (10-40% EtOAc in hexanes) to give (2S,4R)-methyl 1-((S)-2-((hex-5-enyloxy)carbonylamino)-3,3-dimethylbutanoyl)-4-methoxy-4-(2'-vinylbiphenyl-4-yl)pyrrolidine-2-carboxylate (151 mg, 79% yield) as a clear oil. LCMS: rt=2.05 min. $[M+Na]^{30}$ =599; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 2:

(2S,4R)-methyl 1-((S)-2-((hex-5-enyloxy)carbonylamino)-3,3-dimethylbutanoyl)-4-methoxy-4-(2'-vinylbiphenyl-4-yl)pyrrolidine-2-carboxylate (151 mg, 0.262 mmol) was dissolved in DCE (26 mL) and bubbled with nitrogen gas for 15 min. Hoveyda-Grubbs catalyst (16 mg, 0.026 mmol) was added and heated in an oil bath at 80° C. for 2 hours and then concentrated on the rotovap. The crude product was purified on the Biotage (10-50% EtOAc in hexanes) to give the product (121 mg, 84% yield) as a white foam. LCMS: rt=1.91 min. $[M+Na]^+$=571; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 3:

2.0M lithium hydroxide (0.33 mL, 0.662 mmol) was added to a solution of the product from Step 2 (121 mg, 0.221 mmol) in THF (2 mL) and methanol (2 mL) at r.t. and stirred overnight. The reaction was diluted with diethyl ether, washed with 1M HCl, and brine. The organic layer was collected, dried over MgSO$_4$, filtered and evaporated to give the crude product. LCMS: rt=1.69 min. $[M+Na]^+$=557; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 4:

10% Palladium on carbon (25 mg, 0.023 mmol) was added to the product from Step 3 (124 mg, 0.232 mmol) in EtOAc (3 mL) and stirred under an atmosphere of hydrogen overnight. The reaction was filtered through a Millipore millex-HV 0.45 um frit and evaporated to give Intermediate 4 (121 mg, 97% yield). LCMS: rt=1.68 min. $[M+Na]^+$=559; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Preparation of Compound 1:

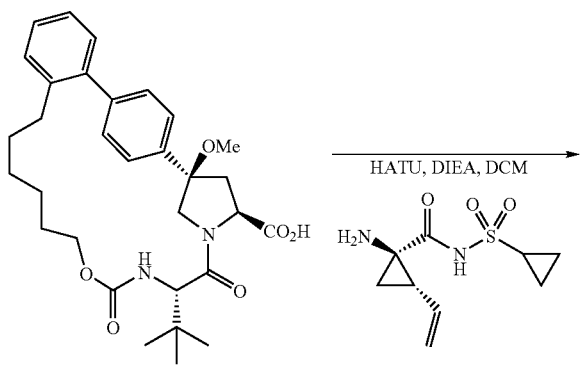

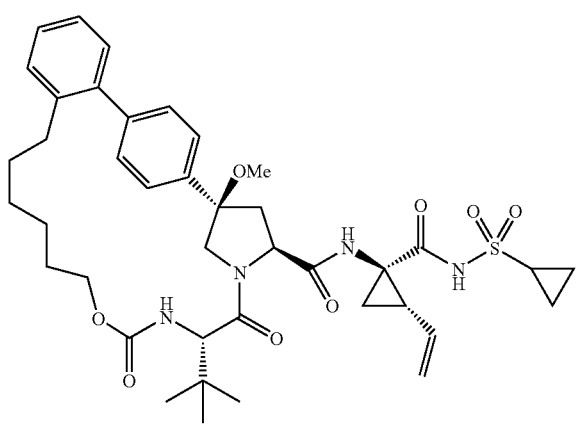

Compound 1

Preparation of Compound 2:

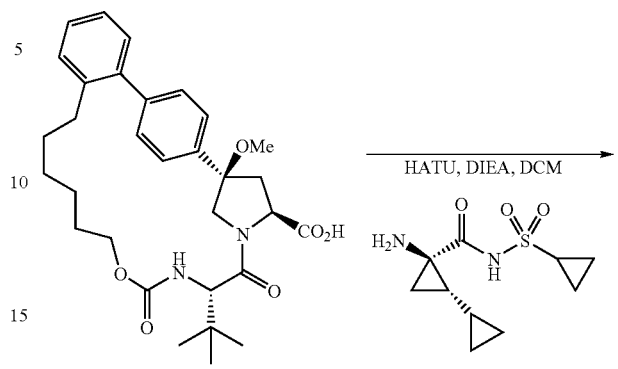

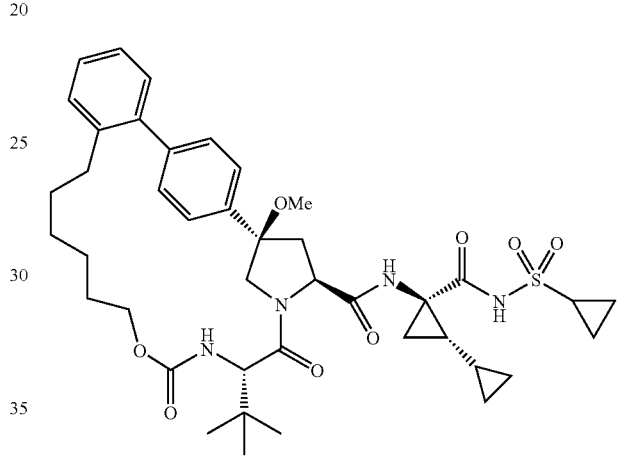

Compound 2

HATU (63 mg, 0.164 mmol) was added to a solution of Intermediate 4 (80 mg, 0.149 mmol), Hunig's base (0.078 mL, 0.447 mmol), and (1R,2S)-1-amino-N-(cyclopropylsulfonyl)-2-vinylcyclopropanecarboxamide, p-toluene sulfonic acid salt (90 mg, 0.224 mmol) in DCM (2 mL). The reaction was stirred at r.t. overnight. The crude product was evaporated and purified by prep HPLC (Sunfire Prep C18 OBD 5u (30× 100 mm); flow=42 mL/min; solvent gradient 70:30 to 5:95 water/acetonitrile (with 10 mM ammonium acetate)) to give Compound 1 (32 mg, 29% yield) as a white solid. LCMS: rt=1.91 min. $[M+Na]^+=771$; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (400 MHz, CHLOROFORM-d) δ ppm 0.94-1.01 (m, 2H) 1.04 (s, 9H) 1.10-1.22 (m, 2H) 1.12-1.23 (m, 1H) 1.12-1.23 (m, 3H) 1.28-1.37 (m, 4H) 1.39-1.50 (m, 2H) 1.95 (t, J=6.78 Hz, 1H) 2.09 (br. s., 1H) 2.51 (hr. s., 1H) 2.61-2.71 (m, 2H) 2.95 (hr. s., 1H) 3.10 (s, 3H) 3.65 (d, J=10.29 Hz, 1H) 3.73-3.87 (m, 1H) 4.05 (d, J=10.29 Hz, 1H) 4.17 (d, J=10.54 Hz, 1H) 4.43 (d, J=9.79 Hz, 1H) 4.48-4.62 (m, 1H) 4.88 (d, J=9.03 Hz, 1H) 5.19 (d, J=8.78 Hz, 1H) 5.31 (d, J=17.32 Hz, 1H) 5.77 (d, J=10.29 Hz, 2H) 7.15-7.34 (m, 5H) 7.34-7.49 (m, 3H).

HATU (32 mg, 0.082 mmol) was added to a solution of Intermediate 4 (40 mg, 0.075 mmol), Hunig's base (0.039 mL, 0.224 mmol) and (1S,2R)-2-amino-N-(cyclopropylsulfonyl)bi(cyclopropane)-2-carboxamide, HCl salt (31 mg, 0.112 mmol) in DCM (1.5 mL). The reaction was stirred at r.t. overnight. The crude product was evaporated and purified by prep HPLC (Sunfire Prep C18 OBD 5u (30×100 mm); flow=42 mL/min; solvent gradient 70:30 to 5:95 water/acetonitrile (with 10 mM ammonium acetate)) to give Compound 2 (26 mg, 44% yield) as a white solid. LCMS: rt=1.94 min. $[M+Na]^+=785$; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220 nm. $^1$H NMR (400 MHz, CHLOROFORM-d) δ ppm 0.33 (d, J=9.29 Hz, 1H) 0.36-0.45 (m, 1H) 0.50-0.67 (m, 2H) 0.75-0.87 (m, 1H) 0.89 (t, J=6.78 Hz, 2H) 1.04 (s, 9H) 1.11-1.21 (m, 4H) 1.21-1.31 (m, 4H) 1.31-1.46 (m, 4H) 1.41-1.52 (m, 1H) 1.79 (dd, J=7.91, 5.65 Hz, 1H) 2.42-2.59 (m, 1H) 2.59-2.68 (m, 2H) 2.68-2.79 (m, 1H) 2.89-3.04 (m, 1H) 3.06 (s, 3H) 3.15 (d, 1H) 3.61 (d, J=10.29 Hz, 1H) 3.75-3.85 (m, 1H) 3.93 (d, 1H) 4.04 (d, J=10.29 Hz, 1H) 4.15 (d, J=10.04 Hz, 1H) 4.40 (d, J=10.29 Hz, 1H) 4.49-4.57 (m, 1H) 7.15-7.34 (m, 5H) 7.34-7.48 (m, 3H).

Preparation of Compound 3:

Preparation of Compound 4:

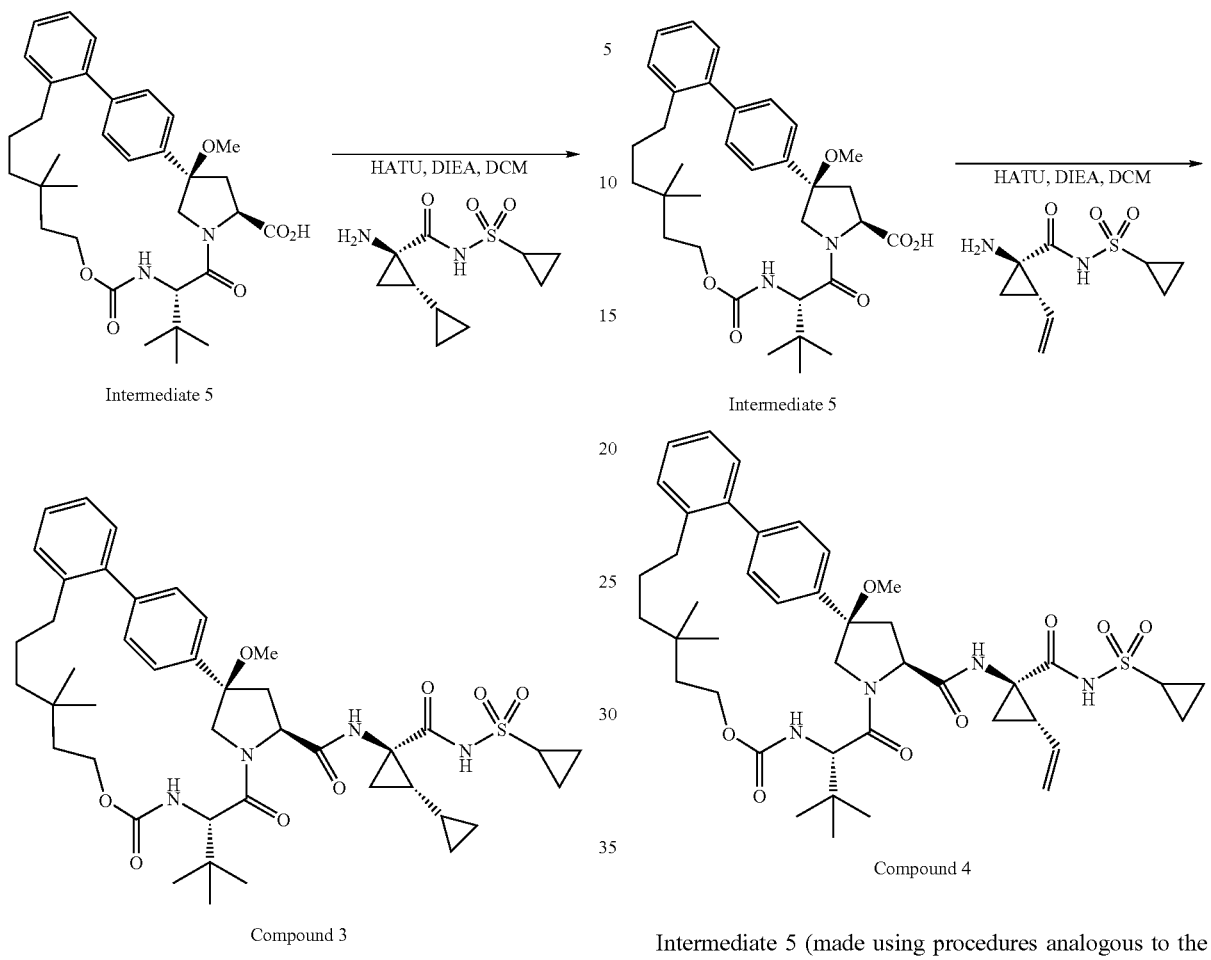

Intermediate 5 (made using procedures analogous to the synthesis of Intermediate 4) (100 mg, 0.177 mmol), DIEA (0.093 mL, 0.531 mmol) and HATU (74 mg, 0.195 mmol) were added to a solution of (1S,2R)-2-amino-N-(cyclopropylsulfonyl)bi(cyclopropane)-2-carboxamide, TFA salt (79 mg, 0.221 mmol) in DCM (2 mL). The reaction was stirred at r.t. for 3 days. The crude product was evaporated and purified by prep HPLC (Sunfire Prep C18 OBD 5u (30×100 mm); flow=42 mL/min; solvent gradient 70:30 to 5:95 water/acetonitrile (with 10 mM ammonium acetate)) to give Compound 3 (66 mg, 0.079 mmol, 45% yield) as a white solid. LCMS: rt=2.05 min. [M+Na]$^+$=813; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220 nm. $^1$H NMR (500 MHz, DMSO-d$_6$) δ ppm 0.15-0.29 (m, 2H) 0.39-0.54 (m, 2H) 0.59-0.72 (m, 2H) 0.79 (s, 3H) 0.81 (s, 3H) 0.90-0.95 (m, 2H) 0.98 (s, 9H) 1.02-1.20 (m, 6H) 1.20-1.33 (m, 2H) 1.46-1.54 (m, 1H) 1.54-1.62 (m, 1H) 2.27-2.39 (m, 1H) 2.40-2.47 (m, 2H) 2.88-2.99 (m, 1H) 3.02 (s, 3H) 3.75 (td, J=10.45, 5.04 Hz, 1H) 3.88 (d, J=10.38 Hz, 1H) 3.99 (t, J=8.24 Hz, 1H) 4.02-4.13 (m, 1H) 4.33 (d, J=9.77 Hz, 1H) 4.40 (d, J=10.68 Hz, 1H) 7.19 (d, 1H) 7.26 (td, J=6.64, 2.90 Hz, 2H) 7.28-7.32 (m, 2H) 7.33-7.39 (m, 4H) 7.54 (d, J=9.77 Hz, 1H) 8.49 (br. s., 1H) 10.35 (s, 1H).

Intermediate 5 (made using procedures analogous to the synthesis of Intermediate 4) (70 mg, 0.124 mmol), DMA (0.065 mL, 0.372 mmol) and HATU (52 mg, 0.136 mmol) was added to a solution of (1R,2S)-1-amino-N-(cyclopropylsulfonyl)-2-vinylcyclopropanecarboxamide, pTSA salt (74.8 mg, 0.186 mmol) in DCM (2 mL). The reaction was stirred at r.t. for 3 days. The crude product was evaporated and purified by prep HPLC (Sunfire Prep C18 OBD 5u (30×100 mm); flow=42 mL/min; solvent gradient 70:30 to 5:95 water/acetonitrile (with 10 mM ammonium acetate)) to give Compound 4 (26 mg, 0.032 mmol, 26% yield) as a white solid. LCMS: rt=2.03 min. [M+Na]$^+$=799; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220 nm. $^1$H NMR (500 MHz, CHLOROFORM-d) δ ppm 0.71 (br. s., 3H) 0.84 (d, J=6.41 Hz, 3H) 0.87-0.95 (m, 1H) 0.98-1.05 (m, 2H) 1.08 (d, J=5.49 Hz, 9H) 1.21 (br. s., 1H) 1.26 (s, 1H) 1.29-1.40 (m, 2H) 1.40-1.49 (m, 2H) 1.94 (dd, J=8.09, 5.95 Hz, 1H) 2.04-2.13 (m, 1H) 2.34-2.45 (m, 1H) 2.52 (br. s., 1H) 2.57-2.67 (m, 2H) 2.69-2.79 (m, 1H) 2.93 (br. s., 1H) 3.14 (s, 3H) 3.20-3.27 (m, 1H) 3.65 (d, J=9.16 Hz, 1H) 3.78-3.91 (m, 2H) 3.92-4.03 (m, 1H) 4.03-4.10 (m, 1H) 4.11-4.20 (m, 1H) 4.23-4.34 (m, 1H) 4.43-4.58 (m, 1H) 4.88 (d, J=8.24 Hz, 1H) 5.09-5.22 (m, 1H) 5.27 (br. s., 1H) 5.64-5.83 (m, 1H) 7.23 (br. s., 1H) 7.28-7.31 (m, 3H) 7.33 (d, J=10.07 Hz, 2H) 7.41-7.50 (m, 2H).

Preparation of Compound 5:

Preparation of Compound 6:

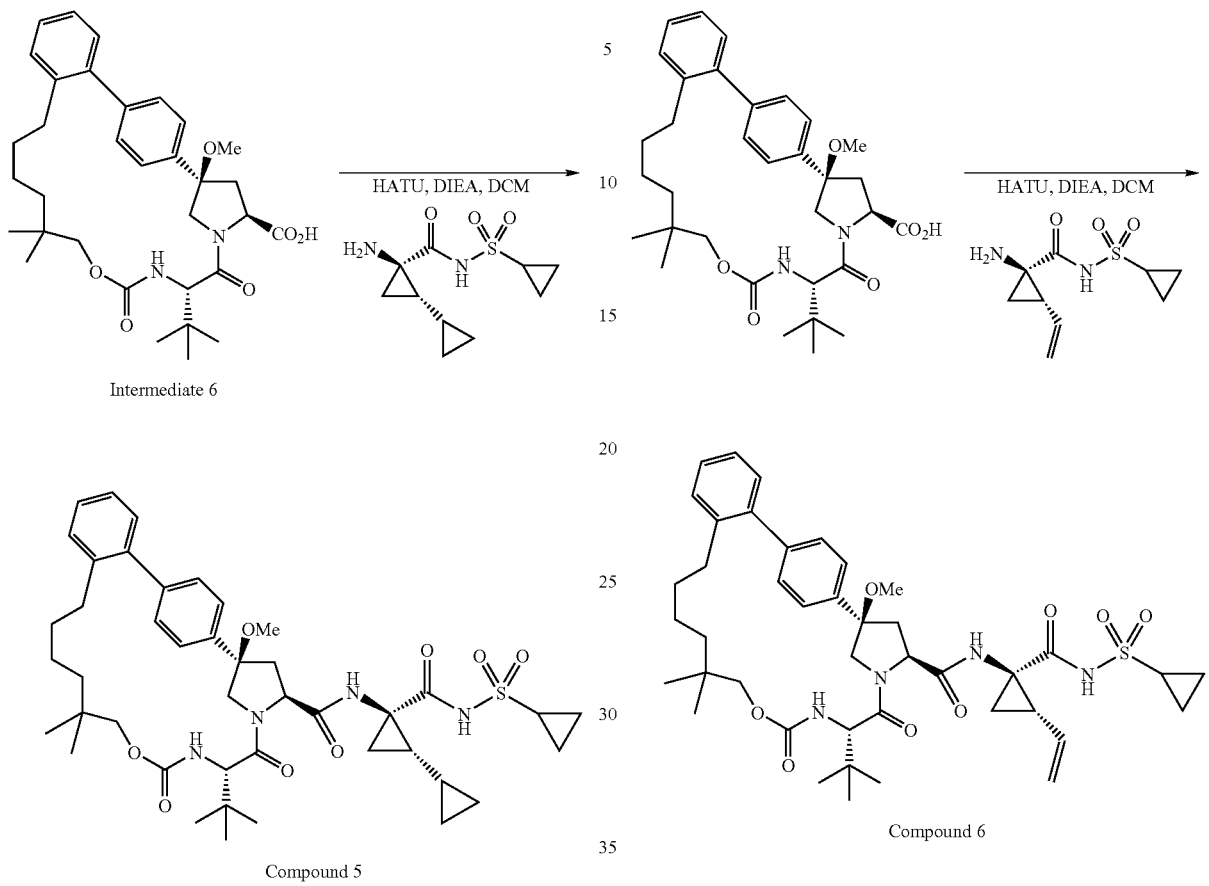

Compound 5

Compound 6

(1S,2R)-2-amino-N-(cyclopropylsulfonyl)bi(cyclopropane)-2-carboxamide, TFA salt (0.111 g, 0.111 mmol), DIEA (0.046 mL, 0.266 mmol) and HATU (37 mg, 0.097 mmol) were added to a solution of Intermediate 6 (made using procedures analogous to the synthesis of Intermediate 4) (50 mg, 0.089 mmol) in DCM (1 mL). The reaction was stirred at r.t. for 3 days. The crude product was evaporated and purified by prep HPLC (Sunfire Prep C18 OBD 5u (30×100 mm); flow=42 mL/min; solvent gradient 70:30 to 5:95 water/acetonitrile (with 10 mM ammonium acetate)) to give Compound 5 (15 mg, 0.017 mmol, 20% yield) as a white solid. LCMS: rt=2.04 min. [M+Na]$^+$=813; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (500 MHz, CHLOROFORM-d) δ ppm 0.25-0.37 (m, 2H) 0.59 (d, J=8.85 Hz, 2H) 0.77 (s, 3H) 0.80 (s, 2H) 0.88 (s, 3H) 1.03 (s, 9H) 1.06 (br. s., 2H) 1.17 (br. s., 2H) 1.28 (dd, J=9.31, 5.65 Hz, 1H) 1.40 (d, J=4.58 Hz, 2H) 1.84 (dd, J=7.93, 5.80 Hz, 1H) 2.41 (br. s., 1H) 2.59-2.69 (m, 1H) 2.69-2.78 (m, 1H) 2.97 (br. s., 1H) 3.11 (s, 3H) 3.17-3.25 (m, 1H) 3.20 (d, J=10.68 Hz, 1H) 3.41 (d, J=10.68 Hz, 1H) 3.67 (s, 1H) 3.85 (d, J=11.60 Hz, 1H) 3.98 (d, J=10.38 Hz, 1H) 4.13 (d, J=10.07 Hz, 1H) 4.27-4.43 (m, 3H) 4.91 (s, 1H) 5.35 (br. s., 1H) 6.81 (s, 1H) 7.19-7.24 (m, 2H) 7.28-7.46 (m, 6H) 9.95 (br. s., 1H).

Intermediate 6 (made using procedures analogous to the synthesis of Intermediate 4) (15 mg, 0.027 mmol), DIEA (0.014 mL, 0.080 mmol) and HATU (11 mg, 0.029 mmol) were added to a solution of (1R,2S)-1-amino-N-(cyclopropylsulfonyl)-2-vinylcyclopropanecarboxamide, pTSA salt (16 mg, 0.040 mmol) in DCM (0.5 mL). The reaction was stirred at r.t. for 3 days. The crude product was evaporated and purified by prep HPLC (Sunfire Prep C18 OBD 5u (30×100 mm); flow=42 mL/min; solvent gradient 70:30 to 5:95 water/acetonitrile (with 10 mM ammonium acetate)) to give Compound 6 (8.5 mg, 0.011 mmol, 40% yield) as a white solid. LCMS: rt=2.03 min, [M+Na]$^+$=799; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (500 MHz, CHLOROFORM-d) δ ppm 0.76 (s, 3H) 0.78 (s, 1H) 0.87 (s, 3H) 0.92 (br. s., 1H) 1.02 (br. s., 4H) 1.03 (s, 9H) 1.14-1.21 (m, 2H) 1.30-1.40 (, 2H) 1.47-1.53 (m, 1H) 1.88-2.01 (m, 1H) 2.05-2.22 (m, 1H) 2.35-2.46 (m, 1H) 2.47-2.56 (m, 1H) 2.56-2.64 (m, 1H) 2.68-2.78 (m, 2H) 2.90 (br. s., 1H) 3.11 (s, 3H) 3.19 (d, J=10.68 Hz, 1H) 3.46 (s, 1H) 3.65 (br. s., 1H) 3.79-4.18 (m, 1H) 4.26-4.38 (m, 2H) 4.41 (d, J=10.38 Hz, 1H) 5.16 (d, J=10.99 Hz, 1H) 5.28 (d, J=17.09 Hz, 1H) 5.47 (br. s., 1H) 6.87 (br. s., 1H) 7.23 (d, J=8.85 Hz, 2H) 7.28 (br. s., 2H) 7.31-7.48 (m, 4H).

Preparation of Compound 7:

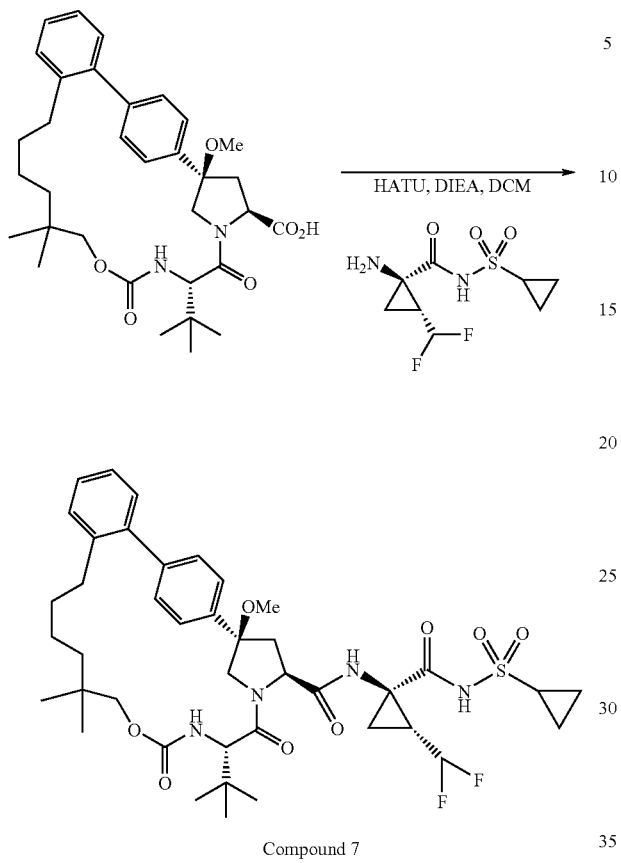

Compound 7

Preparation of Intermediate 7:

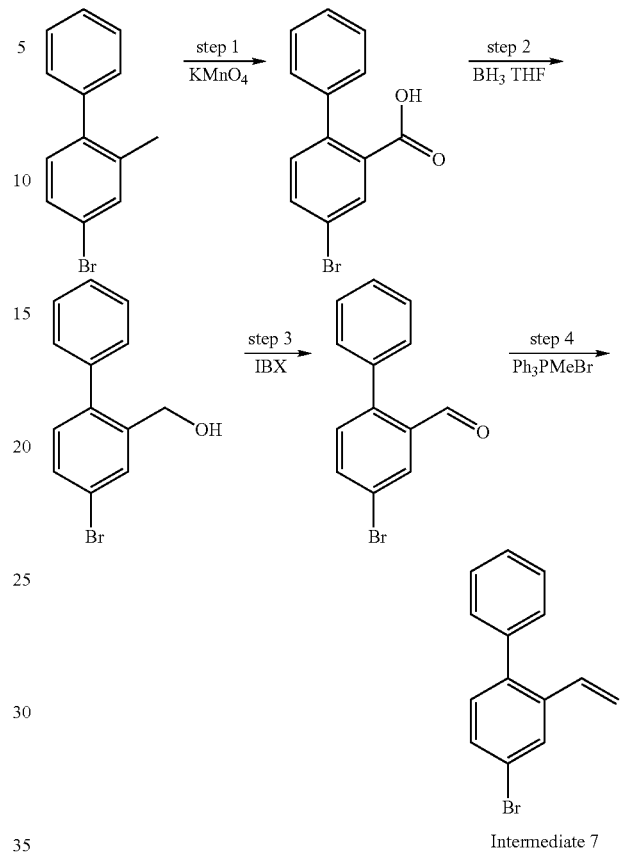

Intermediate 7

Intermediate 6 (made using procedures analogous to the synthesis of Intermediate 4) (15 mg, 0.027 mmol), DIEA (0.014 mL, 0.080 mmol) and HATU (11 mg, 0.029 mmol) were added to a solution of (1R,2R)-1-amino-N-(cyclopropylsulfonyl)-2-(difluoromethyl)cyclopropanecarboxamide, HCl salt (11 mg, 0.040 mmol) in DCM (0.5 mL). The reaction was stirred at r.t. for 3 days. The crude product was evaporated and purified by prep HPLC (Sunfire Prep C18 OBD 5u (30× 100 mm); flow=42 mL/min; solvent gradient 70:30 to 5:95 water/acetonitrile (with 10 mM ammonium acetate)) to give Compound 7 (9 mg, 0.010 mmol, 37% yield) as a white solid. LCMS: rt=2.03 min. [M+Na]$^+$=823; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (500 MHz, CHLOROFORM-d) δ ppm 0.78 (s, 3H) 0.82 (br. s., 2H) 0.90 (s, 3H) 0.98-1.03 (m, 1H) 1.06 (s, 9H) 1.16-1.28 (m, 2H) 1.32-1.48 (m, 3H) 1.63-1.73 (m, 1H) 1.87-1.98 (m, 1H) 2.14 (br, s., 1H) 2.38-2.46 (m, 1H) 2.46-2.56 (m, 1H) 2.64-2.81 (m, 2H) 2.93 (br. s., 1H) 3.12 (s, 3H) 3.22 (d, J=10.07 Hz, 1H) 3.68 (br. s., 1H) 4.02 (d, J=10.99 Hz, 1H) 4.12-4.29 (m, 1H) 4.32-4.40 (m, 1H) 4.40-4.46 (m, 1H) 5.34 (br. s., 1H) 5.76-6.16 (m, 1H) 6.66 (br. s., 1H) 7.16-7.27H) 7.28-7.33 (m, 2H) 7.37 (m, 4H) 7.42 (s, 1H).

Step 1:
4-bromo-2-methylbiphenyl (5 g, 20.23 mmol) was suspended in pyridine (23 mL) and water (35 mL). Potassium permanganate (16 g, 101 mmol) was added portion wise over a period of 20 min. The mixture was refluxed overnight. The reaction mixture was cooled and MnO$_2$ was filtered off. Conc. HCl was added to the filtrate until the product precipitated. The product was extracted with DCM, washed with water and brine, collected, dried (MgSO$_4$), filtered and evaporated to give 4-bromobiphenyl-2-carboxylic acid (5 g, 18.04 mmol, 89% yield) as a white solid. LCMS: rt=1.39 min.; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 2:
4-bromobiphenyl-2-carboxylic acid (5.71 g, 20.61 mmol) was dissolved in THF (50 mL) and cooled to 0° C. 1.0M borane tetrahydrofuran complex (41.2 mL, 41.2 mmol) was added dropwise over 15 min. and allowed to warm up to r.t. overnight. The reaction was diluted with EtOAc and washed with water, sat. ammonium chloride, and then brine. The organic layer was collected, dried over MgSO$_4$, filtered and evaporated to give the crude product. The crude product was purified by flash chromatography on the Biotage (5-35% EtOAc:Hex) to give (4-bromobiphenyl-2-yl)methanol (3.5 g, 13.30 mmol, 65% yield) as a light orange oil. LCMS: rt=1.43 min.; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (400 MHz, CHLOROFORM-d) δ ppm 4.60 (d, J=5.77 Hz, 2H) 7.15 (d, J=8.28 Hz, 1H) 7.29-7.35 (m, 2H) 7.36-7.46 (m, 3H) 7.48 (dd, J=8.28, 2.01 Hz, 1H) 7.75 (d, J=2.01 Hz, 1H).

Step 3:

IBX (7.45 g, 26.6 mmol) was added to (4-bromobiphenyl-2-yl)methanol (3.5 g, 13.30 mmol) in dmso (40 mL) and stirred at 60° C. for 2 hours. The reaction was cooled in an ice bath and diluted with water and diethyl ether. The ether layer was washed with brine, dried over $MgSO_4$, filtered and evaporated to give 4-bromobiphenyl-2-carbaldehyde (3.32 g, 12.71 mmol, 96% yield) as an orange oil. LCMS: rt=1.66 min.; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (400 MHz, CHLOROFORM-d) δ ppm 7.29-7.39 (m, 3H) 7.43-7.58 (m, 3H) 7.76 (dd, j=8.16, 2.13 Hz, 1H) 8.15 (d, J=2.01 Hz, 1H) 9.91 (s, 1H).

Step 4:

Sodium hydride (2.034 g, 50.9 mmol) was added to a solution of methyltriphenylphosphonium bromide (9.1 g, 25.4 mmol) in THF (60 mL). The mixture was stirred at 0° C. for 1 hr. A solution of 4-bromobiphenyl-2-carbaldehyde (3.32 g, 12.71 mmol) in THF (60 mL) was added dropwise at 0° C. The mixture was stirred overnight from 0° C. to r.t. The reaction was filtered and evaporated. The residue was diluted with diethyl ether and washed with water and then brine. The ether layer was dried ($MgSO_4$), filtered and evaporated to give the crude material. The product was purified by flash chromatography on the Biotage (100% Hex) to give 4-bromo-2-vinylbiphenyl (Intermediate 7, 2.5 g, 9.65 mmol, 76% yield) as a light orange liquid. $^1$H NMR (500 MHz, CHLOROFORM-d) δ ppm 5.24 (d, J=11.90 Hz, 1H) 5.71 (d, J=17.40 Hz, 1H) 6.64 (dd, J=17.40, 10.99 Hz, 1H) 7.17 (d, J=8.24 Hz, 1H) 7.29-7.34 (m, 2H) 7.34-7.39 (m, 1H) 7.42 (d, J=7.63 Hz, 2H) 7.45 (dd, J=8.09, 1.98 Hz, 1H) 7.77 (d, J=1.83 Hz, 1H).

Preparation of Intermediate 8:

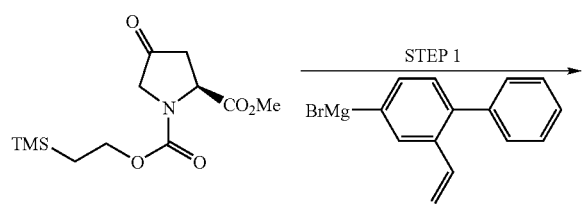

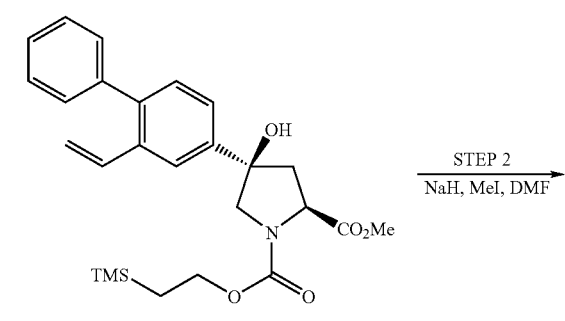

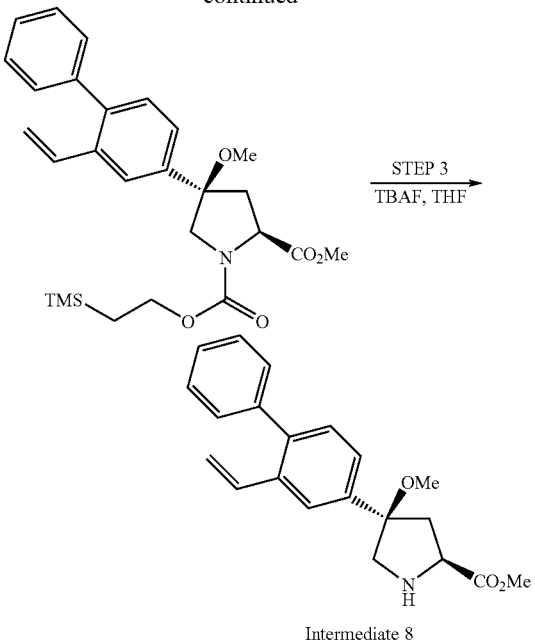

Intermediate 8

Step 1:

(2-vinylbiphenyl-4-yl)magnesium bromide (2.66 g, 9.38 mmol) solution, made by refluxing Intermediate 7 with 1 eq. of magnesium turnings in THF, was added to a solution of (S)-2-methyl 1-(2-(trimethylsilyl)ethyl) 4-oxopyrrolidine-1,2-dicarboxylate (2.7 g, 9.38 mmol) in toluene (75 mL) at 0° C. and stirred for 1 hr and then quenched with sat. $NH_4Cl$ solution. The aqueous layer was extracted with DCM and the combined organics were dried, filtered and evaporated to give crude material. The crude material was purified by flash chromatography on the Biotage (20-33% EtOAc:Hex) to give (2S,4R)-2-methyl 1-(2-(trimethylsilyl)ethyl) 4-hydroxy-4-(2-vinylbiphenyl-4-yl)pyrrolidine-1,2-dicarboxylate (800 mg, 1.711 mmol, 18% yield). LCMS: rt=1.85 min. [M+Na]$^+$=490; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 2:

NaH (60% in oil) (0.239 g, 5.97 mmol) was added to a solution of (2S,4R)-2-methyl 1-(2-(trimethylsilyl)ethyl) 4-hydroxy-4-(2-vinylbiphenyl-4-yl)pyrrolidine-1,2-dicarboxylate (1.55 g, 3.31 mmol) and methyl iodide (0.373 mL, 5.97 mmol) at 0° C. in DMF and stirred at this temperature for 3 hrs. The reaction was then quenched with sat. $NH_4Cl$ solution and ether. The ether layer was washed with brine, dried, filtered and evaporated to give crude material. The crude material was purified by flash chromatography on the Biotage (20-40% EtOAc in hexanes) to give (2S,4R)-2-methyl 1-(2-(trimethylsilyl)ethyl) 4-methoxy-4-(2-vinylbiphenyl-4-yl)pyrrolidine-1,2-dicarboxylate (0.5 g, 1.038 mmol, 31% yield) as a clear oil. LCMS: rt=2.11 min. [M+Na]$^+$=504; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 3:

TBAF (1.0M in THF, 4.1 mL, 4.1 mmol) was added to a solution of (2S,4R)-2-methyl 1-(2-(trimethylsilyl)ethyl) 4-methoxy-4-(2-vinylbiphenyl-4-yl)pyrrolidine-1,2-dicarboxylate (500 mg, 1.038 mmol) in THF (5 mL) and stirred at r.t. overnight. The reaction was diluted with EtOAc and washed with water and then brine. The organic layer was collected, dried over MgSO₄, filtered and evaporated on rotovap to give (2S,4R)-methyl 4-methoxy-4-(2-vinylbiphenyl-4-yl)pyrrolidine-2-carboxylate (Intermediate 8, 360 mg, 1.067 mmol, 100% yield). LCMS: rt=2.03 min. [M-MeOH] =305; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Preparation of Intermediate 9:

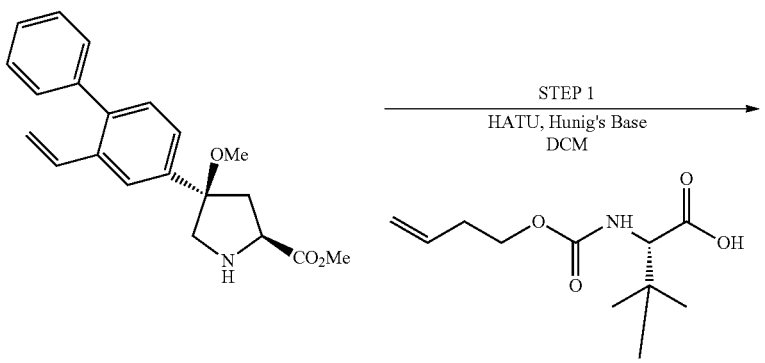

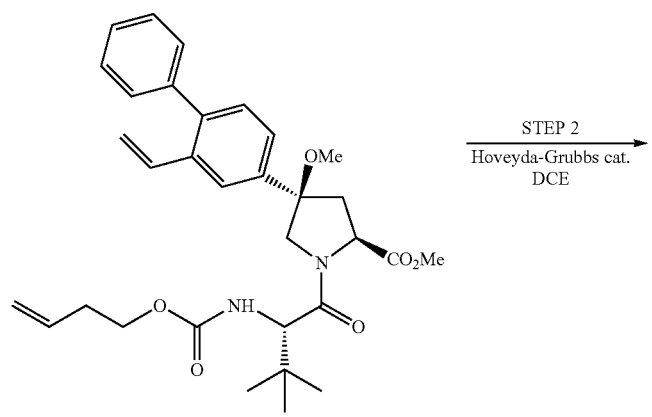

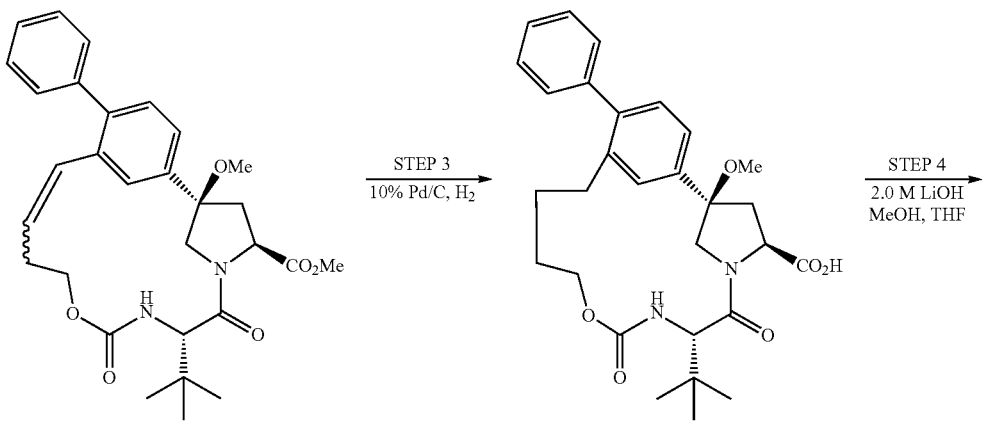

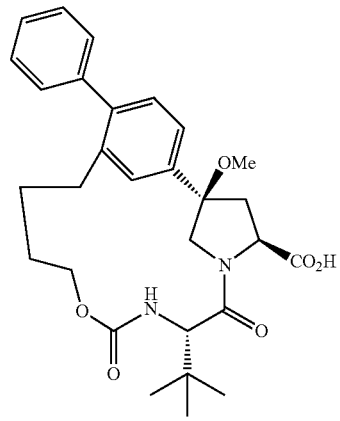

Intermediate 9

Step 1:
(S)-2-((but-3-enyloxy)carbonylamino)-3,3-dimethylbutanoic acid (117 mg, 0.511 mmol), DIEA (0.179 mL, 1.022 mmol) and HATU (143 mg, 0.375 mmol) were added to a solution of (2S,4R)-methyl 4-methoxy-4-(2-vinylbiphenyl-4-yl)pyrrolidine-2-carboxylate (115 mg, 0.341 mmol) in DCM (4 mL). The reaction was stirred at r.t. overnight. The reaction was evaporated and purified by flash chromatography on the Biotage (0-40% EtOAc:Hex) to give (2S,4R)-methyl 1-((S)-2-((but-3-enyloxy)carbonylamino)-3,3-dimethylbutanoyl)-4-methoxy-4-(2-vinylbiphenyl-4-yl)pyrrolidine-2-carboxylate (150 mg, 0.273 mmol, 80% yield) as a white foam. LCMS: rt=1.89 min. [M+Na]$^+$=571; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 2:
(2S,4R)-methyl 1-((S)-2-((but-3-enyloxy)carbonylamino)-3,3-dimethylbutanoyl)-4-methoxy-4-(2-vinylbiphenyl-4-yl)pyrrolidine-2-carboxylate (150 mg, 0.273 mmol) was dissolved in DCE (29 mL) and bubbled with nitrogen gas for 15 min. Hoveyda-Grubbs Catalyst (2nd Generation) (17 mg, 0.027 mmol) was added and heated in an oil bath at 80° C. for 2 hours. The crude product was purified by flash chromatography on the Biotage (10-50% EtOAc/Hex) to give the product (123 mg, 0.236 mmol, 86% yield) as a white foam. LCMS: rt=1.78 min. [M+Na]$^+$=543; Phenomenex-Luna C-18 (5μ) (3.0×50 mm); Solvent A=10% acetonitrile—90% water 0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 3:
The product from Step 2 (123 mg, 0.236 mmol) in ethyl acetate (4 mL) was treated with 10% palladium on carbon (25 mg, 0.024 mmol) and stirred under a balloon of hydrogen overnight. The reaction was filtered through a Millipore millex-HV 0.45 um plug and evaporated to give the product (113 mg, 0.216 mmol, 92% yield). LCMS: rt=1.83 min. [M+Na]$^+$=545; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 4:
2.0M lithium hydroxide solution (0.324 mL, 0.649 mmol) was added to a solution of the product from Step 3 (113 mg, 0.216 mmol) in THF (1 mL) and MeOH (1.000 mL) and was stirred at r.t. overnight. The reaction was diluted with EtOAc and washed with 1M HCl, then brine. The organic layer was collected, dried over MgSO$_4$, filtered and evaporated to give Intermediate 9 (103 mg, 0.203 mmol, 94% yield). LCMS: rt=1.60 min. [M+Na]$^+$=531; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Preparation of Compound 8:

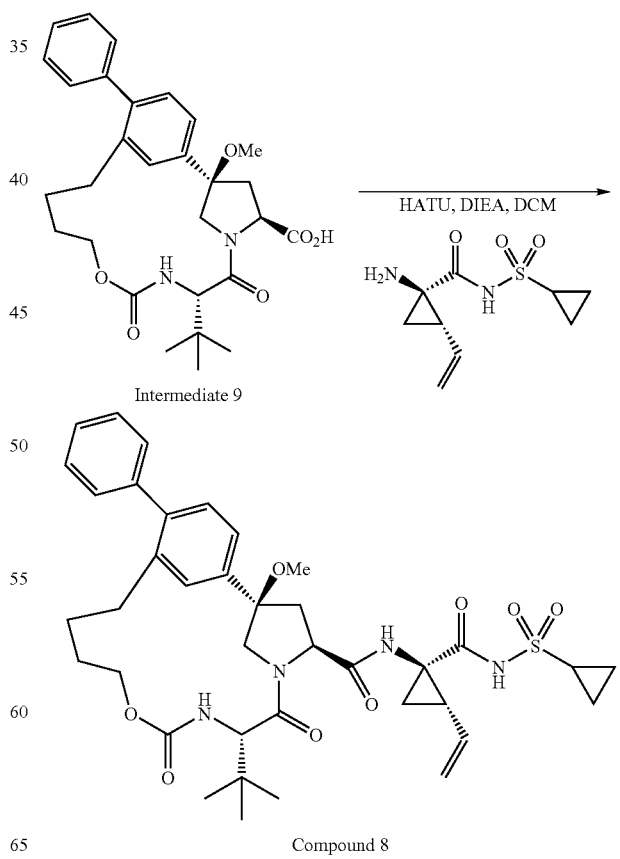

Intermediate 9

Compound 8

Intermediate 9 (15 mg, 0.029 mmol), DIBA (0.015 mL, 0.088 mmol) and HATU (12 mg, 0.032 mmol) were added to a solution of (1R,2S)-1-amino-N-(cyclopropylsulfonyl)-2-vinylcyclopropanecarboxamide, pTSA salt (14 mg, 0.035 mmol) in DCM (1 mL). The reaction was stirred at r.t. overnight. The crude product was evaporated and purified by prep HPLC (Sunfire Prep C18 OBD 5u (30×100 mm); flow=42 mL/min; solvent gradient 70:30 to 5:95 water/acetonitrile (with 10 mM ammonium acetate)) to give Compound 8 (7 mg, 9.29 µmol, 32% yield) as a white solid. LCMS: rt=1.80 min. [M+Na]$^+$=743; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (500 MHz, CHLOROFORM-d) δ ppm 0.99-1.07 (m, 2H) 1.11 (s, 9H) 1.13-1.19 (m, 1H) 1.26-1.34 (m, 2H) 1.35-1.40 (m, 2H) 1.48 (dd, J=8.85, 5.49 Hz, 2H) 1.74-1.86 (m, 1H) 1.96 (dd, J=7.78, 5.65 Hz, 1H) 2.00-2.07 (m, 1H) 2.29-2.42 (m, 1H) 2.60 (s, 1H) 2.86 (br. s., 1H) 2.90-2.97 (m, 1H) 3.12 (s, 3H) 3.67-3.73 (m, 1H) 3.77 (d, J=10.38 Hz, 2H) 4.70 (d, J=10.68 Hz, 1H) 4.95 (s, 1H) 5.01-5.10 (m, 1H) 5.13 (d, J=10.38 Hz, 1H) 5.22 (d, J=17.09 Hz, 1H) 5.53 (br. s., 1H) 5.70-5.88 (m, 1H) 6.44 (br. s., 1H) 7.24 (d, J=7.63 Hz, 2H) 7.28-7.32 (m, 2H) 7.34-7.40 (m, 2H) 7.40-7.45 (m, 2H).

Preparation of Compound 9:

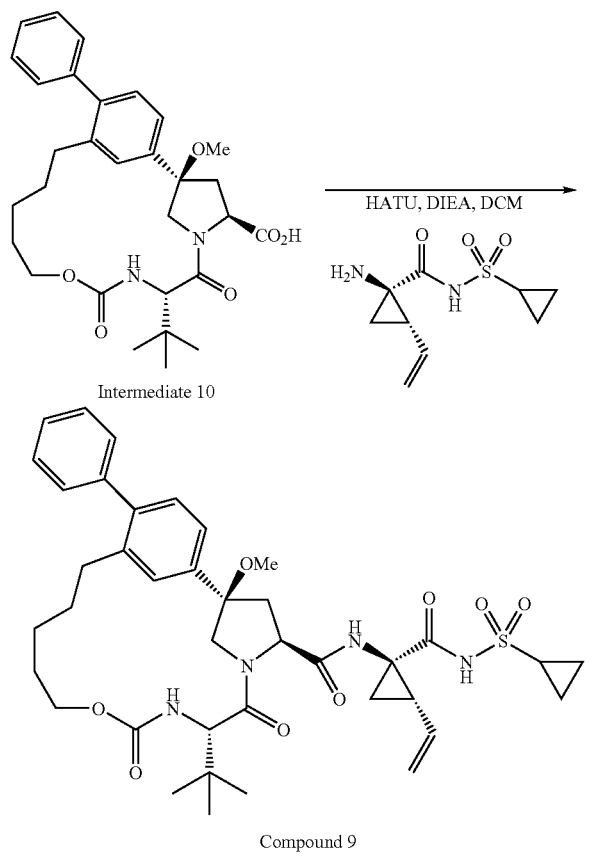

Compound 9

To a solution of (1R,2S)-1-amino-N-(cyclopropylsulfonyl)-2-vinylcyclopropanecarboxamide, pTSA salt (14 mg, 0.034 mmol) in DCM (1 mL) was added Intermediate 10 (prepared using methods analogous to the synthesis of Intermediate 9) (15 mg, 0.029 mmol); DIEA (0.015 mL, 0.086 mmol) and HATU (12 mg, 0.032 mmol). The reaction was stirred at r.t. overnight. The crude product was evaporated and purified by prep HPLC (Sunfire Prep C18 OBD 5u (30×100 mm); flow=42 mL/min; solvent gradient 70:30 to 5:95 water/acetonitrile (with 10 mM ammonium acetate)) to give Compound 9 (8.5 mg, 10.99 µmol, 38% yield) as a white solid. LCMS: rt=1.82 min. [M+Na]$^+$=757; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (500 MHz, CHLOROFORM-d) δ ppm 0.99-1.07 (m, 2H) 1.11 (s, 9H) 1.13-1.19 (m, 1H) 1.26-1.34 (m, 2H) 1.35-1.40 (m, 2H) 1.48 (dd, J=8.85, 5.49 Hz, 2H) 1.74-1.86 (m, 1H) 1.96 (dd, J=7.78, 5.65 Hz, 1H) 2.00-2.07 (m, 1H) 2.29-2.42 (m, 1H) 2.60 (s, 1H) 2.86 (br. s., 1H) 2.90-2.97 (m, 1H) 3.12 (s, 3H) 3.67-3.73 (m, 1H) 3.77 (d, J=10.38 Hz, 2H) 4.70 (d, J=10.68 Hz, 1H) 4.95 (s, 1H) 5.01-5.10 (m, 1H) 5.13 (d, J=10.38 Hz, 1H) 5.22 (d, J=17.09 Hz, 1H) 5.53 (br. s., 1H) 5.70-5.88 (m, 1H) 6.44 (br. s., 1H) 7.24 (d, J=7.63 Hz, 2H) 7.28-7.32 (m, 2H) 7.34-7.40 (m, 2H) 7.40-7.45 (m, 2H).

Preparation of Intermediate 11:

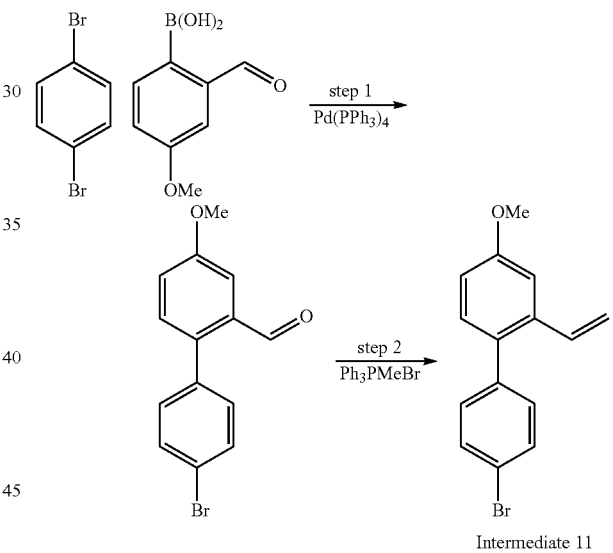

Intermediate 11

Step 1:

A solution of 1,4-dibromobenzene (5.11 g, 21.67 mmol), potassium carbonate (6.91 g, 50.0 mmol) and 2-formyl-4-methoxyphenylboronic acid (3 g, 16.67 mmol) in DME (75 mL) and water (15 mL) (in a pressure vessel) was sparged with nitrogen for 15 min. Pd(Ph$_3$P)$_4$ (0.578 g, 0.500 mmol) was added and then the reaction was heated to 90° C. overnight. The reaction was cooled to r.t. and evaporated on rotovap. The residue was diluted with EtOAc and washed with water then brine, dried over MgSO$_4$, filtered and evaporated to give the crude material. The crude material was purified by flash chromatography on the Biotage (5-15% EtOAc:Hex) to give 4'-bromo-4-methoxybiphenyl-2-carbaldehyde (2.72 g, 9.34 mmol, 56% yield) as a white solid. $^1$H NMR (500 MHz, CHLOROFORM-d) δ ppm 3.91 (s, 3H) 7.18-7.26 (m, 3H) 7.34 (d, J=824 Hz, 1H) 7.52 (d, J=2.75 Hz, 1H) 7.54-7.70 (m, 2H) 9.94 (s, 1H).

Step 2:

Sodium hydride (60% in oil, 1.5 g, 37.4 mmol) was added to a solution of methyltriphenylphosphonium bromide (6.67 g, 18.69 mmol) in THF (30 mL). The mixture was stirred at 0° C. for 1 hr. A solution of 4'-bromo-4-methoxybiphenyl-2-carbaldehyde (2.72 g, 9.34 mmol) in THF (30 mL) was added dropwise at 0° C. The mixture was stirred overnight from 0° C. to r.t. The reaction was filtered and evaporated. The residue was diluted with diethyl ether and washed with water and brine. The ether layer was collected, dried (MgSO$_4$), filtered and evaporated to give the crude material. The crude material was purified by flash chromatography on the Biotage (5-15% EtOAc:Hex) to give 4'-bromo-4-methoxy-2-vinylbiphenyl (Intermediate 11, 2.35 g, 8.13 mmol, 87% yield) as a clear oil. $^1$H NMR (400 MHz, CHLOROFORM-d) δ ppm 3.88 (s, 3H) 5.23 (dd, J=10.92, 1.13 Hz, 1H) 5.70 (dd, J=17.44, 1.13 Hz, 1H) 6.66 (dd, J=17.44, 10.92 Hz, 1H) 6.90 (dd, J=8.41, 2.63 Hz, 1H) 7.16 (d, J=2.51 Hz, 1H) 7.17-7.22 (m, 3H) 7.49-7.57 (m, 2H).

Compound 10:

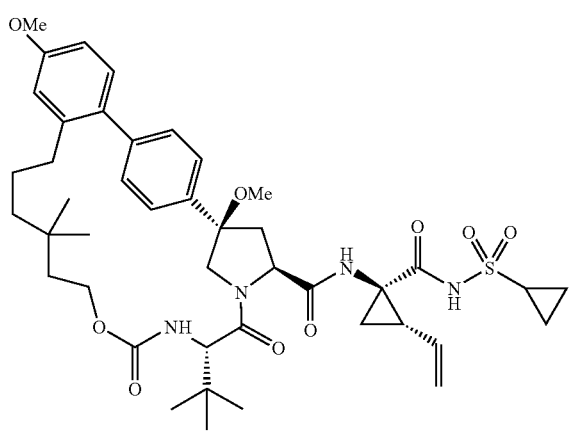

Compound 10

Compound 10 was prepared using procedures analogous to the preparation of Compound 4. LCMS: rt=1.99 min. [M+Na]$^+$=829; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj, vol.=5 uL; wavelength=220. $^1$H NMR (500 MHz, CHLOROFORM-d) δ ppm 0.71 (br. S., 3H) 0.79-0.91 (m, 3H) 0.92-1.00 (m, 2H) 1.09 (s, 9H) 1.21 (d, J=8.24 Hz, 1H) 1.31-1.39 (m, 3H) 1.42 (br. S., 2H) 1.93 (t, J=6.87 Hz, 1H) 2.07 (q, J=8.55 Hz, 1H) 2.34-2.44 (m, 1H) 2.50 (br. S., 1H) 2.54-2.66 (m, 1H) 2.67-2.77 (m, 1H) 2.85-2.99 (m, 1H) 3.10 (s, 2H) 3.16 (s, 2H) 3.18-3.27 (m, 1H) 3.64 (d, J=10.68 Hz, 1H) 3.85 (s, 3H) 3.92-4.02 (m, 1H) 4.04-4.14 (m, 1H) 4.17 (d, J=10.38 Hz, 1H) 4.25-4.34 (m, 1H) 4.45-4.58 (m, 1H) 4.87 (d, J=8.55 Hz, 1H) 5.08-5.21 (m, 1H) 5.21-5.34 (m, 1H) 5.54 (d, J=8.85 Hz, 1H) 5.64-5.83 (m, 1H) 6.75-6.90 (m, 2H) 7.18 (dd, J=18.31, 8.55 Hz, 2H) 7.28-7.33 (m, 2H) 7.36-7.46 (m, 2H) 9.92 (br. S., 1H).

Compound 11:

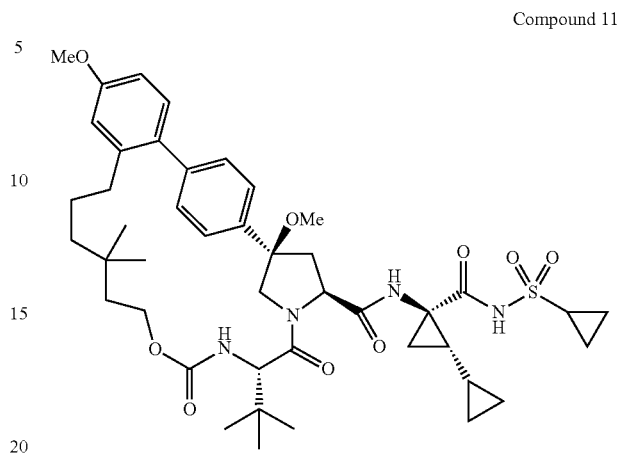

Compound 11

Compound 11 was made using procedures analogous to the preparation of Compound 3. LCMS: rt=2.02 min, [M+Na]$^+$=843; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj, vol.=5 uL; wavelength=220. $^1$H NMR (500 MHz, CHLOROFORM-d) δ ppm 0.30 (br. s., 2H) 0.50-0.62 (m, 2H) 0.69 (br. s., 3H) 0.81 (d, J=9.16 Hz, 6H) 0.91-1.01 (m, 3H) 1.05 (s, 9H) 1.09-1.22 (m, 2H) 1.10-1.15 (m, 1H) 1.32-1.40 (m, 2H) 1.41-1.48 (m, 1H) 1.77 (br. s., 1H) 2.42-2.62 (m, 4H) 3.03 (s, 2H) 3.11 (s, 1H) 3.84 (s, 3H) 3.85-3.93 (m, 2H) 4.40-4.21 (m, 2H) 4.38-4.51 (m, 1H) 6.67-6.86 (m, 2H) 7.06-7.21 (m, 1H) 7.25-7.31 (m, 5H) 7.39 (br. s., 2H) 9.91 (br. s., 1H).

Compound 12:

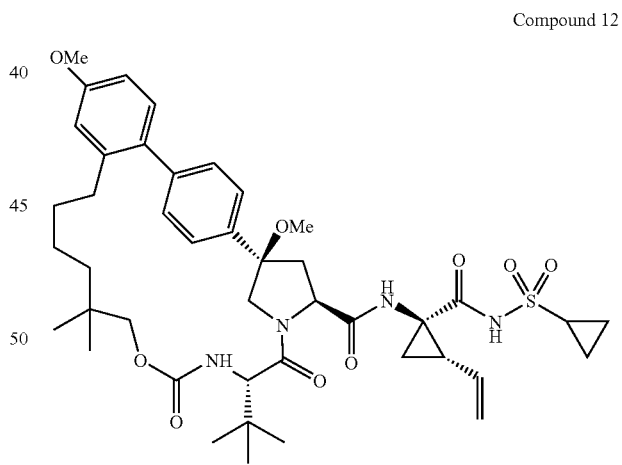

Compound 12

Compound 12 was made using procedures analogous to the preparation of Compound 7. LCMS: rt=1.98 min. [M+Na]$^+$=829; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj, vol.=5 uL; wavelength=220. $^1$H NMR (500 MHz, CHLOROFORM-d) δ ppm 0.77 (s, 3H) 0.88 (s, 3H) 1.00-1.01 (m, 2H) 1.04 (s, 9H) 1.16-1.24 (m, 2H) 1.16-1.23 (m, 2H) 1.33-1.40 (m, 2H) 1.52 (dd, J=9.46, 5.80 Hz, 1H) 1.88-2.05 (m, 1H) 2.05-2.23 (m, 1H) 2.32-2.43 (m, 1H) 2.53-2.63 (m, 1H) 2.64-2.76 (m, 1H) 2.79 (dd, J=12.82, 7.02 Hz, 1H) 2.89-3.00 (m, 1H) 3.11 (s, 3H) 3.15 (s, 1H) 3.20 (d, J=10.38 Hz, 1H) 3.58-3.73 (m, 1H) 3.86 (s, 3H) 4.00 (d, J=10.38 Hz, 1H) 4.29-4.39 (m, 2H) 4.42 (d, J=10.07 Hz, 1H) 5.15-5.24 (m, 1H) 5.27-5.38 (m, 1H) 5.58-5.69 (m, 1H) 5.75-5.86 (m, 1H) 6.76-6.86 (m, 1H) 6.81 (s, 1H) 6.99 (br. s., 1H) 7.16 (d, J=8.55 Hz, 1H) 7.30 (s, 1H) 7.32 (s, 1H) 7.38 (d, J=8.24 Hz, 2H) 7.41-7.45 (m, 1H) 9.85 (br. s., 1H).

Preparation of Compound 13:

Compound 13

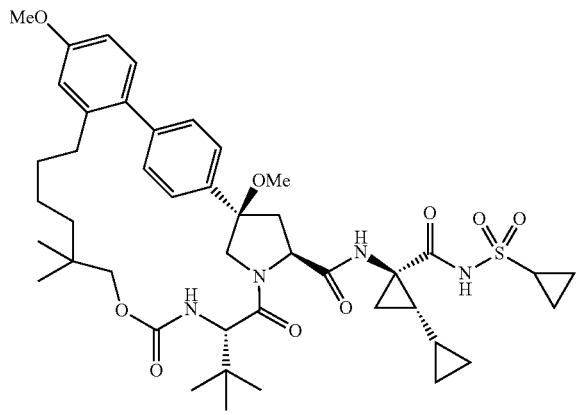

Compound 13 was made using procedures analogous to the preparation of Compound 5. LCMS: rt=2.02 min. [M+Na]$^+$=843; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220. $^1$H NMR (500 MHz, CHLOROFORM-d) δ ppm 0.24-0.45 (m, 2H) 0.51-0.65 (m, 2H) 0.78 (s, 3H) 0.78-0.82 (m, 2H) 0.88 (s, 3H) 0.96-1.02 (m, 2) 1.01-1.05 (m, 9H) 1.08-1.21 (m, 2H) 1.27 (dd, J=9.46, 5.80 Hz, 1H) 1.34-1.45 (m, 2H) 1.84 (dd, J=7.93, 6.10 Hz, 1H) 2.32-2.55 (m, 1H) 2.56-2.68 (m, 1H) 2.68-2.80 (m, 1H) 2.92-3.05 (m, 1H) 3.10 (s, 3H) 3.21 (d, J=10.38 Hz, 1H) 3.86 (s, 3H) 3.94-4.17 (m, 1H) 4.22-4.37 (m, 2H) 4.41 (d, J=10.07 Hz, 1H) 4.78-5.41 (m, 2H) 5.34 (br. s., 1H) 6.76-6.86 (m, 3H) 7.16 (d, J=8.55 Hz, 1H) 7.21-7.27 (m, 2H) 7.28-7.44 (m, 5H) 9.77 (br. s, 1H).

Preparation of Compound 14

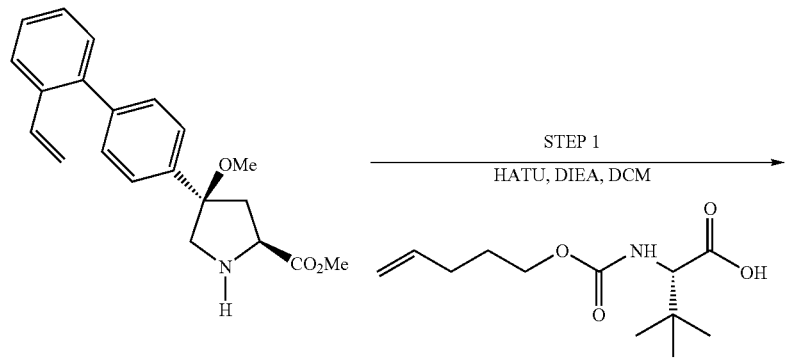

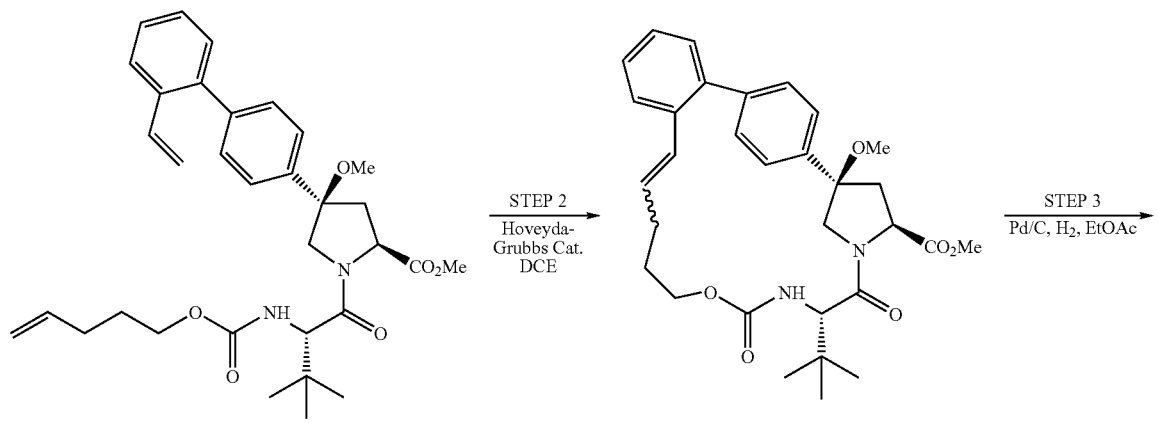

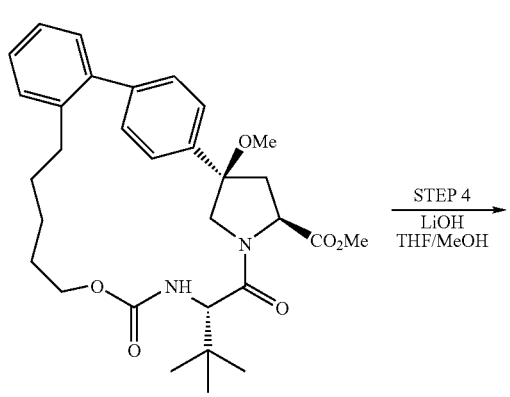

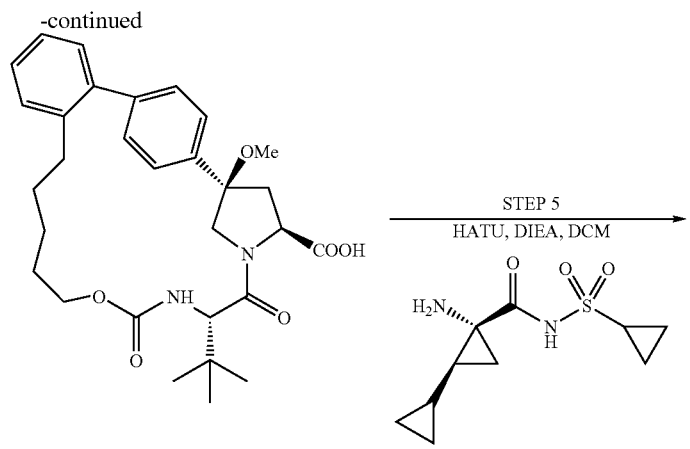

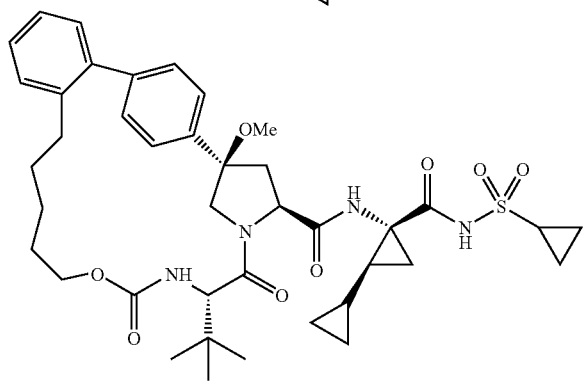

Compound 14

Step 1:

HATU (248 mg, 0.652 mmol) was added to a solution of (2S,4R)-methyl 4-methoxy-4-(2'-vinylbiphenyl-4-yl)pyrrolidine-2-carboxylate (200 mg, 0.593 mmol), (S)-3,3-dimethyl-2-((pent-4-enyloxy)carbonylamino)butanoic acid (180 mg, 0.741 mmol) and DIEA (0.311 mL, 1.778 mmol) in DCM (8 mL) and stirred at r.t. 60 hours. The reaction was evaporated and purified on the Biotage (10-40% EtOAc:Hex) to give the product (2S,4R)-methyl 1-((S)-3,3-dimethyl-2-((pent-4-enyloxy)carbonylamino)butanoyl)-4-methoxy-4-(2'-vinylbiphenyl-4-yl)pyrrolidine-2-carboxylate (251 mg, 0.446 mmol, 75% yield) as white solid. $^1$H NMR (400 MHz, CHLOROFORM-d) δ ppm 0.96-1.00 (m, 1H) 1.04-1.10 (m, 1H) 1.11-1.21 (m, 7H) 1.64-1.79 (m, 2H) 2.06-2.20 (m, 2H) 2.52 (dd, J=13.30, 8.78 Hz, 1H) 2.83-3.04 (m, 4H) 3.72-3.82 (m, 3H) 3.96-4.12 (m, 3H) 4.15-4.21 (m, 1H) 4.31-4.41 (m, 1H) 4.86-5.10 (m, 3H) 5.19-5.30 (m, 1H) 5.41 (d, J=9.79 Hz, 1H) 5.67-5.87 (m, 2H) 6.61-6.76 (m, 1H) 7.28-7.44 (m, 7H) 7.61-7.71 (m, 1H). LCMS: r.t.=2.18 min., [M+H]$^+$=563 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 2:

A solution of (2S,4R)-methyl 1-((S)-3,3-dimethyl-2-((pent-4-enyloxy)carbonylamino)butanoyl)-4-methoxy-4-(2'-vinylbiphenyl-4-yl)pyrrolidine-2-carboxylate (251 mg, 0.446 mmol) in DCE (100 mL) was sparged with nitrogen for 30 min. and then Hoveyda-Grubbs Catalyst (2nd Generation) (28 mg, 0.045 mmol) was added and the reaction sealed and heated to 100° C. for 18 hours. The reaction was concentrated to give crude material. The crude material was purified by flash chromatography on the Biotage (10-40% EtOAc in hexanes) to give the product (196 mg, 0.367 mmol, 82% yield) as white solid. $^1$H NMR (400 MHz, CHLOROFORM-d) δ ppm 1.07 (s, 9H) 1.63 (dd, J=12.17, 8.66 Hz, 1H) 1.88-2.02 (m, 1H) 2.20-2.30 (m, 2H) 2.33 (dd, J=12.42, 10.92 Hz, 1H) 3.05 (s, 3H) 3.07-3.16 (m, 1H) 3.72 (d, J=10.54 Hz, 1H) 3.76-3.81 (m, 3H) 3.91 (dt, J=10.35, 3.73 Hz, 1H) 4.20-4.30 (m, 1H) 4.37 (dd, J=10.79, 8.03 Hz, 1H) 4.55 (d, J=9.79 Hz, 1H) 4.87 (d, J=10.54 Hz, 1H) 5.34 (d, J=9.79 Hz, 1H) 5.96-6.06 (m, 1H) 6.34 (d, J=15.81 Hz, 1H) 7.29-7.36 (m, 3H) 7.39-7.46 (m, 2H) 7.48-7.58 (m, 3H). LCMS: r.t.=2.13 min., [M+H]$^+$=535 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 3:

A solution of the product from Step 2 (196 mg, 0.367 mmol) and 10% Pd/C (39 mg, 0.037 mmol) in EtOAc (10 mL) was stirred under an atmosphere of hydrogen for 16 hours. The reaction was filtered through a nylon frit and concentrated to give crude product (194 mg, 0.361 mmol, 99% yield) as a white solid. LCMS: r.t.=2.08 min., [M+H]$^+$=537 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 4:

2.0 M lithium hydroxide (0.90 mL, 1.80 mmol) was added, to a solution of the product from Step 3 (194 mg, 0.361 mmol)

in THF (3.00 mL) and MeOH (3 mL) and stirred for 3 hours. The reaction Was diluted with ether and 1.0 M HCl. The organic layer was dried, filtered and evaporated to give the crude product (180 mg, 0.344 mmol, 95% yield). LCMS: r.t.=1.85 min., [M+H]$^+$=523 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 5:

HATU (98 mg, 0.258 mmol) was added to a solution of (1S,2R)-2-amino-N-(cyclopropylsulfonyl)bi(cyclopropane)-2-carboxamide, HCl salt (58 mg, 0.207 mmol), the product from Step 4 (90 mg, 0.172 mmol) and Hunig's base (0.090 mL, 0.517 mmol) in dichloromethane (5 mL) and stirred at r.t. for 16 hours. The reaction was concentrated and purified by HPLC (Xbridge C18 10u (30×100 mm); flow=42 ml/min; solvent gradient=95:5 to 5:95 water/acetonitrile (with 10 mM ammonium acetate)). The product fractions were concentrated to give Compound 14 (40 mg, 0.053 mmol, 31% yield) as white solid. $^1$H NMR (400 MHz, MeOD) δ ppm 0.27-0.39 (m, 2H) 0.48-0.62 (m, 2H) 0.81-0.93 (m, 1H) 1.03 (s, 9H) 1.06-1.21 (m, 6H) 1.22-1.30 (m, 3H) 1.41 (br. s., 2H) 1.51 (br. s., 2H) 1.76 (dd, J=8.03, 5.52 Hz, 1H) 2.28-2.38 (m, 1H) 2.43-2.55 (m, 2H) 2.93-3.02 (m, 2H) 3.05 (s, 3H) 3.59 (br. s., 1H) 3.91 (d, J=10.29 Hz, 1H) 4.26-4.41 (m, 3H) 4.45 (d, J=10.04 Hz, 1H) 7.15-7.25 (m, 2H) 7.28 (d, J=3.51 Hz, 2H) 7.34 (m, J=8.03 Hz, 2H) 7.56 (m, J=8.03 Hz, 2H). LCMS: r.t.=1.99 min., [M+H]$^+$=749 Phenomenex. Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Preparation of Compound 15

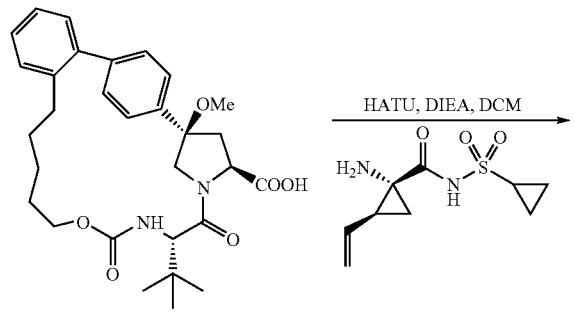

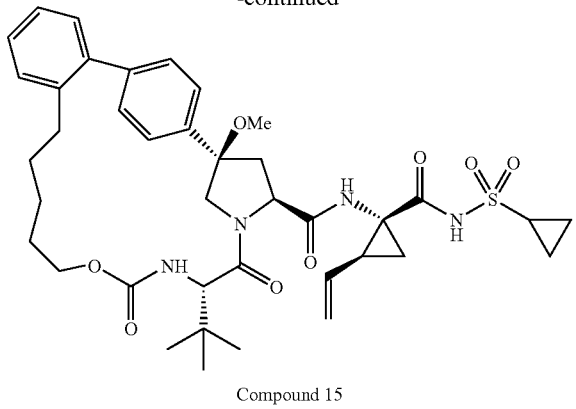

Compound 15

HATU (98 mg, 0.258 mmol) was added to a solution of (1R,2S)-1-amino-N-(cyclopropylsulfonyl)-2-vinylcyclopropanecarboxamide, TsOH salt (83 mg, 0.207 mmol), the product from Step 4 of the preparation of compound 14 (90 mg, 0.172 mmol) and Hunig's base (0.090 mL, 0.517 mmol) in dichloromethane (5 mL) and stirred at r.t. for 16 hours. The reaction was concentrated and purified by HPLC (Xbridge C18 10u (30×100 mm); flow=42 ml/min; solvent gradient=95:5 to 5:95 water/acetonitrile (with 10 mM ammonium acetate)). The product fractions were concentrated to give Compound 15 (676 mg, 0.090 mmol, 52% yield) as white solid. $^1$H NMR (400 MHz, MeOD) δ ppm 0.99-1.11 (m, 11H) 1.11-1.27 (m, 4H) 1.30-1.55 (m, 5H) 1.88 (dd, J=8.03, 5.52 Hz, 1H) 2.16-2.27 (m, 1H) 2.37 (dd, J=12.42, 9.41 Hz, 1H) 2.43-2.58 (m, 2H) 2.88-3.05 (m, 2H) 3.07 (s, 3H) 3.59 (t, J=10.54 Hz, 1H) 3.93 (d, J=10.29 Hz, 1H) 4.30-4.39 (m, 2H) 4.43 (d, J=10.54 Hz, 1H) 5.12 (dd, J=10.29, 1.76 Hz, 1H) 5.29 (dd, J=17.19, 1.38 Hz, 1H) 5.78 (ddd, J=17.19, 10.29, 8.91 Hz, 1H) 7.16-7.26 (m, 2H) 7.28 (d, J=3.26 Hz, 2H) 7.35 (d, J=8.03 Hz, 2H) 7.58 (d, J=8.03 Hz, 2H). LCMS: r.t.=1.97 min., [M+H]$^+$=735 Phenomenex Luna 510 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol. 10 ul; wavelength=220 nm.

Preparation of Compound 16

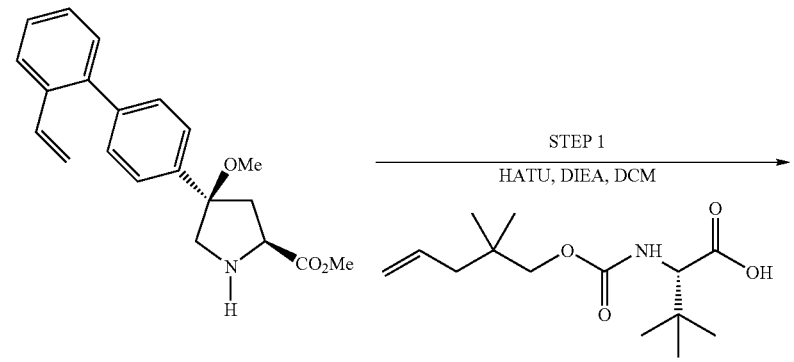

-continued
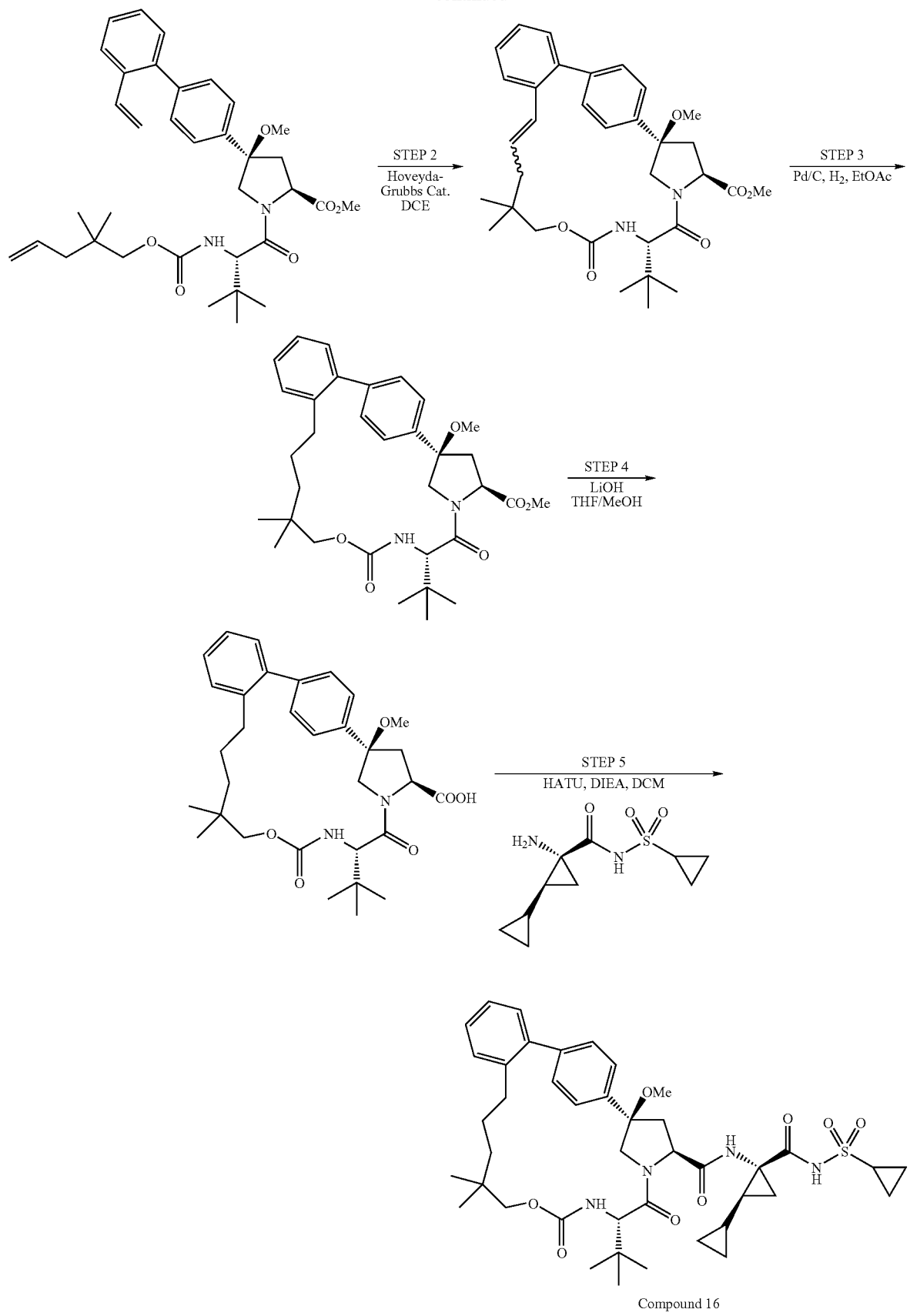
Compound 16

Step 1:

HATU (248 mg, 0.652 mmol) was added to a solution of, (2S,4R)-methyl 4-methoxy-4-(2'-vinylbiphenyl-4-yl)pyrrolidine-2-carboxylate (200 mg, 0.593 mmol), (S)-2-((2,2-dimethylpent-4-enyloxy)carbonylamino)-3,3-dimethylbutanoic acid (201 mg, 0.741 mmol) and DIEA (0.311 mL, 1.778 mmol) in DCM (8 mL) and stirred at r.t. 60 hours. The reaction was evaporated and purified on the Biotage (10-40% EtOAc:Hex) to give (2S,4R)-methyl 1-((S)-2-((2,2-dimethylpent-4-enyloxy)carbonylamino)-3,3-dimethylbutanoyl)-4-methoxy-4-(2'-vinylbiphenyl-4-yl)pyrrolidine-2-carboxylate (235 mg, 0.398 mmol, 67% yield) as white solid. $^1$H NMR (400 MHz, CHLOROFORM-d) δ ppm 0.83-0.94 (m, 6H) 0.97-1.02 (m, 1H) 1.06-1.10 (m, 1H) 1.12-1.19 (m, 7H) 1.95-2.07 (m, 2H) 2.46-2.59 (m, 1H) 2.88 (d, J=12.80 Hz, 1H) 2.92-3.03 (m, 3H) 3.65-3.74 (m, 1H) 3.74-3.79 (m, 3H) 3.79-3.86 (m, 1H) 4.00-4.09 (m, 1H) 4.14-4.21 (m, 1H) 4.31-4.42 (m, 1H) 4.85-4.92 (m, 1H) 4.95-5.09 (m, 2H) 5.17-5.26 (m, 1H) 5.38-5.49 (m, 1H) 5.67-5.84 (m, 2H) 6.60-6.75 (m, 1H) 7.25-7.30 (m, 1H) 7.30-7.42 (m, 6H) 7.61-7.68 (m, 1H). LCMS: r.t.=2.25 min., [M+H]$^+$=591 Phenomenex Luna S10 (3×50 mm); Solvent A=95% water 5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 2:

A solution of (2S,4R)-methyl 1-(S)-2-((2,2-dimethylpent-4-enyloxy)carbonylamino)-3,3-dimethylbutanoyl)-4-methoxy-4-(2'-vinylbiphenyl-4-yl)pyrrolidine-2-carboxylate (235 mg, 0.398 mmol) in DCE (100 mL) was sparged with nitrogen for 30 min. and then Hoveyda-Grubbs catalyst (2nd generation) (25 mg, 0.040 mmol) was added and the reaction sealed and heated to 100° C. for 18 hours. The reaction was concentrated to give crude material. The crude material was purified by flash chromatography on the Biotage (10-40% EtOAc in hexanes) to give the product (177 mg, 0.315 mmol, 79% yield) as a white solid. $^1$H NMR (400 MHz, CHLOROFORM-d) δ ppm 0.95-1.01 (m, 3H) 1.02-1.05 (m, 3H) 1.05-1.10 (m, 9H) 1.82-1.92 (m, 1H) 2.26-2.44 (m, 2H) 3.03-3.07 (m, 3H) 3.14 (ddd, J=12.61, 8.09, 1.63 Hz, 1H) 3.45 (dd, J=10.04, 1.25 Hz, 1H) 3.68-3.74 (m, 1H) 3.76-3.81 (m, 3H) 4.01 (d, J=10.04 Hz, 1H) 4.39 (dd, J=10.79, 8.03 Hz, 1H) 4.52 (d, J=10.04 Hz, 1H) 4.85 (dd, J=10.79, 1.51 Hz, 1H) 5.33 (d, J=10.04 Hz, 1H) 6.16 (ddd, J=15.56, 10.79, 4.77 Hz, 1H) 6.29-6.39 (m, 1H) 7.29-7.36 (m, 3H) 7.37-7.45 (m, 2H) 7.47-7.53 (m, 2H) 7.54-7.60 (m, 1H). LCMS: r.t.=2.20 min., [M+H]$^+$=563 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 3:

A solution of the product from Step 2 (177 mg, 0.315 mmol) and 10% Pd/C (33 mg, 0.031 mmol) in EtOAc (10 mL) was stirred under an atmosphere of hydrogen for 16 hours. The reaction was filtered through a nylon frit and concentrated to give crude product (176 mg, 0.312 mmol, 99% yield) as a white solid. $^1$H NMR (400 MHz, CHLOROFORM-d) δ ppm 0.79 (s, 3H) 0.92-0.95 (m, 3H) 1.02-1.11 (m, 9H) 1.22 1.35 (m, 1H) 1.38-1.49 (m, 2H) 2.26-2.41 (m, 2H) 2.48-2.58 (m, 1H) 3.06 (s, 3H) 3.07-3.12 (m, 1H) 3.15 (d, J=10.79 Hz, 1H) 3.76-3.81 (m, 4H) 4.36 (d, J=10.54 Hz, 1H) 4.44 (d, J=10.04 Hz, 1H) 4.48 (dd, J=10.54, 8.03 Hz, 1H) 4.62-4.69 (m, 1H) 5.30 (d, J=9.79 Hz, 1H) 7.22 (d, J=2.01 Hz, 1H) 7.24 (d, J=2.51 Hz, 1H) 7.28-7.32 (m, 2H) 7.32-7.37 (m, 3H) 7.47 (d, J=8.28 Hz, 2H). LCMS: r.t.=2.13 min., [M+H]$^+$=565 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 4:

2.0 M lithium hydroxide (0.78 mL, 1.56 mmol) was added to a solution of the product from Step 3 (176 mg, 0.312 mmol) in THF (2.000 mL) and MeOH (2 mL) and stirred for 3 hours. The reaction was diluted with ether and 1.0 M HCl. The organic layer was dried, filtered and evaporated to give the crude product (160 mg, 0.291 mmol, 93% yield). LCMS: r.t.=1.92 min., [M+H]$^+$=551 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 5:

HATU (83 mg, 0.218 mmol) was added to a solution of (1S,2R)-2-amino-N-(cyclopropylsulfonyl)bi(cyclopropane)-2-carboxamide, HCl salt (49 mg, 0.174 mmol), the product from Step 4 (80 mg, 0.145 mmol) and Hunig's base (0.076 mL, 0.436 mmol) in dichloromethane (4 mL) and stirred at r.t. for 16 hours. The reaction was concentrated and purified by HPLC (Xbridge C18 10u (30×100 mm); flow=42 ml/min; solvent gradient=95:5 to 5:95 water/acetonitrile (with 10 mM ammonium acetate)). The product fractions were concentrated to give Compound 16 (35 mg, 0.044 mmol, 30% yield) as a white solid. $^1$H NMR (400 MHz, MeOD) δ ppm 0.33-0.44 (m, 2H) 0.54-0.72 (m, 2H) 0.86 (s, 3H) 0.88-0.95 (m, 1H) 1.04 (s, 3H) 1.10 (s, 9H) 1.12-1.23 (m, 4H) 1.24-1.39 (m, 4H) 1.41-1.54 (m, 2H) 1.85 (dd, J=8.03, 5.52 Hz, 1H) 2.30 (t, J=11.80 Hz, 1H) 2.35-2.46 (m, 1H) 2.47-2.59 (m, 1H) 3.01-3.10 (m, 2H) 3.13 (s, 3H) 3.24 (d, J=10.29 Hz, 1H) 3.89 (d, J=10.54 Hz, 1H) 4.25 (dd, J=10.79, 7.28 Hz, 1H) 4.37 (d, J=10.29 Hz, 1H) 4.53 (d, J=10.04 Hz, 1H) 4.80 (d, J=10.54 Hz, 1H) 6.90 (d, J=10.04 Hz, 1H) 7.20-7.31 (m, 2H) 7.31-7.38 (m, 2H) 7.41 (d, J=8.28 Hz, 2H) 7.60-7.68 (m, 2H). LCMS: r.t.=4.05 min., [M-OMe]$^+$=745 Phenomenex Luna C18, 50×2, 3u; Solvent A=10% acetonitrile 90% water—0.1% TFA, Solvent B=90% acetonitrile—10% water—0.1% TFA; gradient=0% to 100% solvent B over 4 min. and then hold for 1 min.; 0.8 ml/min; inj. vol.=3 ul; wavelength=220 nm.

Preparation of Compound 17

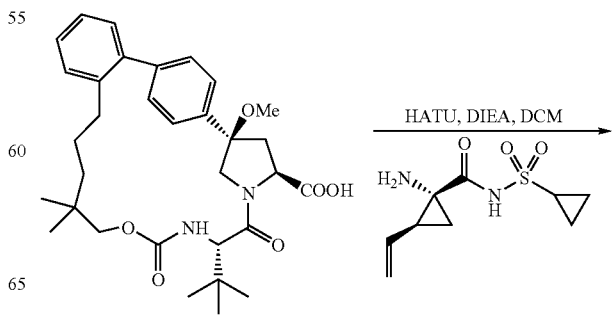

-continued

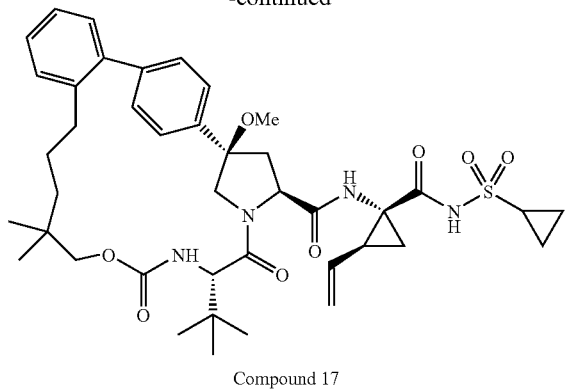

Compound 17

HATU (83 mg, 0.218 mmol) was added to a solution of (1R,2S)-1-amino-N-(cyclopropylsulfonyl)-2-vinylcyclopropanecarboxamide, TsOH salt (69.8 mg, 0.174 mmol), the product from step 4 of the preparation of compound 16 (80 mg, 0.145 mmol) and Hunig's base (0.076 mL, 0.436 mmol) in dichloromethane (4 mL) and stirred at r.t. for 16 hours. The reaction was concentrated and purified by HPLC (Xbridge C18 10u (30×100 mm); flow=42 ml/min; solvent gradient=95:5 to 5:95 water/acetonitrile (with 10 mM ammonium acetate)). The product fractions were concentrated to give Compound 17 (52 mg, 0.064 mmol, 44% yield) as a white solid. $^1$H NMR (400 MHz, MeOD) δ ppm 0.85 (s, 3H) 0.99-1.06 (m, 4H) 1.06-1.17 (m, 12H) 1.22-1.35 (m, 3H) 1.40-1.55 (m, 3H) 1.93 (dd, J=8.03, 5.27 Hz, 1H) 2.20-2.30 (m, 1H) 2.31-2.45 (m, 2H) 2.49-2.61 (m, 1H) 2.93-3.02 (m, 1H) 3.08-3.16 (m, 4H) 3.23 (d, J=10.29 Hz, 1H) 3.87-3.99 (m, 1H) 4.29 (dd, J=10.92, 7.40 Hz, 1H) 4.34 (d, J=10.54 Hz, 1H) 4.48-4.55 (m, 1H) 4.77 (d, J=10.54 Hz, 1H) 5.16 (dd, J=10.42, 1.63 Hz, 1H) 5.33 (dd, J=17.07, 1.25 Hz, 1H) 5.85 (ddd, J=17.13, 10.23, 9.03 Hz, 1H) 7.21-7.30 (m, 2H) 7.31-7.36 (m, 2H) 7.37-7.44 (m, 2H) 7.63 (d, J=8.28 Hz, 2H). LCMS: r.t.=4.23 min., [M-OMe]$^+$=731 Phenomenex Luna C18, 50×2, 3u; Solvent A=10% acetonitrile—90% water—0.1% TFA, Solvent B=90% acetonitrile—10% water—0.1% TFA; gradient=0% to 100% solvent B over 4 min. and then hold for 1 min.; 0.8 ml/min; inj. vol.=3 ul; wavelength=220 nm.

Preparation of Compound 18

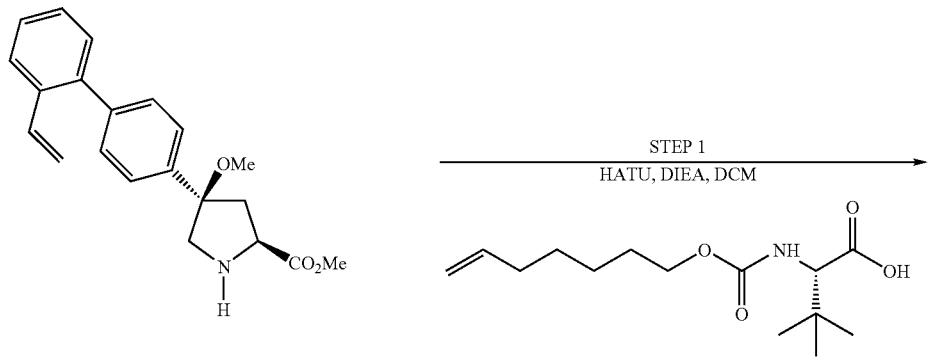

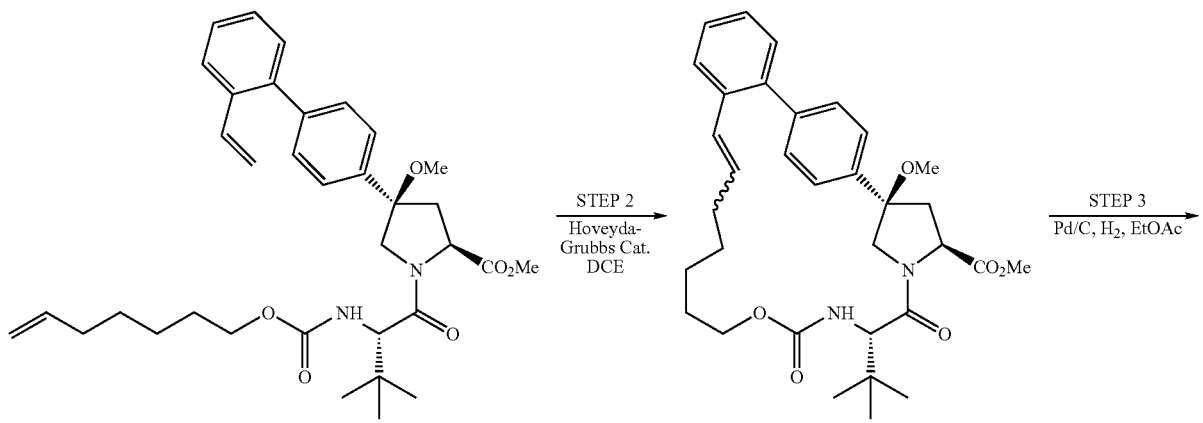

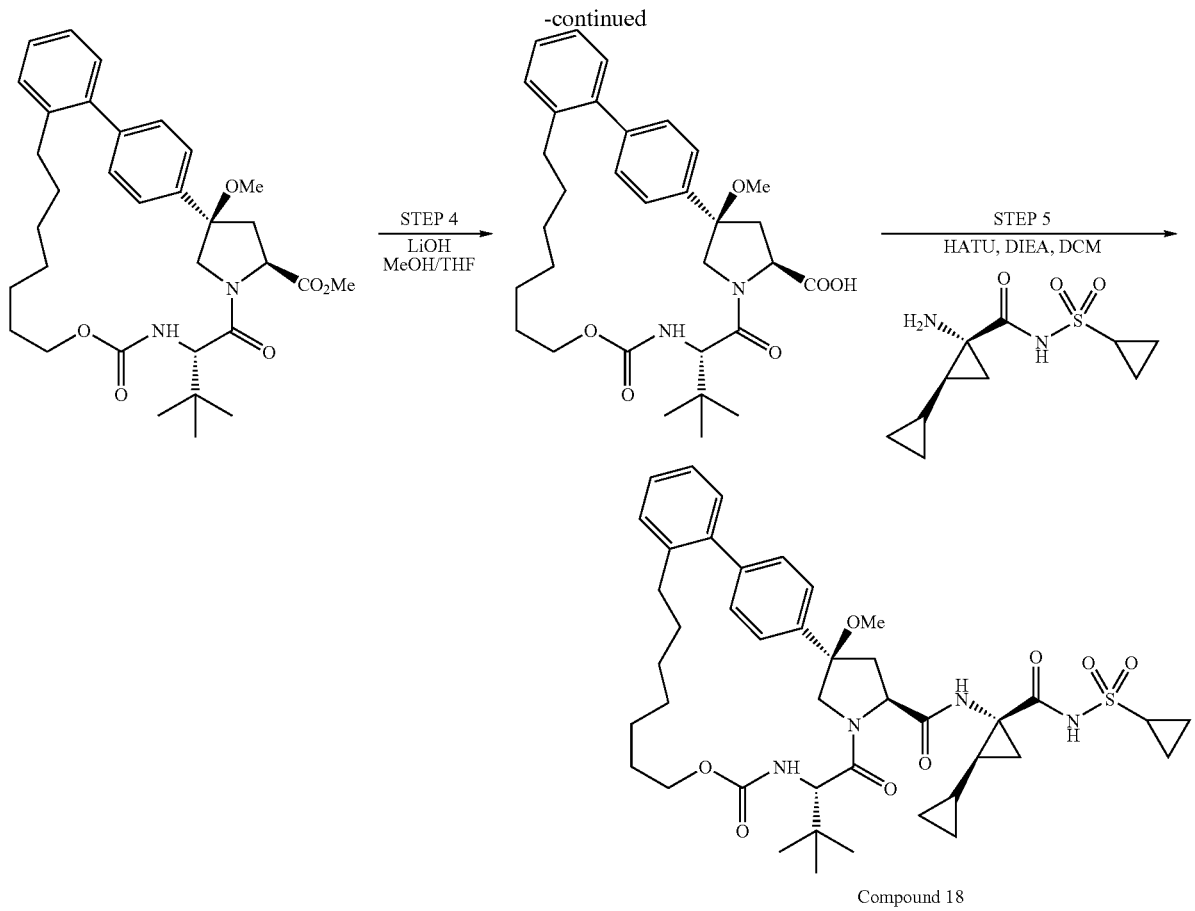

Compound 18

Step 1:

HATU (248 mg, 0.652 mmol) was added to a solution of (2S,4R)-methyl 4-methoxy-4-(2'-vinylbiphenyl-4-yl)pyrrolidine-2-carboxylate (200 mg, 0.593 mmol), (S)-2-((hept-6-enyloxy)carbonylamino)-3,3-dimethylbutanoic acid (201 mg, 0.741 mmol) and DIEA (0.311 mL, 1.778 mmol) in DCM (8 mL) and stirred at r.t. 60 hours. The reaction was evaporated and purified on the Biotage (10-40% EtOAc:Hex) to give (2S,4R)-methyl 1-((S)-2-((hept-6-enyloxy)carbonylamino)-3,3-dimethylbutanoyl)-4-methoxy-4-(2'-vinylbiphenyl-4-yl)pyrrolidine-2-carboxylate (260 mg, 0.440 mmol, 74% yield) as a white solid. $^1$H NMR (400 MHz, CHLOROFORM-d) δ ppm 0.96-1.00 (m, 1H) 1.06-1.10 (m, 1H) 1.11-1.19 (m, 7H) 1.30-1.47 (m, 4H) 1.55-1.64 (m, 2H) 1.99-2.10 (m, 2H) 2.49-2.55 (m, 1H) 2.89 (d, J=13.05 Hz, 1H) 2.93-3.04 (m, 3H) 3.73-3.80 (m, 3H) 3.92-4.10 (m, 3H) 4.11-4.20 (m, 1H) 4.31-4.41 (m, 1H) 4.87-5.05 (m, 3H) 5.23 (dd, J=10.92, 1.13 Hz, 1H) 5.38-5.42 (m, 1H) 5.68-5.75 (m, 1H) 5.75-5.86 (m, 1H) 6.62-6.76 (m, 1H) 7.28-7.43 (m, 7H) 7.63-7.69 (m, 1H). LCMS: r.t.=2.25 min., [M+H]$^+$=591 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 2:

A solution of (2S,4R)-methyl 1-((S)-2-((hept-6-enyloxy)carbonylamino)-3,3-dimethylbutanoyl)-4-methoxy-4-(2'-vinylbiphenyl-4-yl)pyrrolidine-2-carboxylate (260 mg, 0.440 mmol) in DCE (100 mL) was sparged with nitrogen for 30 min. and then Hoveyda-Grubbs catalyst (27 mg, 0.044 mmol) was added and the reaction sealed and heated to 100° C. for 18 hours. The reaction was concentrated to give crude material. The crude material was purified by flash chromatography on the Biotage (10-40% EtOAc in hexanes) to give the product (232 mg, 0.412 mmol, 94% yield) as a white solid. $^1$H NMR (400 MHz, CHLOROFORM-d) δ 1.08-1.15 (m, 9H) 1.32-1.41 (m, 2H) 1.42-1.59 (m, 3H) 1.69 (d, J=2.76 Hz, 1H) 2.06-2.19 (m, J=14.18, 9.60, 4.80, 4.80 Hz, 1H) 2.29-2.40 (m, 1H) 2.50 (t, J=11.42 Hz, 1H) 2.68 (dd, J=11.92, 7.40 Hz, 1H) 3.08 (s, 3H) 3.75 (s, 3H) 3.77-3.84 (m, 2H) 4.25 (dd, J=10.29, 7.53 Hz, 1H) 4.52 (d, J=10.29 Hz, 1H) 4.59 (td, J=10.54, 4.02 Hz, 1H) 4.83 (d, J=10.29 Hz, 1H) 5.35 (d, J=10.04 Hz, 1H) 5.98-6.12 (m, 1H) 6.39 (d, J=15.56 Hz, 1H) 7.28-7.33 (m, 3H) 7.40-7.46 (m, 2H) 7.46-7.52 (m, 2H) 7.56 (d, J=7.03 Hz, 1H). LCMS: r.t.=2.20 min., [M+H]$^+$=563 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 3:

A solution of the product from Step 2 (232 mg, 0.412 mmol) and 10% Pd/C (44 mg, 0.041 mmol) in EtOAc (10 mL) was stirred under an atmosphere of hydrogen for 16 hours. The reaction Was filtered through a nylon frit and concentrated to give product (207 mg, 0.367 mmol, 89% yield) as a white solid. LCMS: r.t.=2.18 min., [M+H]$^+$=565 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 4:

2.0 M lithium hydroxide (0.92 mL, 1.84 mmol) was added to a solution of the product from Step 3 (208 mg, 0.368 mmol) in THF (2 mL) and MeOH (2 mL) and stirred for 3 hours. The reaction was diluted with ether and 1.0 M HCl. The organic layer was dried, filtered and evaporated to give the product (200 mg, 0.363 mmol, 99% yield). LCMS: r.t.=2.01 min., [M+H]⁺=551 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Step 5:

HATU (104 mg, 0.272 mmol) was added to a solution of (1S,2R)-2-amino-N-(cyclopropylsulfonyl)bi(cyclopropane)-2-carboxamide, HCl salt (61 mg, 0.218 mmol), the product from Step 4 (100 mg, 0.182 mmol) and Hunig's base (0.095 mL, 0.545 mmol) in dichloromethane (4 mL) and stirred at r.t. for 64 hours. The reaction was concentrated and purified by HPLC (Xbridge C18 10u (30×100 mm); flow=42 ml/min; solvent gradient=95:5 to 5:95 water/acetonitrile (with 10 mM ammonium acetate)). The product fractions were concentrated to give Compound 18 (71 mg, 0.085 mmol, 46.8% yield) as a white solid. ¹H NMR (400 MHz, MeOD) δ ppm 0.32-0.43 (m, 2H) 0.53-0.68 (m, 2H) 0.85-0.95 (m, 1H) 1.10-1.24 (m, 13H) 1.24-1.41 (m, 8H) 1.49-1.72 (m, 4H) 1.80 (dd, J=8.03, 5.27 Hz, 1H) 2.49-2.68 (m, 4H) 3.01-3.09 (m, 1H) 3.13 (s, 3H) 3.72-3.84 (m, 1H) 4.04 (d, J=10.54 Hz, 1H) 4.17 (t, J=8.16 Hz, 1H) 4.47-4.59 (m, 2H) 4.66 (d, J=10.54 Hz, 1H) 7.21-7.31 (m, 2H) 7.35 (d, J=3.76 Hz, 2H) 7.40-7.46 (m, 2H) 7.64 (d, J=7.78 Hz, 2H). LCMS: r.t.=2.13 min., [M-OMe]⁺=745 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Preparation of Compound 19

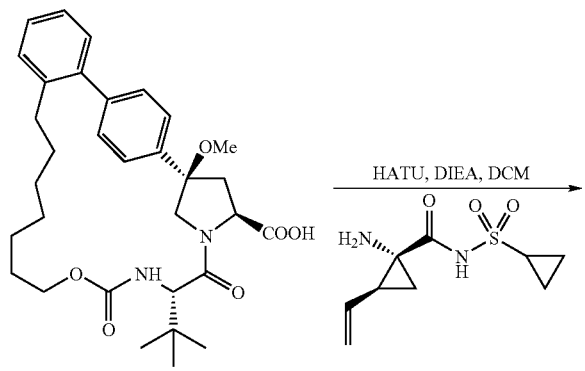

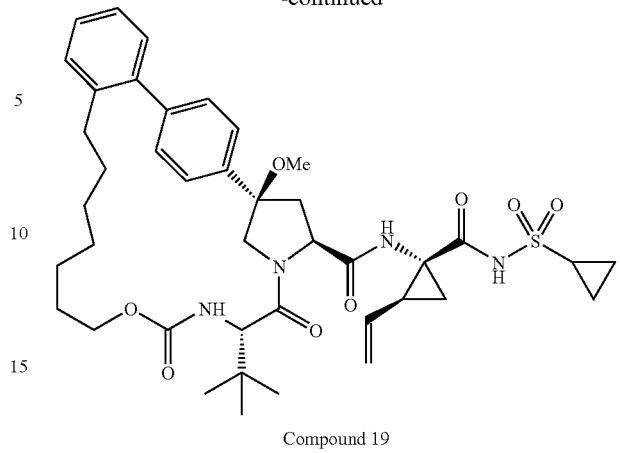

Compound 19

HATU (104 mg, 0.272 mmol) was added to a solution of (1R,2S)-1-amino-N-(cyclopropylsulfonyl)-2-vinylcyclopropanecarboxamide, TsOH salt (87 mg, 0.218 mmol), the product from Step 4 of the preparation of compound 18 (100 mg, 0.182 mmol) and Hunig's base (0.095 mL, 0.545 mmol) in dichloromethane (4 mL) and stirred at r.t. for 16 hours. The reaction was concentrated and purified by HPLC (Xbridge C18 10u (30×100 mm); flow=42 ml/min; solvent gradient=95:5 to 5:95 water/acetonitrile (with 10 mM ammonium acetate)). The product fractions were concentrated to give Compound 19 (67 mg, 0.083 mmol, 46% yield) as a white solid. ¹H NMR (400 MHz, MeOD) δ ppm 1.06-1.15 (m, 2H) 1.18 (s, 9H) 1.29 (br. s., 4H) 1.30 (d, J=4.52 Hz, 4H) 1.45-1.70 (m, 5H) 1.86-1.98 (m, 1H) 2.18-2.29 (m, 1H) 2.49-2.72 (m, 4H) 2.94-3.06 (m, 1H) 3.14 (s, 3H) 3.71-3.85 (m, 1H) 4.06 (d, J=10.54 Hz, 1H) 4.21 (t, J=8.03 Hz, 1H) 4.47-4.59 (m, 2H) 4.64 (d, J=10.54 Hz, 1H) 5.13-5.22 (m, 1H) 5.27-5.40 (m, 1H) 5.82 (ddd, J=17.19, 10.29, 8.91 Hz, 1H) 7.21-7.32 (m, 2H) 7.35 (d, J=3.51 Hz, 2H) 7.43 (d, J=8.28 Hz, 2H) 7.65 (d, J=8.03 Hz, 2H). LCMS: r.t.=2.08 min., [M-OMe]⁺=731 Phenomenex Luna S10 (3×50 mm); Solvent A=95% water—5% methanol—10 mM ammonium acetate, Solvent B=5% water—95% methanol—10 mM ammonium acetate; gradient=0% to 100% solvent B over 2 min. and then hold for 1 min.; 4 ml/min; inj. vol.=10 ul; wavelength=220 nm.

Preparation of Intermediate 12:

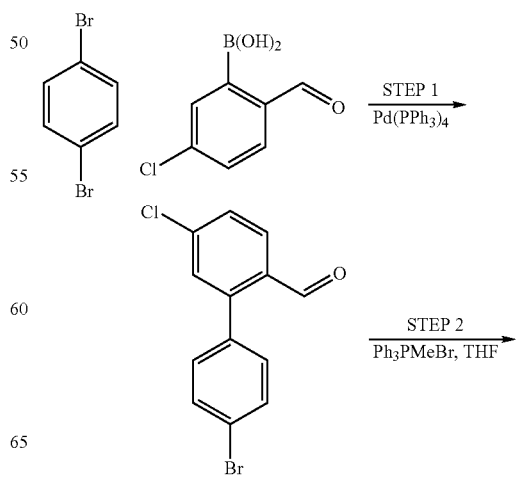

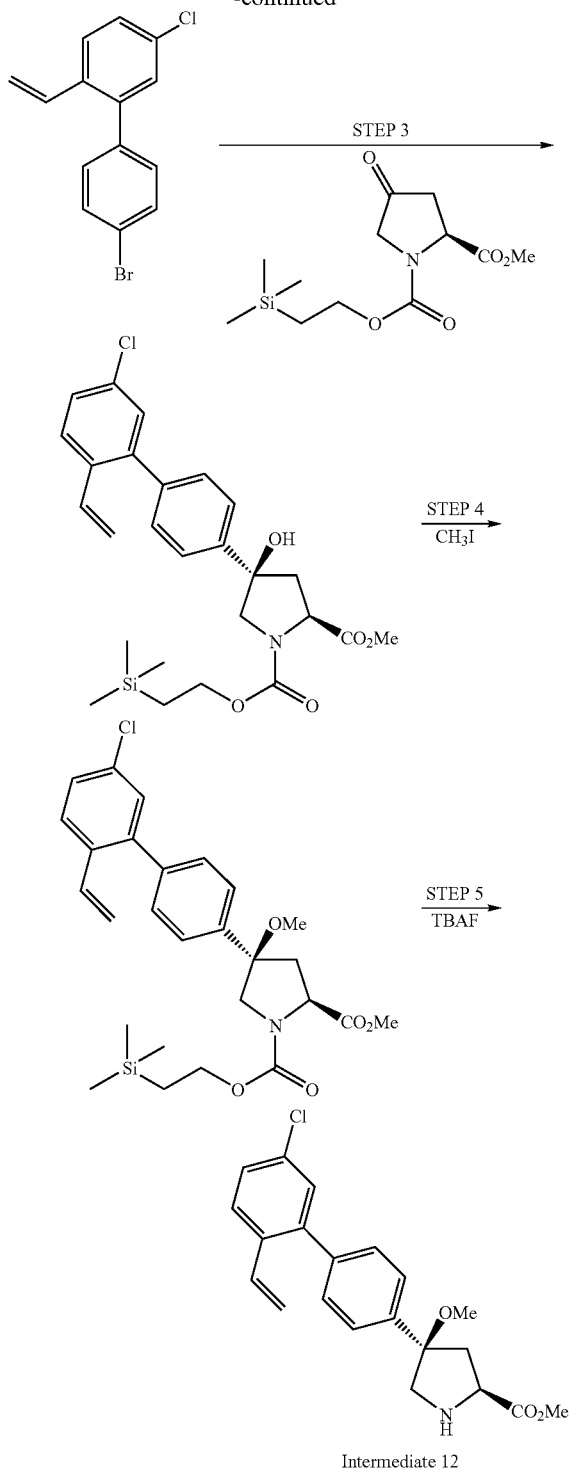

Intermediate 12

Step 1:

A solution of 1,4-dibromobenzene (8.3 g, 35.3 mmol), potassium carbonate (11.3 g, 81 mmol) and 5-chloro-2-formylphenylboronic acid (5 g, 27.1 mmol) in DME (150 mL) and water (30 mL) (in a pressure vessel) was sparged with nitrogen for 15 min. Pd(PPh$_3$)$_4$ (0.94 g, 0.814 mmol) was added and the reaction heated to 80° C. overnight. The reaction was cooled to r.t. and evaporated on the rotovap. The residue was diluted in EtOAc and washed with water then brine, dried over MgSO$_4$, filtered and evaporated to give the crude material. The crude material was purified by flash chromatography on the Biotage (0-15% EtOAc:Hex) to give 4'-bromo-5-chlorobiphenyl-2-carbaldehyde (4.17 g, 14.11 mmol, 52% yield) as a white solid. $^1$H NMR (400 MHz, CHLOROFORM-d) δ ppm 7.18-7.28 (m, 2H) 7.42 (d, J=2.01 Hz, 1H) 7.50 (ddd, J=8.41, 2.01, 0.88 Hz, 1H) 7.59-7.69 (m, 2H) 7.98 (d, J=8.53 Hz, 1H) 9.92 (s, 1H).

Step 2:

BuLi (2.5M in hexanes, 11.3 mL, 28.2 mmol) was added to a solution of methyltriphenylphosphonium bromide (10.1 g, 28.2 mmol) in THF (65 mL). The mixture was stirred at 0° C. for 1 hr. A solution of 4'-bromo-5-chlorobiphenyl-2-carbaldehyde (4.2 g, 14.11 mmol) in THF (65 mL) was added dropwise at 0° C. The mixture was stirred overnight from 0° C. to r.t. The reaction was filtered and evaporated. The residue was diluted with diethyl ether and washed with water and brine. The ether layer was collected, dried (MgSO$_4$), filtered and evaporated to give the crude material. The crude material was purified on the Biotage (5-15% EtOAc:Hex) to give 4'-bromo-5-chloro-2-vinylbiphenyl (3.43 g, 11.68 mmol, 83% yield) as a clear oil.

$^1$H NMR (500 MHz, CHLOROFORM-d) δ ppm 5.22 (d, J=10.99 Hz, 1H) 5.67 (dd, J=17.40, 1.22 Hz, 1H) 6.57 (dd, J=17.40, 10.99 Hz, 1H) 7.16-7.21 (m, 2H) 7.24 (d, J=2.14 Hz, 1H) 7.31 (dd, J=8.39, 2.29 Hz, 1H) 7.50-7.58 (m, 3H).

Step 3:

Magnesium (0.298 g, 12.27 mmol) was stirred in a round bottom flask under nitrogen for 15 min. to cause scratching of the surface of the magnesium turnings. 10 mL of THF was added to the magnesium turnings and stirred for an additional 30 min. 4'-bromo-5-chloro-2-vinylbiphenyl (3.43 g, 11.68 mmol) in THF (60 mL), was added in dropwise at reflux with vigorous stirring. The Grignard solution was added to a solution of (S)-2-methyl 1-(2-(trimethylsilyl)ethyl) 4-oxopyrrolidine-1,2-dicarboxylate (3.35 g, 11.67 mmol) in DCM (60 mL) at r.t. and stirred for 1 hr and then quenched with saturated NH$_4$Cl solution. The aqueous layer was extracted with DCM and the combined organics were dried, filtered and evaporated to give crude material. The crude material was purified by flash chromatography on the Biotage (10-40% EtOAc:Hex) to give (2S,4R)-2-methyl 1-(2-(trimethylsilyl)ethyl) 4-(5'-chloro-2'-vinylbiphenyl-4-yl)-4-hydroxypyrrolidine-1,2-dicarboxylate (800 mg, 1.593 mmol, 14% yield) as a yellow oil. $^1$H NMR (500 MHz, CHLOROFORM-d) δ ppm 0.04 (s, 9H) 1.03 (dd, j=9.46, 7.63 Hz, 2H) 2.30-2.48 (m, 1H) 2.63-2.79 (m, 1H) 3.77-3.80 (m, 1H) 3.82-3.86 (m, 3H) 3.95-4.05 (m, 1H) 4.16-4.26 (m, 2H) 4.51-4.67 (m, 1H) 5.20 (d, J=11.90 Hz, 1H) 5.67 (d, J=17.40 Hz, 1H) 6.61 (dd, J=17.40, 10.99 Hz, 1H) 7.26-7.35 (m, 4H) 7.49-7.58 (m, 3H).

Step 4:

NaH (60% in oil) (106 mg, 2.65 mmol) was added to a solution of (2S,4R)-2-methyl 1-(2-(trimethylsilyl)ethyl) 4-(5'-chloro-2'-vinylbiphenyl-4-yl)-4-hydroxypyrrolidine-1,2-dicarboxylate (740 mg, 1.474 mmol) and methyl iodide (0.166 mL, 2.65 mmol) at 0° C. in DMF and stirred at this temperature and allowed to warm up to r.t. overnight. The reaction was then quenched with saturated NH$_4$Cl solution and ether. The ether layer was washed with brine, dried, filtered and evaporated to give crude material. The crude material was purified by flash chromatography on the Biotage (5-40% EtOAc in hexanes) to give semi purified product (2S,4R)-2-methyl 1-(2-(trimethylsilyl)ethyl) 4-(5'-chloro-2'-vinylbiphenyl-4-yl)-4-methoxypyrrolidine-1,2-dicarboxylate (333 mg, 0.645 mmol, 44% yield) as a clear oil. $^1$H NMR (500 MHz, CHLOROFORM-d) δ ppm 0.04 (s, 9H) 1.01-1.06 (m, 2H) 2.52 (dd, J=13.12, 8.85 Hz, 1H) 2.78-2.87 (m, 1H)

2.97 (d, J=5.19 Hz, 3H) 3.65 (s, 1H) 3.67-3.75 (m, 3H) 3.77 (d, J=8.85 Hz, 3H) 3.96-4.08 (m, 1H) 5.21 (d, J=10.99 Hz, 1H) 5.68 (d, J=17.40 Hz, 1H) 6.59 (ddd, J=17.47, 11.06, 2.29 Hz, 1H) 7.26 (d, J=2.14 Hz, 1H) 7.29-7.35 (m, 3H) 7.35-7.40 (m, 2H) 7.56 (d, J=8.24 Hz, 1H).

Step 5:

TBAF (2.58 mL, 2.58 mmol) was added to a solution of (2S,4R)-2-methyl 1-(2-(trimethylsilyl)ethyl) 4-(5'-chloro-2'-vinylbiphenyl-4-yl)-4-methoxypyrrolidine-1,2-dicarboxylate (333 mg, 0.645 mmol) in THF (6 mL) and stirred at r.t. for 2 hours. The reaction was diluted with water and extracted with EtOAc. The organic layer was washed with brine, dried over MgSO₄, filtered and evaporated on rotovap to give (2S, 4R)-methyl 4-(5'-chloro-2'-vinylbiphenyl-4-yl)-4-methoxypyrrolidine-2-carboxylate (Intermediate 12, 215 mg, 0.578 mmol, 90% yield) as a yellow oil. LCMS: rt=1.49 min. [M-MeOH]⁺=340; Phenomenex-Luna C-18 (5μ) (3.0×50 mm); Solvent A=10% acetonitrile—90% water—0.1% TFA, Solvent B=90% acetonitrile 10% water—0.1% TFA; gradient 0% to 100% solvent B over 2 min. and then hold for 1 min.; 4 mL/min; inj. vol.=5 uL; wavelength=220.

Preparation of Compound 20:

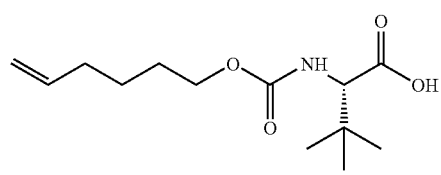

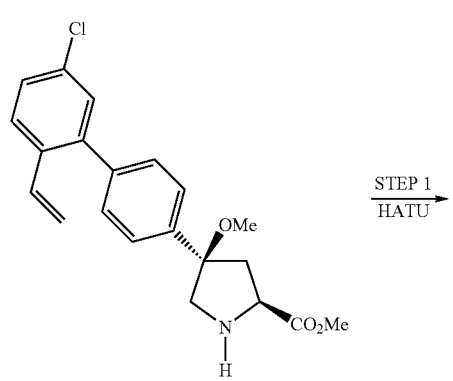

STEP 1
HATU →

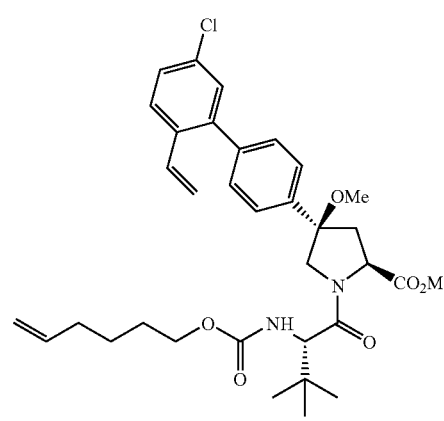

STEP 2
Hoveyda-Grubbs
2nd Generation →

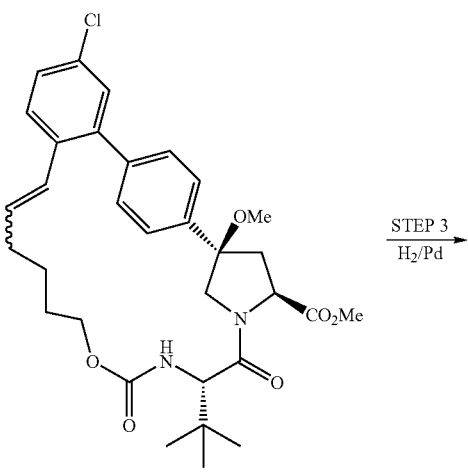

STEP 3
H₂/Pd →

-continued

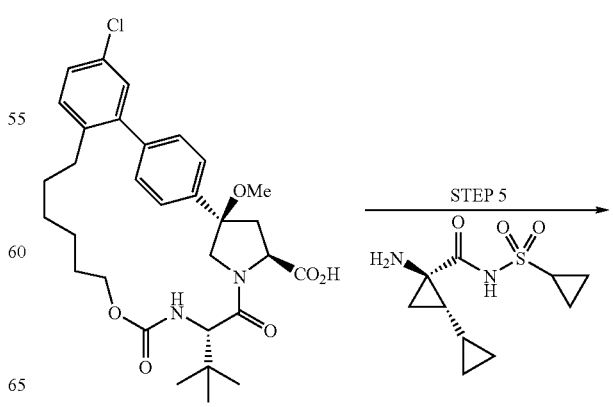

STEP 4
LiOH →

STEP 5 →

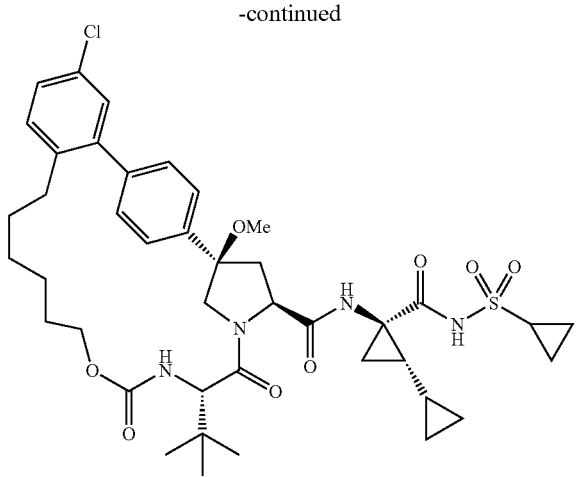

Compound 20

Step 1:

(S)-2-((hex-5-enyloxy)carbonylamino)-3,3-dimethylbutanoic acid (186 mg, 0.723 mmol), DIEA (0.303 mL, 1.735 mmol) and HATU (242 mg, 0.636 mmol) were added to a solution of (2S,4R)-methyl 4-(5'-chloro-2'-vinylbiphenyl-4-yl)-4-methoxypyrrolidine-2-carboxylate (215 mg, 0.578 mmol) in DCM (7 mL). The reaction was stirred at r.t. overnight. The reaction was evaporated and purified on the Biotage (10-50% EtOAc:Hex) to give (2S,4R)-methyl 4-(5'-chloro-2'-vinylbiphenyl-4-yl)-1-((S)-2-((hex-5-enyloxy)carbonylamino)-3,3-dimethylbutanoyl)-4-methoxypyrrolidine-2-carboxylate (13 mg, 0.201 mmol, 35% yield) as a colorless oil. LCMS: rt=2.58 min. [M+H]$^+$=612; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 2:

(2S,4R)-methyl 4-(5'-chloro-2'-vinylbiphenyl-4-yl)-1-((S)-2-((hex-5-enyloxy)carbonylamino)-3,3-dimethylbutanoyl)-4-methoxypyrrolidine-2-carboxylate (123 mg, 0.201 mmol) was dissolved in DCE (25 mL) and sparged with nitrogen for 15 min. Hoveyda-Grubbs catalyst (13 mg, 0.020 mmol) was added and heated in an oil bath at 80° C. for 2 hours. The reaction was evaporated and the crude product was purified by flash chromatography on the Biotage (10-50% EtOAc/Hex) to give the product (95 mg, 0.163 mmol, 81% yield) as a white foam. LCMS: rt=2.44 min. [M+H]$^+$=584 and [M-MeOH]$^+$=551; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 3:

The product from Step 2 (95 mg, 0.163 mmol) was dissolved in ethyl acetate (3 mL) and treated with 10% palladium on carbon (17 mg, 0.016 mmol) and stirred under a balloon of hydrogen overnight. The reaction was filtered through a Millipore millex-HV 0.45 um frit and evaporated to give the product (90 mg, 0.154 mmol, 94% yield). LCMS: rt=2.40 min. [M+H]$^+$=586 and [M-OMe]+=553; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 4:

2M Lithium hydroxide (0.23 mL, 0.46 mmol) was added to a solution of product from Step 3 (90 mg, 0.154 mmol) in THF (1 mL) and methanol (1 mL) and stirred at r.t. for 18 hrs. The reaction was then diluted with 5 mL of 1M HCl and extracted with EtOAc. The organic layer was washed with water then brine, dried over MgSO$_4$, filtered and then evaporated to give the product (74 mg, 0.130 mmol, 84% yield) as a white solid. LCMS: rt=2.19 min. [M+H]$^+$=572; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 5:

DIEA (0.068 mL, 0.389 mmol), HATU (54 mg, 0.143 mmol), and (1S,2R)-2-amino-N-(cyclopropylsulfonyl)bi(cyclopropane)-2-carboxamide, HCl salt (44 mg, 0.155 mmol) were added to a solution of the product from Step 4 (74 mg, 0.130 mmol) in DCM (2 mL). The reaction was stirred at r.t. overnight. The reaction was evaporated and purified by prep HPLC to give Compound 20 (52 mg, 0.065 mmol, 50% yield) as an off white solid. $^1$H NMR (500 MHz, CHLOROFORM-d) δ ppm 0.24-0.34 (m, 1H) 0.40 (br. s., 1H) 0.56 (t, J=6.41 Hz, 2H) 0.92 (d, J=12.51 Hz, 2H) 1.01 (s, 9H) 1.05-1.16 (m, 4H) 1.16-1.21 (m, 1H) 1.30-1.40 (m, 2H) 1.39-1.49 (m, 1H) 1.73-1.81 (m, 1H) 2.47 (br. s., 1H) 2.52-2.64 (m, 2H) 2.64-2.78 (m, 1H) 2.90-3.01 (m, 1H) 3.03 (s, 3H) 3.10-3.21 (m, 1H) 3.60 (d, J=10.38 Hz, 1H) 3.72-3.83 (m, 1H) 3.92 (d, J=10.38 Hz, 1H) 3.98-4.08 (m, 1H) 4.13 (d, J=10.07 Hz, 1H) 4.37 (d, J=9.77 Hz, 1H) 4.44 (t, J=7.32 Hz, 1H) 4.47-4.56 (m, 1H) 4.86 (d, J=8.85 Hz, 1H) 5.45 (br. s., 1H) 5.76 (br. s., 1H) 7.10-7.21 (m, 2H) 7.24 (s, 1H) 7.28-7.33 (m, 1H) 7.37 (d, J=7.63 Hz, 1H) 7.41 (d, J=5.19 Hz, 2H) 9.95 (br. s., 1H). LCMS: rt=2.44 min. [M-OMe]$^+$=765; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Preparation of Intermediate 13:

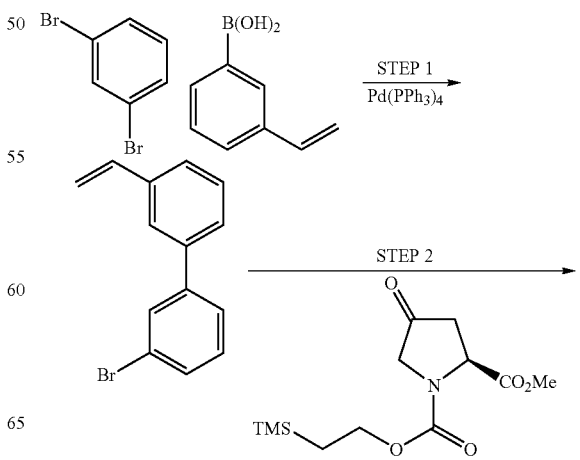

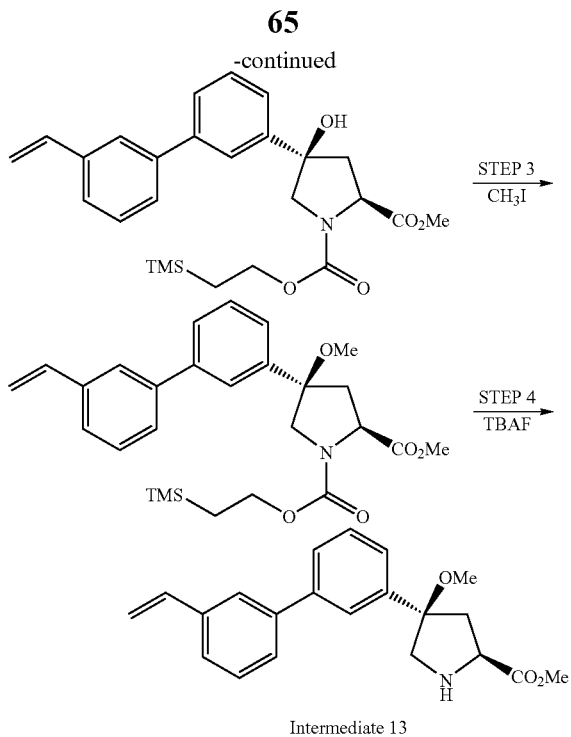

Intermediate 13

Step 1:

A solution of 1,3-dibromobenzene (5.3 mL, 43.9 mmol), potassium carbonate (14.0 g, 101 mmol) and 3-vinylphenylboronic acid (5 g, 33.8 mmol) in DME (100 mL) and water (20 mL) (in a pressure vessel) was sparged with nitrogen for 15 min. Pd(PPh$_3$)$_3$ (1.17 g, 1.014 mmol) was added and then the reaction was heated to 80° C. overnight. The reaction was cooled to r.t. and evaporated on the rotovap. The residue was diluted in EtOAc and washed with water then brine, dried over MgSO$_4$, filtered and evaporated to give the crude material. The crude material was purified by flash chromatography on the Biotage (0-5% EtOAc:Hex) to give 3-bromo-3'-vinylbiphenyl (5.21 g, 20.10 mmol, 60% yield) as a clear liquid. $^1$H NMR (400 MHz, CHLOROFORM-d) δ ppm 5.33 (d, J=10.79 Hz, 1H) 5.84 (dd, J=17.57, 0.75 Hz, 1H) 6.80 (dd, J=17.57, 10.79 Hz, 1H) 7.32 (t, J=7.78 Hz, 1H) 7.38-7.48 (m, 3H) 7.51 (dddd, J=13.24, 7.84, 1.76, 1.00 Hz, 2H) 7.56-7.61 (m, 1H) 7.76 (t, J=1.88 Hz, 1H).

Step 2:

Magnesium (0.513 g, 21.11 mmol) was stirred in a round bottom flask under nitrogen for 30 min. to cause scratching of the surface of the magnesium turnings. 10 mL of THF was added to the magnesium turnings and stirred for an additional 30 min. 3-bromo-3'-vinylbiphenyl (5.21 g, 20.10 mmol) in THF (100 mL), was added in dropwise at reflux with vigorous stirring. The Grignard solution was added to a solution of (S)-2-methyl 1-(2-(trimethylsilyl)ethyl) 4-oxopyrrolidine-1,2-dicarboxylate (5.78 g, 20.11 mmol) in DCM (110 mL) at 0° C. and stirred for 1 hr and then quenched with saturated NH$_4$Cl solution. The aqueous layer was extracted with DCM and the combined organics were dried, filtered and evaporated to give crude material. The crude material was purified by flash chromatography on the Biotage (5-40% EtOAc:Hex) to give (2S,4R)-2-methyl 1-(2-(trimethylsilyl)ethyl) 4-hydroxy-4-(3'-vinylbiphenyl-3-yl)pyrrolidine-1,2-dicarboxylate (2.9 g, 6.20 mmol, 31% yield) as a yellow foam. $^1$H NMR (500 MHz, CHLOROFORM-d) δ 0.05 (d, J=2.44 Hz, 9H) 0.99 (dd, J=9.77, 7.32 Hz, 1H) 1.04 (dd, J=9.61, 7.17 Hz, 1H) 1.27 (t, J=7.17 Hz, 1H) 2.38-2.53 (m, 1H) 2.66-2.82 (m, 1H) 3.67-3.83 (m, 1H) 3.82-3.89 (m, 3H) 3.96-4.09 (m, 1H) 4.17-4.32 (m, 2H) 4.52-4.69 (m, 1H) 5.32 (d, J=10.99 Hz, 1H) 5.83 (d, J=17.40 Hz, 1H) 6.80 (dd, J=17.55, 10.83 Hz, 1H) 7.39-7.46 (m, 2H) 7.46-7.52 (m, 3H) 7.55 (ddd, J=4.58, 2.14, 1.83 Hz, 1H) 7.61 (br. s., 1H) 7.73 (s, 1H). LCMS: rt=2.32 min. [M+H]$^+$=468; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 3:

NaH (60% in oil) (0.446 g, 11.16 mmol) was added to a solution of (2S,4R)-2-methyl 1-(2-(trimethylsilyl)ethyl) 4-hydroxy-4-(3'-vinylbiphenyl-3-yl)pyrrolidine-1,2-dicarboxylate (2.9 g, 6.20 mmol) and methyl iodide (0.698 mL, 11.16 mmol) at 0° C. in DMF and stirred at this temperature for 3 hrs. The reaction was then quenched with saturated NH$_4$Cl solution and ether. The ether layer was washed with brine, dried, filtered and evaporated to give crude material. The crude material was purified by flash chromatography on the Biotage (5-45% EtOAc in hexanes) to give (2S,4R)-2-methyl 1-(2-(trimethylsilyl)ethyl) 4-methoxy-4-(3'-vinylbiphenyl-3-yl)pyrrolidine-1,2-dicarboxylate (2.3 g, 4.78 mmol, 77% yield) as a clear oil. $^1$H NMR (400 MHz, CHLOROFORM-d) δ ppm −0.04-0.11 (m, 9H) 0.89-1.12 (m, 2H) 2.56 (dd, J=13.18, 8.91 Hz, 1H) 2.86 (t, J=12.67 Hz, 1H) 2.99 (d, J=3.01 Hz, 3H) 3.66-3.92 (m, 1H) 3.79 (d, J=7.03 Hz, 3H) 3.99-4.12 (m, 1H) 4.18-4.29 (m, 2H) 4.44-4.70 (m, 1H) 5.33 (d, J=10.79 Hz, 1H) 5.84 (d, J=16.82 Hz, 1H) 6.80 (dd, J=17.57, 11.04 Hz, 1H) 7.34 (d, J=7.53 Hz, 1H) 7.39-7.52 (m, 4H) 7.53-7.59 (m, 3H). LCMS: rt=2.49 min. [M+H]$^+$=482; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 4:

TBAF (1.0M in THF, 19 mL, 19 mmol) was added to a solution of (2S,4R)-2-methyl 1-(2-(trimethylsilyl)ethyl) 4-methoxy-4-(3'-vinylbiphenyl-3-yl)pyrrolidine-1,2-dicarboxylate (2.3 g, 4.78 mmol) in THF (30 mL) and stirred at r.t. overnight. The reaction was diluted with EtOAc and washed with water and then brine. The organic layer was collected, dried over MgSO$_4$, filtered and evaporated to give (2S,4R)-methyl 4-methoxy-4-(3'-vinylbiphenyl-3-yl)pyrrolidine-2-carboxylate (1.75 g, 5.19 mmol, 100% yield) as a yellow oil. LCMS: rt=1.42 min. [M-OMe]$^+$=306; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Preparation of Compound 21:

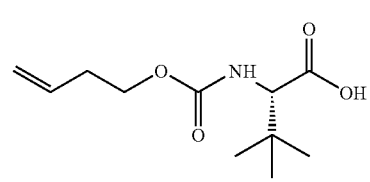

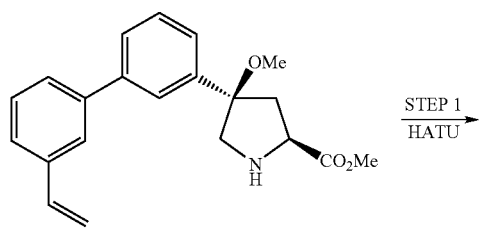

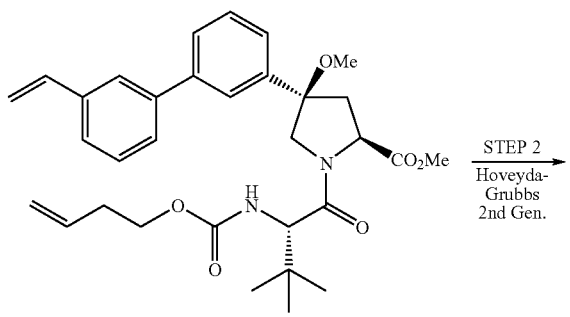

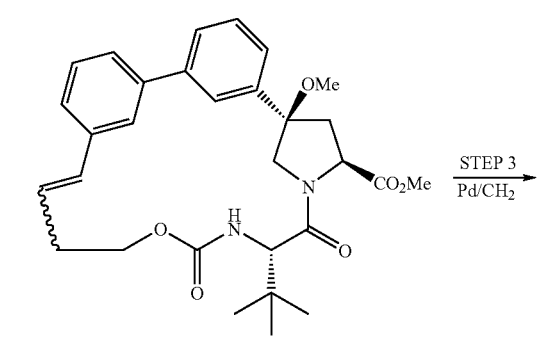

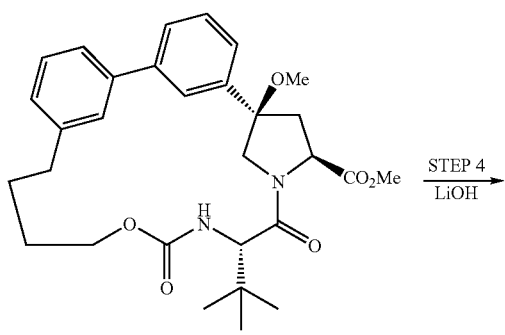

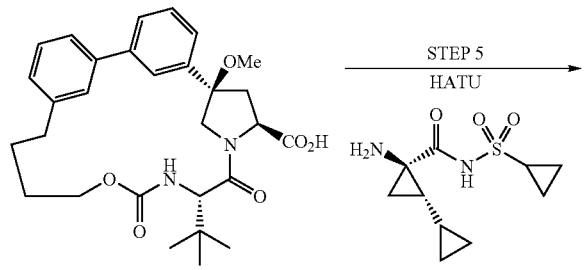

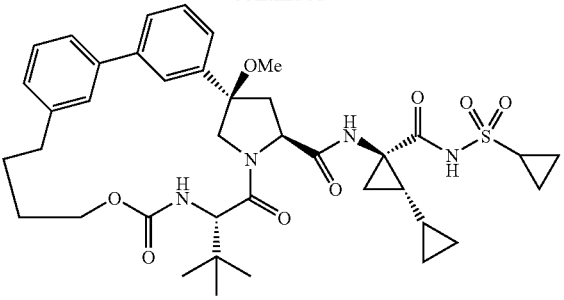

Compound 21

Step 1:

(S)-2-((but-3-enyloxy)carbonylamino)-3,3-dimethylbutanoic acid (255 mg, 1.111 mmol), DIEA (0.40 mL, 2.223 mmol) and HATU (310 mg, 0.815 mmol) were added to a solution of (2S,4R)-methyl 4-methoxy-4-(3'-vinylbiphenyl-3-yl)pyrrolidine-2-carboxylate (250 mg 0.741 mmol) in DCM (3 mL). The reaction was stirred at r.t. for 2 hrs. The reaction was evaporated and purified by flash chromatography on the Biotage (10-40% EtOAc:Hex) to give (2S,4R)-methyl 1-((S)-2-((but-3-enyloxy)carbonylamino)-3,3-dimethylbutanoyl)-4-methoxy-4-(3'-vinylbiphenyl-3-yl) pyrrolidine-2-carboxylate (277 mg, 0.505 mmol, 68% yield) as a white foam. LCMS: rt=2.31 min. [M+H]$^+$=549; Phenomenex-Luna C-18 (5μ) (3.0×50 mm); Solvent A=10% acetonitrile—90% water—0.1% TFA, Solvent 13=90% acetonitrile—10% water—0.1% TFA; gradient 0% to 100% solvent B over 2 min. and then hold for 1 min.; 4 mL/min, inj. vol.=5 uL; wavelength=220.

Step 2:

(2S,4R)-methyl 1-((S)-2-((but-3-enyloxy)carbonylamino)-3,3-dimethylbutanoyl)-4-methoxy-4-(3'-vinylbiphenyl-3-yl)pyrrolidine-2-carboxylate (277 mg, 0.505 mmol) was dissolved in DCE (75 mL) and sparged with nitrogen for 15 min. Hoveyda-Grubbs catalyst $2^{nd}$ generation (32 mg, 0.050 mmol) was added and heated in an oil bath at 80° C. for 2 hrs. The reaction was cooled, evaporated and purified on the Biotage (5-50% EtOAc/Hex) to give the final product (140 mg, 0.269 mmol, 53% yield) as a white foam. LCMS: rt=2.17 min. [M+H]$^+$=521; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 3:

Product from Step 2 (140 mg, 0.269 mmol) in ethyl acetate (3 mL) was treated with 10% palladium on carbon (29 mg, 0.027 mmol) and stirred under a balloon of hydrogen overnight. The reaction was filtered through a Millipore millex-HV 0.45 um frit and evaporated to give the product (139 mg, 0.266 mmol, 99% yield). LCMS: rt=2.22 min. [M+H]$^+$=523; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol. 5 uL; wavelength=220.

Step 4:

2M Lithium hydroxide (0.40 mL, 0.80 mmol) was added to a solution of product from Step 3 (139 mg, 0.266 mmol) in THF (1.5 mL) and methanol (1.5 mL) and stirred at r.t. for 18 hrs. The reaction was then diluted with 5 mL of 1M HCl and extracted with EtOAc. The organic layer was washed with water then brine, dried over MgSO₄, filtered and then evaporated to give the product (130 mg, 0.256 mmol, 96% yield) as a white solid. LCMS: rt=1.98 min. [M+H]⁺=509; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 5:

DIEA (0.134 mL, 0.767 mmol), HATU (107 mg, 0.281 mmol), and (1S,2R)-2-amino-N-(cyclopropylsulfonyl)bi(cyclopropane)-2-carboxamide, HCl salt (86 mg, 0.307 mmol) were added to a solution of product from Step 4 (130 mg, 0.256 mmol) in DCM (2.5 mL). The reaction was stirred at r.t. for 2 hours. The reaction was evaporated and purified by prep HPLC to give Compound 21 (63 mg, 0.084 mmol, 33% yield) as an off white solid. ¹H NMR (500 MHz, CHLOROFORM-d) δ ppm 0.13-0.26 (m, 2H) 0.43-0.57 (m, 2H) 0.79-0.89 (m, 2H) 0.94-1.01 (m, 2H) 1.04 (s, 9H) 1.20 (dd, J=9.77, 5.49 Hz, 1H) 1.23-1.28 (m, 1H) 1.29-1.37 (m, 1H) 1.53-1.73 (m, 2H) 1.73-1.84 (m, 2H) 2.30 (dd, J=12.36, 6.87 Hz, 1H) 2.51-2.69 (m, 2H) 2.71-2.81 (m, 1H) 2.82-2.95 (m, 1H) 3.16 (s, 3H) 3.78 (td, J=7.40, 3.81 Hz, 1H) 3.97 (dd, J=9.31, 6.87 Hz, 1H) 4.02 (d, J=10.38 Hz, 1H) 4.50 (d, J=9.77 Hz, 1H) 4.62-4.71 (m, 1H) 4.73 (d, J=10.38 Hz, 1H) 5.75 (d, J=9.77 Hz, 1H) 6.52 (s, 1H) 7.15 (d, J=7.02 Hz, 1H) 7.29-7.42 (m, 4H) 7.43-7.58 (m, 3H). LCMS: rt=2.23 min. [M+H]⁺=735; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Preparation of Intermediate 14:

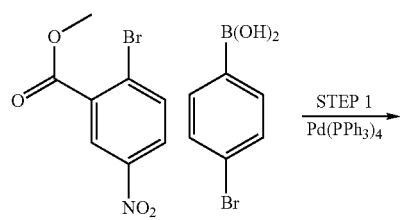

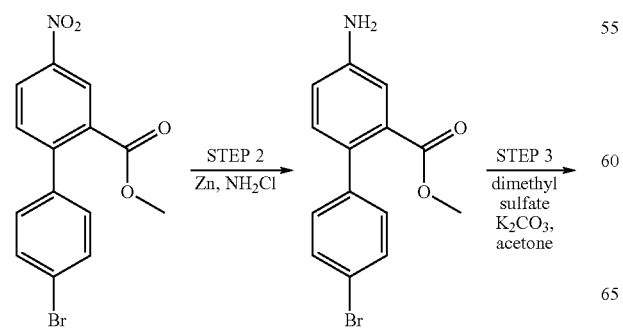

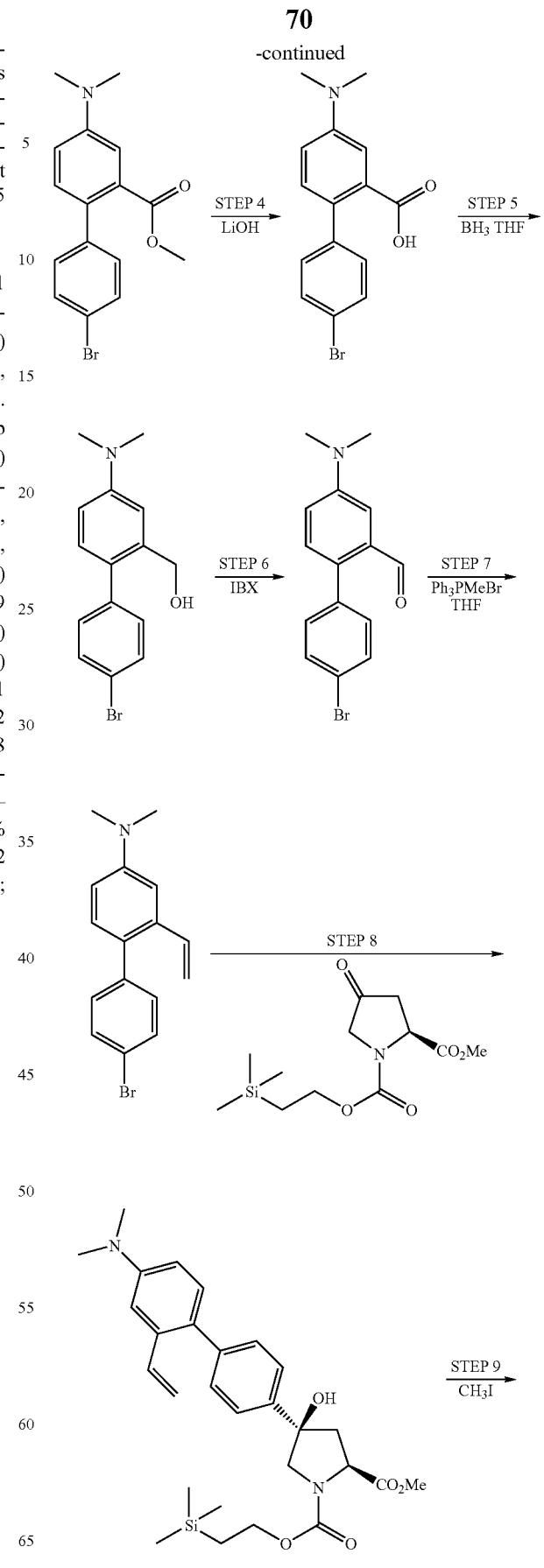

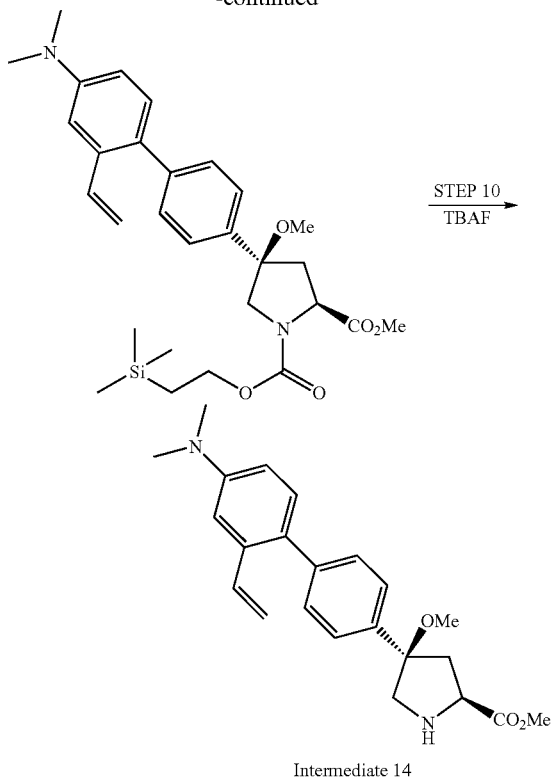

Intermediate 14

Step 1:

A solution of methyl 2-promo-5-nitrobenzoate (6 g, 23.07 mmol), potassium carbonate (9.6 g, 69.2 mmol) and 4-bromophenylboronic acid (6.02 g, 30.0 mmol) in DME (120 mL) and water (24 mL) (in a pressure vessel) was sparged with nitrogen for 15 min. Pd(PPh$_3$)$_3$ (0.80 g, 0.692 mmol) was added, and then the reaction was heated to 80° C. overnight. The reaction was cooled to r.t. and evaporated. The residue was diluted in EtOAc and washed with water then brine, dried over MgSO$_4$, filtered and evaporated to give the crude material. The crude material was purified by flash chromatography on the Biotage (0-15% EtOAc:Hex) to give methyl 4'-bromo-4-nitrobiphenyl-2-carboxylate (7.2 g, 21.42 mmol, 93% yield) as a light yellow solid. $^1$H NMR (500 MHz, CHLOROFORM-d) δ ppm 3.75 (s, 3H) 7.19 (m, 2H) 7.52 (d, J=8.55 Hz, 1H) 7.58 (m, 2H) 8.37 (dd, J=8.24, 2.44 Hz, 1H) 8.71 (d, J=2.44 Hz, 1H).).

Step 2:

Ammonium chloride (11.5 g, 214 mmol) and zinc (14.0 g, 214 mmol) were added to a solution of methyl 4'-bromo-4-nitrobiphenyl-2-carboxylate (7.2 g, 21.42 mmol) in MeOH (110 mL) and stirred at room temperature for 1 hour. The solid was filtered, and the filtrate was evaporated. The residue was dissolved in diethyl ether, filtered and concentrated to give methyl 4-amino-4'-bromobiphenyl-2-carboxylate (7.8 g, 25.5 mmol, 119% yield). LCMS: rt=1.54 min, [M+H]$^+$=305 and 307; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 3:

Dimethyl sulfate (7.30 mL, 76 mmol) was added to a mixture of methyl 4-amino-4'-bromobiphenyl-2-carboxylate (7.8 g, 25.5 mmol) and potassium carbonate (10.9 g, 79 mmol) in acetone (150 mL) and heated to reflux overnight. The reaction was cooled and water (10 mL) was added and continued stirring for 1 hr to destroy excess dimethyl sulfate. The reaction mixture was filtered and evaporated and then the residue taken up in DCM and washed with water. The organics were dried, filtered and evaporated to give the crude material. The crude material was purified on the Biotage (0-20% EtOAc:Hex) to give methyl 4'-bromo-4-(dimethylamino)biphenyl-2-carboxylate (1.9 g, 5.69 mmol, 22% yield) as an orange oil. $^1$H NMR (400 MHz, CHLOROFORM-d) δ ppm 3.03 (s, 6H) 3.66 (s, 3H) 6.87 (dd, J=8.66, 2.89 Hz, 1H) 7.12-7.18 (m, 3H) 7.21 (d, J=8.53 Hz, 1H) 7.46-7.51 (m, 2H). LCMS: rt=1.86 min. [M+H]$^+$=335; Phenomenex-Luna C-18 (5µ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 4:

2M Lithium hydroxide (8.5 mL, 17.0 mmol) was added to a solution of methyl 4'-bromo-4-(dimethylamino)biphenyl-2-carboxylate (1.9 g, 5.69 mmol) in THF (20 mL) and methanol (20 mL) and stirred at r.t. for 18 hrs. The reaction was then diluted with 1M HCl and extracted with EtOAc. The organic layer was washed with water then brine, dried over MgSO$_4$, filtered and then evaporated to give 4'-bromo-4-(dimethylamino)biphenyl-2-carboxylic acid (1.34 g, 4.19 mmol, 74% yield) as a white solid. LCMS: rt=1.54 min. [M+H]$^+$=319 and 321; Phenomenex-Luna C-18 (5µ) (3.0×50 mm); Solvent. A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 5:

4'-bromo-4-(dimethylamino)biphenyl-2-carboxylic acid (1.34 g, 4.19 mmol) in THF (40 mL) was cooled to 0° C. Borane tetrahydrofuran complex (8.37 mL, 8.37 mmol) was added dropwise over 15 min. and allowed to warm up to r.t. overnight. The reaction was diluted with EtOAc and washed with water, saturated ammonium chloride, and then brine. The organic layer was dried over MgSO$_4$, filtered and evaporated to give (4'-bromo-4-(dimethylamino)biphenyl-2-yl)methanol (1.25 g, 4.08 mmol, 98% yield) as a white solid. $^1$H NMR (500 MHz, CHLOROFORM-d) δ ppm 2.93-3.05 (m, 6H) 4.58 (s, 2H) 6.72 (dd, J=8.55, 2.75 Hz, 1H) 6.90 (d, J=2.75 Hz, 1H) 7.14 (d, J=8.55 Hz, 1H) 7.21-7.25 (m, 2H) 7.44-7.55 (m, 2H).

Step 6:

IBX (3.29 g, 11.76 mmol) was added to a solution of (4'-bromo-4-(dimethylamino)biphenyl-2-yl)methanol (1.8 g, 5.88 mmol) in dmso (50 mL) and stirred at 40° C. for 3 hours. The reaction was diluted with water and extracted with diethyl ether. The ether layer was dried over MgSO$_4$, filtered and evaporated to give the crude material. The crude product was purified on the Biotage (5-20% EtOAc:Hex) to give 4'-bromo-4-(dimethylamino)biphenyl-2-carbaldehyde (1.25 g, 4.11 mmol, 70% yield) as a yellow solid. $^1$H NMR (500 MHz, CHLOROFORM-d) δ 2.95-3.13 (m, 6H) 7.01 (dd, J=8.55, 3.05 Hz, 1H) 7.22 (m, 2H) 7.28-7.33 (m, 2H) 7.57 (m, 2H) 9.96 (s, 1H).

Step 7:

BuLi (2.5M in hexanes, 2.96 mL, 7.40 mmol) was added to a solution of methyltriphenylphosphonium bromide (2.94 g, 8.22 mmol) in THF (20 mL). The mixture was stirred at 0° C. for 1 hr. A solution of 4'-bromo-4-(dimethylamino)biphenyl-2-carbaldehyde (1.25 g, 4.11 mmol) in THF (20 mL) was added dropwise at 0° C. The mixture was stirred overnight from 0° C. to r.t. The reaction was filtered and evaporated. The residue was diluted with diethyl ether and washed with water and brine. The ether layer was dried (MgSO4), filtered and evaporated to give the crude material. The crude material was purified on the Biotage (5-15% EtOAc:Hex) to give 4'-bromo-N,N-dimethyl-2-vinylbiphenyl-4-amine (725 mg, 2.399 mmol, 58% yield) as a yellow solid. $^1$H NMR (500 MHz, CHLOROFORM-d) δ ppm 2.97-3.07 (m, 6H) 5.20 (d, J=10.99 Hz, 1H) 5.69 (d, J=17.40 Hz, 1H) 6.70 (dd, J=17.40, 10.99 Hz, 1H) 6.76 (dd, J=8.55, 2.75 Hz, 1H) 6.95 (d, J=2.44 Hz, 1H) 7.16 (d, J=8.55 Hz, 1H) 7.21 (m, J=8.24 Hz, 2H) 7.50 (m, J=8.55 Hz, 2H).

Step 8:

Magnesium (62 mg, 2.55 mmol) was stirred in a round bottom flask under $N_2$ for 15 min. to cause scratching of the surface of the magnesium turnings. 10 mL of THF was added to the magnesium turnings and stirred for an additional 30 min. 4'-bromo-N,N-dimethyl-2-vinylbiphenyl-4-amine (735 mg, 2.432 mmol) in THF (20 mL), was added dropwise at reflux with vigorous stirring. The Grignard solution was added to a solution of (S)-2-methyl 1-(2-(trimethylsilyl)ethyl) 4-oxopyrrolidine-1,2-dicarboxylate (699 mg, 2.432 mmol) in DCM (20 mL) at r.t. and stirred for 1 hr and then quenched with sat. $NH_4Cl$ solution. The aqueous layer was extracted with DCM and the combined organics were dried, filtered and evaporated to give crude material. The crude material was purified by flash chromatography on the Biotage (10-40% EtOAc:Hex) to give (2S,4R)-2-methyl 1-(2-(trimethylsilyl)ethyl) 4-(4'-(dimethylamino)-2'-vinylbiphenyl-4-yl)-4-hydroxypyrrolidine-1,2-dicarboxylate (330 mg, 0.646 mmol, 27% yield) as a yellow foam. $^1$H NMR (400 MHz, CHLOROFORM-d) δ ppm 0.04 (s, 9H) 0.99-1.11 (m, 2H) 2.34-2.52 (m, 1H) 2.62-2.81 (m, 1H) 3.00-3.07 (m, 6H) 3.68-3.81 (m, 1H) 3.82-3.89 (m, 3H) 4.17-4.34 (m, 3H) 4.49-4.68 (m, 1H) 5.19 (dd, J=11.04, 1.25 Hz, 1H) 5.70 (dd, J=17.57, 1.25 Hz, 1H) 6.67-6.80 (m, 2H) 6.96 (d, J=2.26 Hz, 1H) 7.16-7.22 (m, 1H) 7.34 (m, 2H) 7.49 (m, J=8.28 Hz, 2H). LCMS: rt=1.71 min. [M+H]+=511; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 9:

NaH (60% in oil) (46 mg, 1.163 mmol) was added to a solution of (2S,4R)-2-methyl 1-(2-(trimethylsilyl)ethyl) 4-(4'-(dimethylamino)-2'-vinylbiphenyl-4-yl)-4-hydroxypyrrolidine-1,2-dicarboxylate (330 mg, 0.646 mmol) and methyl iodide (0.073 mL, 1.163 mmol) at 0° C. in DMF and stirred at this temperature and allowed to warm up to r.t. overnight. The reaction was then quenched with saturated $NH_4Cl$ solution and ether. The ether layer was washed with brine, dried, filtered and evaporated to give crude material. The crude material was purified by flash chromatography on the Biotage (5-45% EtOAc in hexanes) to give the semi purified (2S,4R)-2-methyl 1-(2-(trimethylsilyl)ethyl) 4-(4'-(dimethylamino)-2'-vinylbiphenyl-4-yl)-4-methoxypyrrolidine-1,2-dicarboxylate (231 mg, 0.440 mmol, 68% yield) as a clear oil. LCMS: rt=1.86 min. [M+H]+=525; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 10:

TBAF (1.0M in THF, 1.7 mL, 1.7 mmol) was added to a solution of (2S,4R)-2-methyl 1-(2-(trimethylsilyl)ethyl) 4-(4'-(dimethylamino)-2'-vinylbiphenyl-4-yl)-4-methoxypyrrolidine-1,2-dicarboxylate (231 mg, 0.440 mmol) in THF (5 mL) and stirred at r.t. for 1 hr. The reaction was evaporated to give crude (2S,4R)-methyl 4-(4'-(dimethylamino)-2'-vinylbiphenyl-4-yl)-4-methoxypyrrolidine-2-carboxylate (167 mg, 0.439 mmol, 100% yield) as an orange oil used directly in next steps with no purification. LCMS: rt=1.01 min. [M-OMe]+=349; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 μL; wavelength=220.

Preparation of Compound 22:

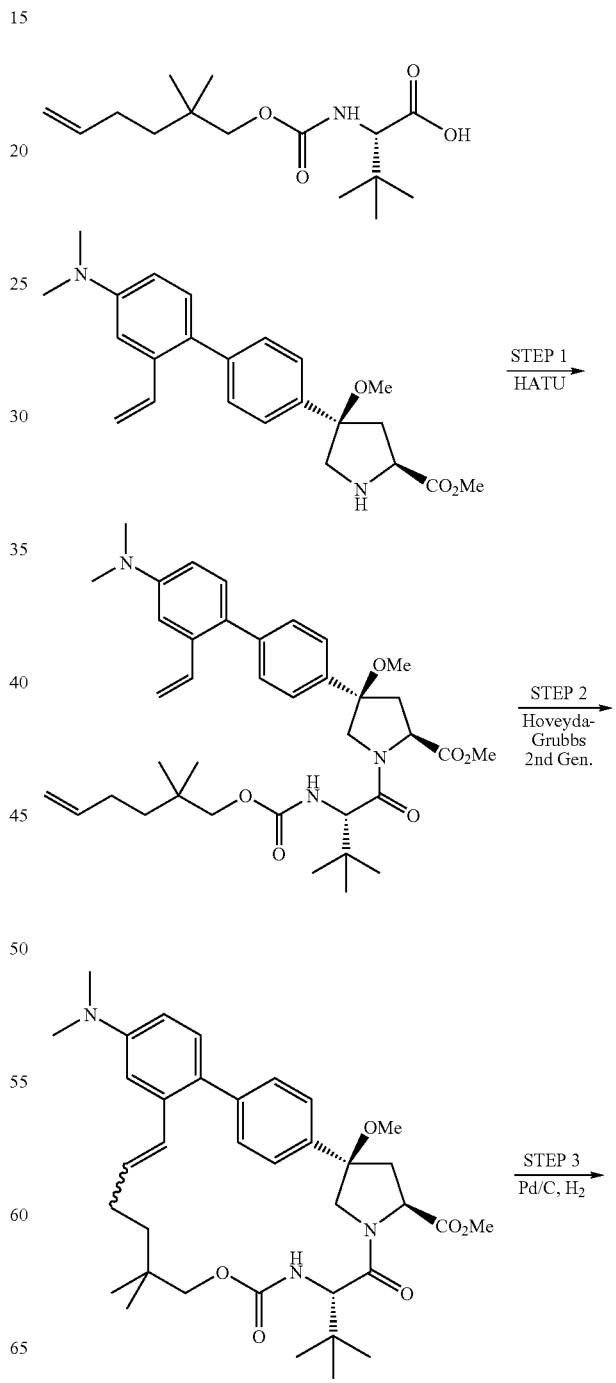

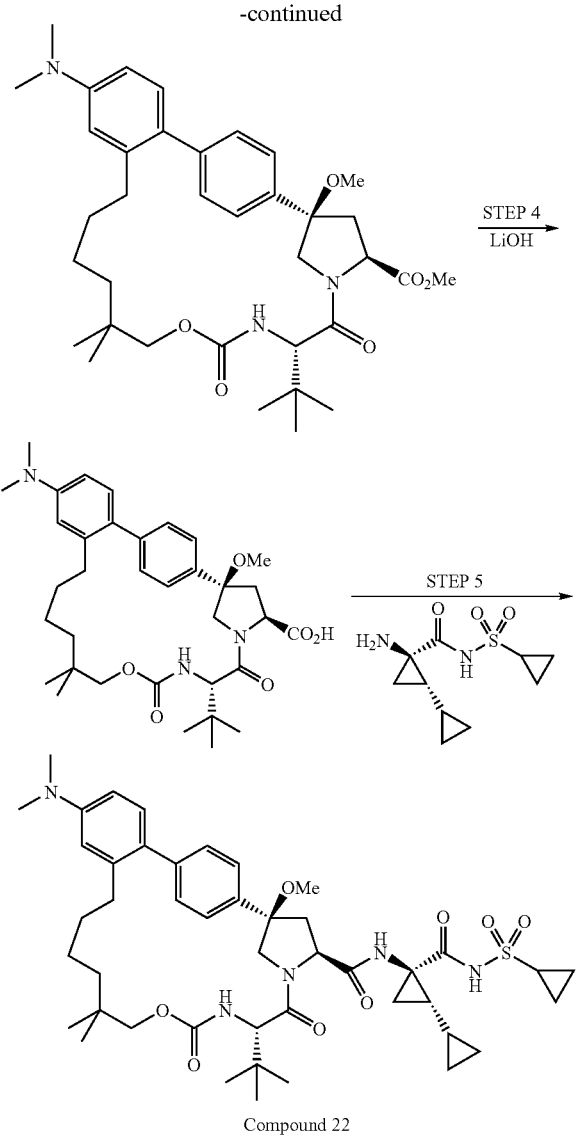

Compound 22

Step 1:

(S)-2-((2,2-dimethylhex-5-enyloxy)carbonylamino)-3,3-dimethylbutanoic acid (62 mg, 0.217 mmol), DIEA (0.076 mL, 0.434 mmol) and HATU (61 mg, 0.159 mmol) were added to a solution of (2S,4R)-methyl 4-(4'-(dimethylamino)-2'-vinylbiphenyl-4-yl)-4-methoxypyrrolidine-2-carboxylate (55 mg, 0.145 mmol) in DCM (3 mL). The reaction was stirred at r.t. for 2 hrs. The reaction was evaporated and purified on the Biotage (10-45% EtOAc:Hex) to give (2S,4R)-methyl 4-(4'-(dimethylamino)-2'-vinylbiphenyl-4-yl)-1-((S)-2-((2,2-dimethylhex-5-enyloxy)carbonylamino)-3,3-dimethylbutanoyl)-4-methoxypyrrolidine-2-carboxylate (61 mg, 0.094 mmol, 65% yield) as a yellow oil. LCMS: rt=2.00 min. [M-OMe]$^+$=616 and [M+H]$^+$=648; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 2:

(2S,4R)-methyl 4-(4'-(dimethylamino)-2'-vinylbiphenyl-4-yl)-1-((S)-2-((2,2-dimethylhex-5-enyloxy)carbonylamino)-3,3-dimethylbutanoyl)-4-methoxypyrrolidine-2-carboxylate (61 mg, 0.094 mmol) was dissolved in DCE (15 mL) and sparged with nitrogen for 15 min. Hoveyda-Grubbs catalyst (6 mg, 9.42 μmol) was added and heated in an oil bath to 80° C. overnight. The reaction was cooled, evaporated and purified by flash chromatography on the Biotage (10-45% EtOAc/Hex) to give the semi-purified product (53 mg, 0.086 mmol, 91% yield) as a clear oil. LCMS: rt=1.80 min. [M+H]$^+$=620; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 3:

The product from Step 2 (53 mg, 0.086 mmol) in MeOH (3 mL) was passed through a 10% palladium on carbon cartridge and hydrogenated in the H-Cube machine under 90 bar of H$_2$. The reaction was evaporated to give the product (30 mg, 0.048 mmol, 56% yield). LCMS: rt=1.74 min. [M+H]$^+$=622; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 4:

2.0M Lithium hydroxide (0.072 mL, 0.145 mmol) was added to a solution of product from Step 3 (30 mg, 0.048 mmol) in THF (1 mL) and MeOH (1 mL) and was stirred at r.t. overnight. The reaction was diluted with 1M HCl and extracted with EtOAc. The organic layer was washed with brine, dried over MgSO$_4$, filtered and evaporated to give the product (26 mg, 0.043 mmol, 89% yield) as an off-white foam. LCMS: rt=1.55 min. [M+H]$^+$=608; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Step 5:

DIEA (0.022 mL, 0.128 mmol), HATU (18 mg, 0.047 mmol), and (1S,2R)-2-amino-N-(cyclopropylsulfonyl)bi(cyclopropane)-2-carboxamide, HCl salt (14 mg, 0.051 mmol) were added to a solution of product from Step 4 (26 mg, 0.043 mmol) in DCM (1.5 mL). The reaction was stirred at r.t. for 4 hours. The reaction was evaporated and purified by prep HPLC to give Compound 22 (1 mg, 1.079 μmol, 2.5% yield) as a white solid. $^1$H NMR (500 MHz, CHLOROFORM-d) δ 0.29 (d, J=4.58 Hz, 2H) 0.49-0.63 (m, 1H) 0.77 (t, J=8.85 Hz, 6H) 0.83-0.93 (m, 6H) 1.02 (s, 9H) 1.11-1.19 (m, 2H) 1.25 (d, J=7.93 Hz, 4H) 1.33-1.46 (m, 4H) 1.82 (d, J=5.80 Hz, 1H) 2.31-2.53 (m, 1H) 2.65 (br. s., 2H) 2.98 (s, 6H) 3.09 (s, 3H) 3.89-4.04 (m, 1H) 4.29 (br. s., 1H) 4.13-4.45 (m, 1H) 5.31 (br. s., 1H) 6.55-6.75 (m, 3H) 7.07-7.17 (m, 1H) 7.28-7.32 (m, 4H) 7.37 (s, 1H). LCMS: rt=1.86 min. [M+H]$^+$=834; Phenomenex-Luna C-18 (5μ) (3.0×50 mm); Solvent A=10% acetonitrile—90% water—0.1% TFA, Solvent B=90% acetonitrile—10% water—0.1% TFA; gradient 0% to 100% solvent B over 2 min. and then hold for 1 min.; 4 mL/min; inj. vol.=5 uL; wavelength=220.

Biological Studies

HCV NS3/4A protease complex enzyme assays and cell-based HCV replicon assays were utilized in the present disclosure, and were prepared, conducted and validated as follows:

Generation of Recombinant HCV NS3/4A Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, *J. Clin. Microbiol.*, 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, *J. Proc. Natl. Acad. Sci. U.S.A.* 94(16), 8738-8743 (1997); AF054247, see Yanagi, M., St Claire, M., Shapiro, M., Emerson, S. U., Purcell, R. H. and Bukh, J., *Virology* 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains was manipulated as described by P. Gallinari et al. (see Gallinari P, Paolini C, Brennan D, Nardi C, Steinkuhler C, De Francesco R. *Biochemistry.* 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia coli* strain BL21 (DE3) (Invitrogen) following the protocol described by P. Gallinari et al. (see Gallinari P, Brennan D, Nardi C, Brunetti M, Tomei L, Steinkuhler C, De Francesco R., *J Virol.* 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton X-100, 1 microgram/milliliter ("fig/mL") lysozyme, 5 mM Magnesium Chloride (MgCl$_2$), 1 µg/ml DnaseI, 5 mM 3-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultra-centrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM (βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses. The enzyme was stored at −80° C., thawed on ice and diluted prior to use in assay buffer.

FRET Peptide Assay to Monitor HCV NS3/4A Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991) (FRET peptide), described by Taliani et al. in *Anal. Biochem.* 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time ting a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50

µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100 - [(\delta F_{inh}/\delta F_{con}) \times 100]$$

where $\delta F$ is the change in fluorescence over the linear range of the curve. A non-linear curve fit was applied to the inhibition-concentration data, and the 50% effective concentration ($IC_{50}$) was calculated by the use of Excel XLfit software using the equation, $y = A + ((B-A)/(1+((C/x)^D)))$.

Compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using a fluorometric Amino-Methyl-Coumarin (AMC) substrate specific for each enzyme was used as described previously (PCT Patent Application No. WO 00/09543) with some modifications to the serine protease assays. All enzymes were purchased from Sigma, EMDbiosciences while the substrates were from Bachem, Sigma and EMDbiosciences.

Compound concentrations varied from 100 to 0.4 µM depending on their potency. The enzyme assays were each initiated by addition of substrate to enzyme-inhibitor pre-incubated for 10 min at room temperature and hydrolysis to 15% conversion as measured on cytofluor.

The final conditions for each assay were as follows:
50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with 5 µM LLVY-AMC and 1 nM Chymotrypsin.
50 M Tris-HCl, pH 8.0, 50 mM NaCl, 0.1 mM EDTA, 3% DMSO, 0.02% Tween-20, 5 µM succ-AAPV-AMC and 20 nM FINE or 8 nM PPE;
100 mM NaOAC (Sodium Acetate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 µM Z-FR-AMC diluted in $H_2O$.

The percentage of inhibition was calculated using the formula:

$$[1-(UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel XLfit software.

Generation of HCV Replicon

An HCV replicon whole cell system was established as described by Lohmann V, Korner F, Koch J, Herian U, Theilmann L, Bartenschlager R., Science 285(5424):110-3 (1999). This system enabled us to evaluate the effects of our HCV Protease compounds on HCV RNA replication. Briefly, using the HCV strain 1b sequence described in the Lohmann paper (Assession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with SeaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence, of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomysin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnostic Systems) for a $CC_{50}$ reading. The toxicity of compound ($CC_{50}$) was determined by adding $\frac{1}{10}^{th}$ volume of alamar Blue to the media incubating the cells. After 4 h, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 µl). The cells were lysed with 25 µl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 µM final from a 2 mM stock in 100% DMSO. The plate was then placed into the Cytofluor 4000 instrument which had been set to 340 nm excitation/490 nm emission, automatic mode for 21 cycles and the plate read in a kinetic mode. $EC_{50}$ determinations were carried out as described for the $IC_{50}$ determinations.

HCV Replicon Luciferase Reporter Assay

As a secondary assay, $EC_{50}$ determinations from the replicon FRET assay were confirmed in a replicon luciferase reporter assay. Utilization of a replicon luciferase reporter assay was first described by Krieger et al (Krieger N, Lohmann V, and Bartenschlager R, *J. Viral.* 75(10):4614-4624 (2001)). The replicon construct described for our FRET assay was modified by inserting cDNA encoding a humanized form of the *Renilla* luciferase gene and a linker sequence fused directly to the 3'-end of the luciferase gene. This insert was introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, *Science* 290(5498):1972-1974). A stable cell line constitutively expressing this HCV replicon construct was generated as described above. The luciferase reporter assay was set up as described for the HCV replicon FRET assay with the following modifications. Following 4 days in a 37° C./5% $CO_2$ incubator, cells were analyzed for *Renilla* Luciferase activity using the Promega Dual-Glo Luciferase Assay System. Media (100 µl) was removed from each well containing cells. To the remaining 50 µl of media, 50 µl of Dual-Glo Luciferase Reagent was added, and plates rocked for 10 min to 2 h at room temperature. Dual-Glo Stop & Glo Reagent (50 µl) was then added to each well, and plates were rocked again for an additional 10 min to 2 h at room temperature. Plates were read on a Packard TopCount NXT using a luminescence program.

The percentage inhibition was calculated using the formula below:

$$\% \text{ control} = \frac{\text{average luciferase signal in experimental wells (+ compound)}}{\text{average luciferase signal in DMSO control wells (- compound)}}$$

The values were graphed and analyzed using XLfit to obtain the $EC_{50}$ value.

The compound of the current disclosure was tested and found to have the activity as follows: IC50: A=1 nM-3 nM; B=4 nM-7 nM; C=8 nM-11 nM; EC50: A 5.5 nM-10 nM; B=11 nM-20 nM; C=21 nM-30 nM.

TABLE 2

| Example Number | IC50 | EC50 |
|---|---|---|
| 1 | 1 nM | 5 nM |
| 2 | 1.5 nM | 16 nM |
| 3 | B | C |
| 4 | A | B |
| 5 | B | B |
| 6 | A | A |
| 7 | A | A |
| 8 | C | C |
| 9 | 4 nM | 26 nM |
| 10 | A | A |
| 11 | A | A |
| 12 | A | A |
| 13 | B | — |
| 14 | C | — |

TABLE 2-continued

| Example Number | IC50 | EC50 |
|---|---|---|
| 15 | B | — |
| 16 | B | — |
| 18 | A | — |
| 19 | A | — |
| 20 | A | — |
| 21 | A | — |
| 22 | A | — |

It will be evident to one skilled in the art that the present disclosure is not limited to the foregoing illustrative ei think xamples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

or a pharmaceutically acceptable salt thereof, wherein
n and n' are each independently 0, 1, 2 or 3;
$R^1$ is selected from hydroxy and $-NHSO_2R^6$;
$R^2$ is selected from hydrogen, alkenyl, alkyl, and cycloalkyl, wherein the alkenyl, the alkyl, and the cycloalkyl are each optionally substituted with one, two, three, or four halo groups;
$R^3$ is selected from hydrogen, alkoxy, alkylsulfanyl, alkylsulfonyl, alkylsulfoxyl, and hydroxy;
each $R^4$ and $R^{4'}$ are independently selected from alkoxy, alkyl, cyano, halo, haloalkoxy, haloalkyl, hydroxy, and $-NR^aR^b$;
$R^5$ is selected from hydrogen, alkenyl, alkyl, aryl, arylalkyl, cycloalkyl, (cycloalkyl)alkyl, heterocyclyl, and heterocyclylalkyl; wherein the alkyl and cycloalkyl are each optionally substituted with one group selected from alkoxy, haloalkoxy, halo, haloalkyl, cyano, and dialkylamino;
$R^6$ is selected from alkyl, aryl, arylalkyl, cycloalkyl, (cycloalkyl)alkyl, heterocyclyl, and $-NR^aR^b$; wherein the alkyl and cycloalkyl are each optionally substituted with one group selected from alkyl, alkoxy, halo, haloalkyl, cyano, cyanoalkyl, and haloalkoxy;

R$^a$ and R$^b$ are independently selected from hydrogen, alkoxy, alkyl, aryl, arylalkyl, cycloalkyl, (cycloalkyl)alkyl, haloalkyl, heterocyclyl, and heterocyclylalkyl;

Q is a C$_{4-8}$ saturated or unsaturated chain, wherein the chain is optionally substituted with one, two, three, or four groups independently selected from alkyl, halo, and haloalkyl, wherein the alkyl and haloalkyl groups can optionally form a 3-7 membered ring with the carbon atom to which they are attached; and Z is selected from O, CH$_2$, and NR$^z$, wherein R$^z$ is selected from hydrogen and alkyl.

2. A compound of claim 1, or a pharmaceutically acceptable salt thereof, wherein R$^1$ is —NHSO$_2$R$^6$.

3. A compound of claim 2, or a pharmaceutically acceptable salt thereof, wherein n and n' are each 0 or 1.

4. A compound of claim 3, or a pharmaceutically acceptable salt thereof, wherein Q is a C$_{4-7}$ saturated unsubstituted chain and Z is O.

5. A compound of claim 4, or a pharmaceutically acceptable salt thereof, wherein R$^3$ is alkoxy.

6. A compound of claim 5, or a pharmaceutically acceptable salt thereof, wherein R$^2$ is selected from alkenyl, alkyl optionally substituted with two halo groups, and unsubstituted cycloalkyl.

7. A compound of claim 6, or a pharmaceutically acceptable salt thereof, wherein R$^5$ is alkyl.

8. A compound of claim 1, or a pharmaceutically acceptable salt thereof, wherein R$^1$ is —NHSO$_2$R$^6$;

R$^2$ is selected from alkenyl, alkyl optionally substituted with two halo groups, and unsubstituted cycloalkyl; and R$^5$ is alkyl.

9. A compound of claim 1, or a pharmaceutically acceptable salt thereof, wherein n and n' are each 0 or 1;

R$^1$ is —NHSO$_2$R$^6$; wherein R$^6$ is cycloalkyl;

R$^2$ is alkenyl, alkyl optionally substituted with two halo groups, and unsubstituted cycloalkyl alkyl;

R$^3$ is alkoxy;

R$^5$ is alkyl;

Q is a C$_{4-7}$ saturated unsubstituted chain; and

Z is O.

10. A compound selected from

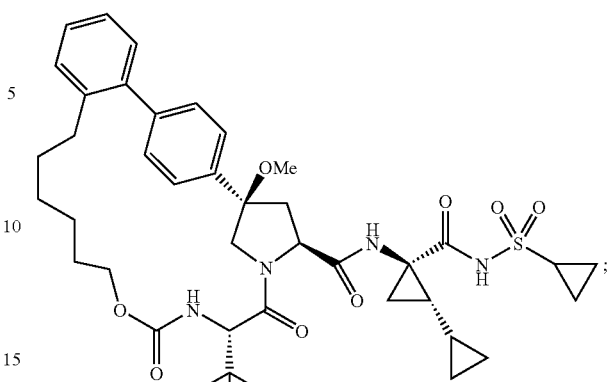

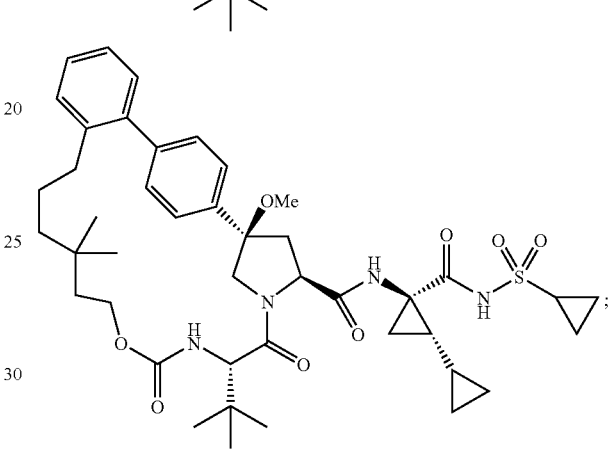

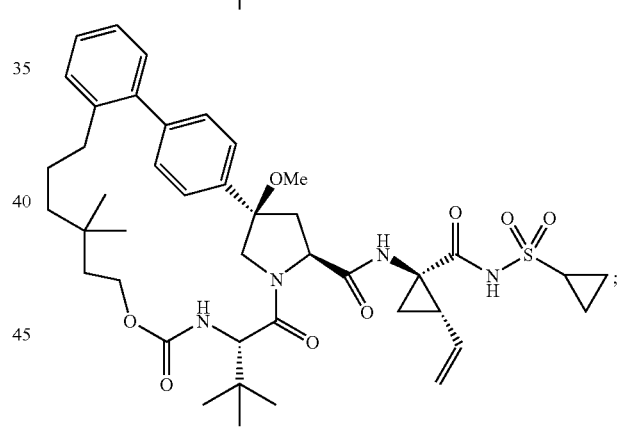

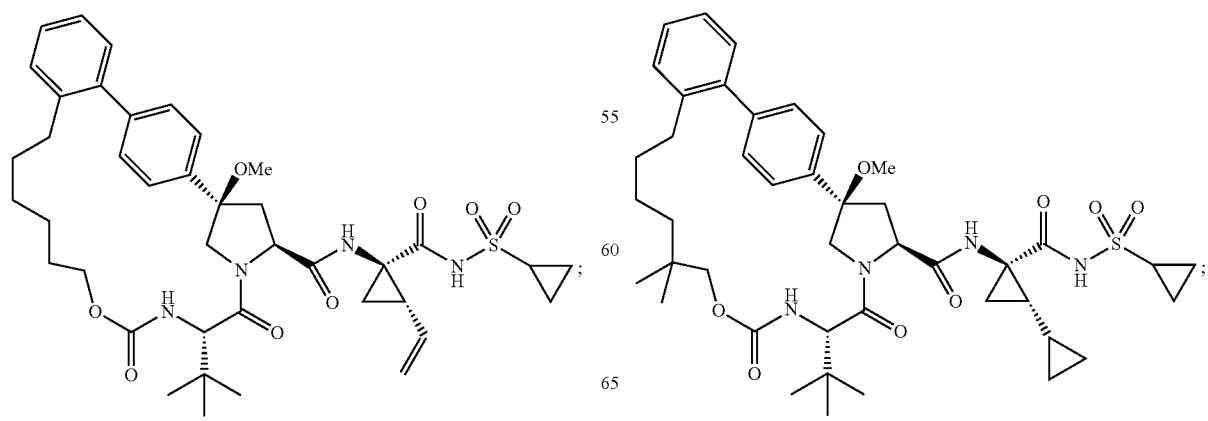

85
-continued
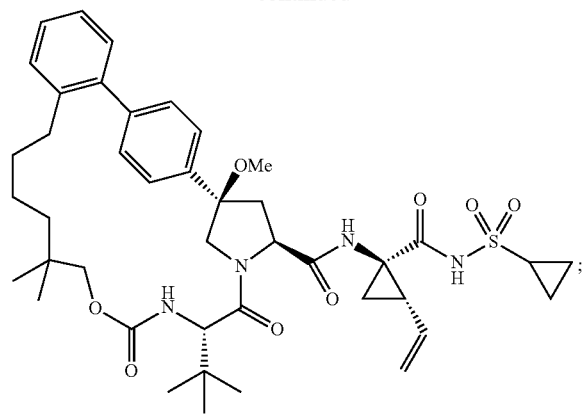
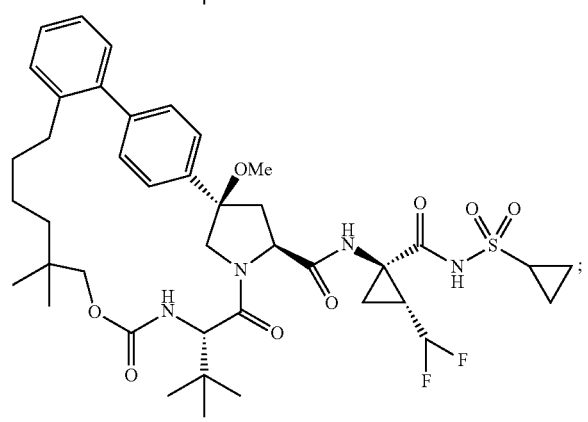
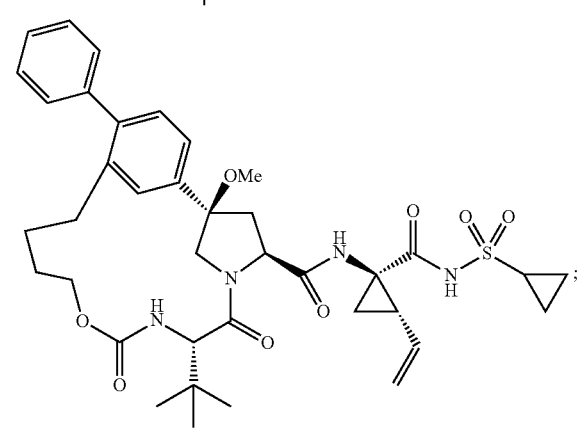
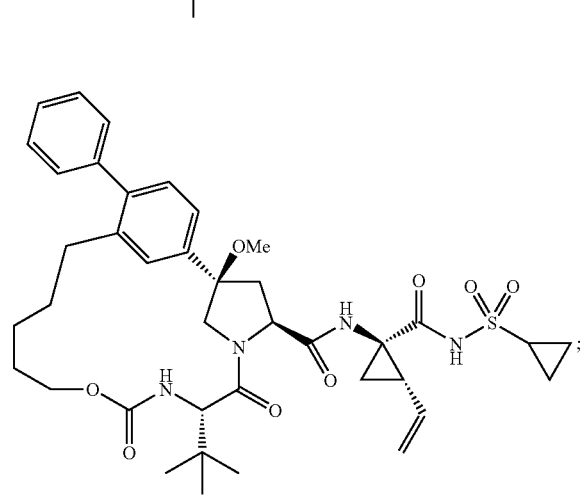
86
-continued
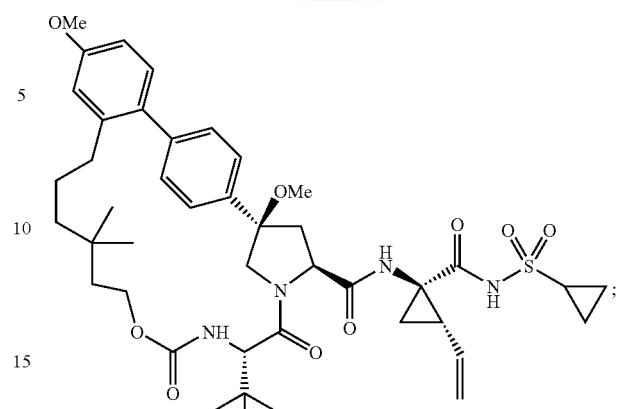
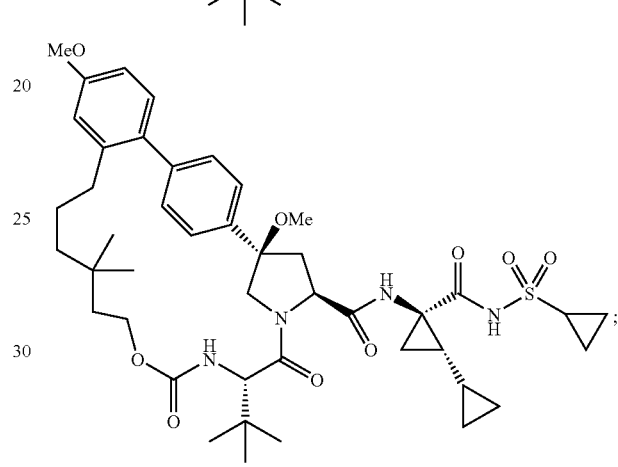
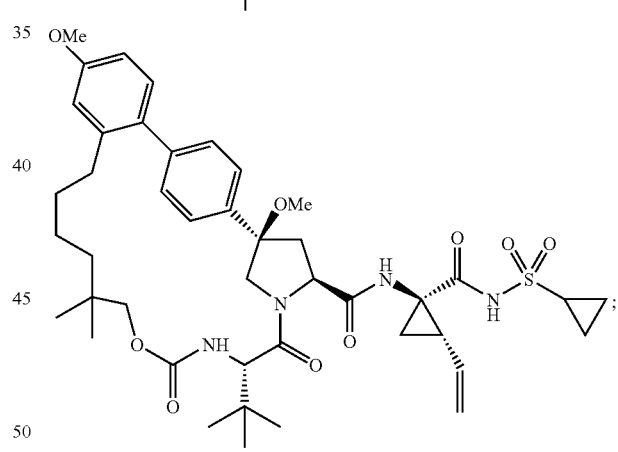
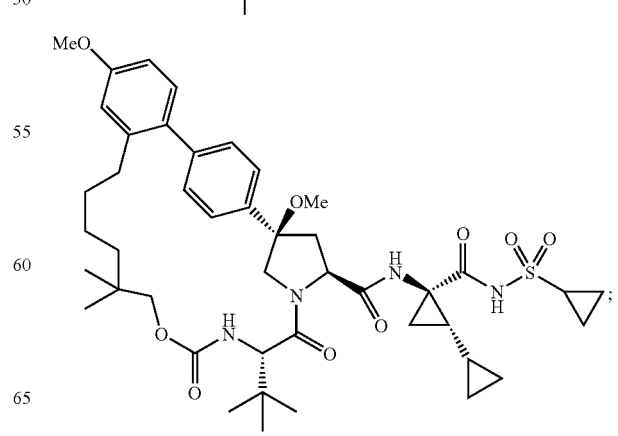

87
-continued
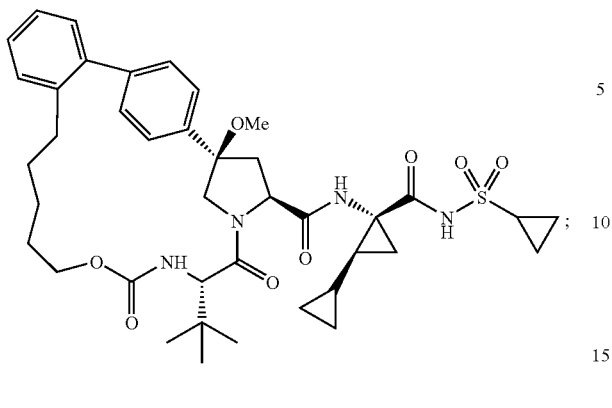
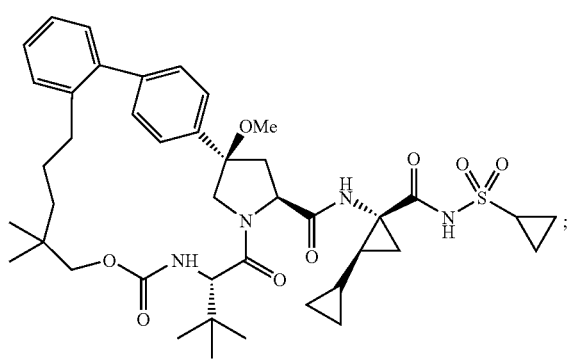
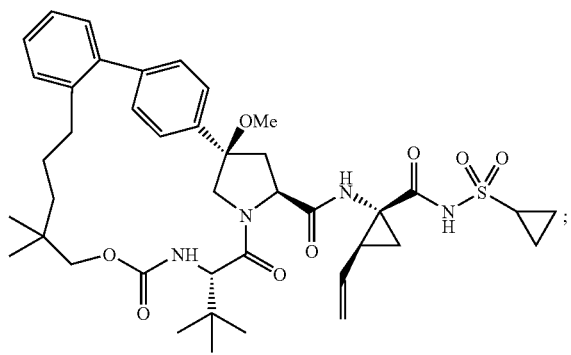
88
-continued
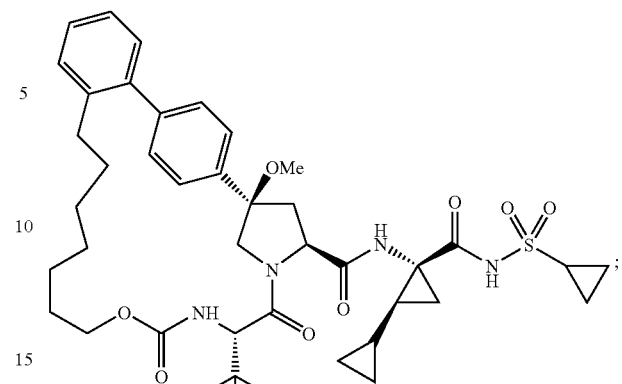
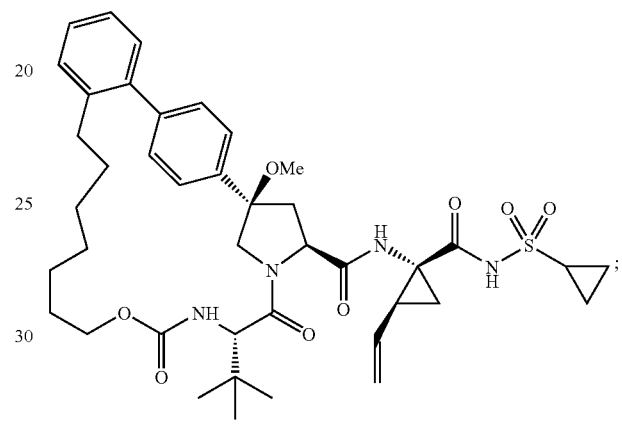
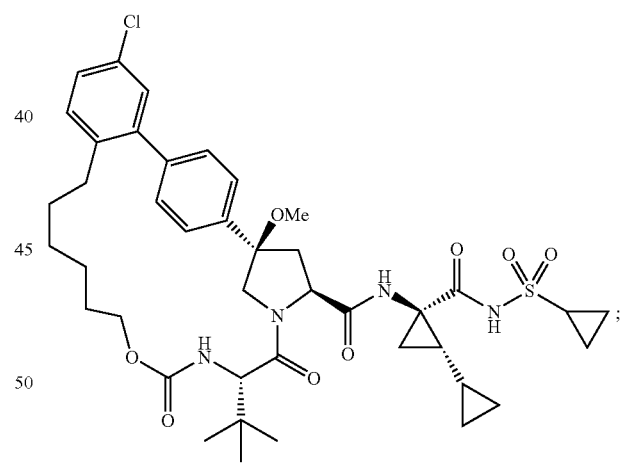
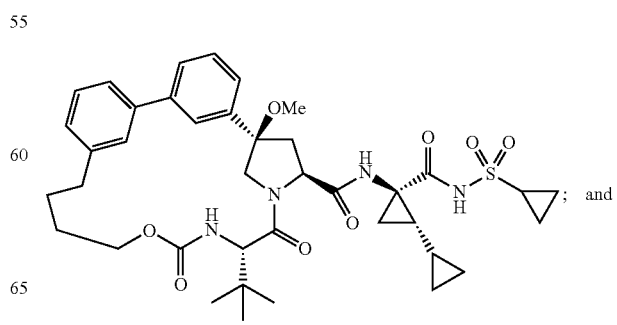
; and

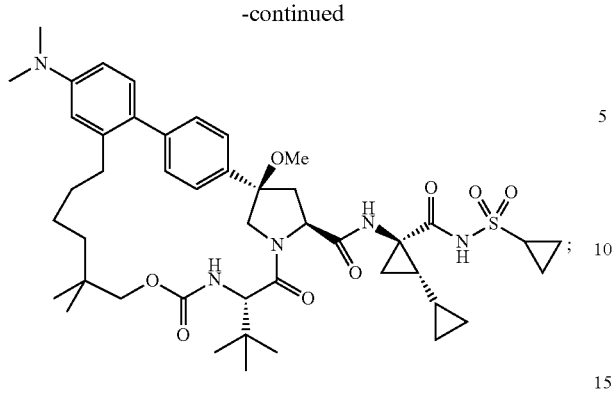
or a pharmaceutically acceptable salt thereof.
* * * * *